(12) United States Patent
Brister et al.

(10) Patent No.: US 10,610,396 B2
(45) Date of Patent: Apr. 7, 2020

(54) INTRAGASTRIC DEVICE

(71) Applicant: Obalon Therapeutics, Inc., Carlsbad, CA (US)

(72) Inventors: Mark C. Brister, Encinitas, CA (US); Paul D. Faucher, Escondido, CA (US); Neil R. Drake, San Diego, CA (US); Andrew P. Rasdal, San Diego, CA (US); Matthew S. Lake, Carlsbad, CA (US); Dubravka Markovic, San Diego, CA (US); Amy D. L. VandenBerg, San Diego, CA (US); Antonio C. Llevares, Chula Vista, CA (US); Josefina Nider, San Diego, CA (US)

(73) Assignee: Obalon Therapeutics, Inc., Carlsbad, CA (US)

( * ) Notice: Subject to any disclaimer, the term of this patent is extended or adjusted under 35 U.S.C. 154(b) by 131 days.

(21) Appl. No.: 15/906,942

(22) Filed: Feb. 27, 2018

(65) Prior Publication Data
US 2018/0185185 A1    Jul. 5, 2018

Related U.S. Application Data

(63) Continuation of application No. 15/690,095, filed on Aug. 29, 2017, now Pat. No. 10,463,520, which is a continuation of application No. 14/860,538, filed on Sep. 21, 2015, now Pat. No. 9,827,128, which is a continuation of application No. 14/227,195, filed on
(Continued)

(51) Int. Cl.
| | |
|---|---|
| *A61F 5/00* | (2006.01) |
| *A61M 25/00* | (2006.01) |
| *A61M 29/02* | (2006.01) |
| *A61M 25/10* | (2013.01) |

(52) U.S. Cl.
CPC ............ *A61F 5/003* (2013.01); *A61F 5/0036* (2013.01); *A61F 5/0089* (2013.01); *A61M 25/10181* (2013.11); *A61M 29/02* (2013.01); *A61M 25/10185* (2013.11)

(58) Field of Classification Search
CPC ....... A61F 5/003; A61F 5/0036; A61M 29/02; A61M 25/10181; A61M 25/10185; A61M 36/26; A61M 2039/267; A61M 2039/268
See application file for complete search history.

(56) References Cited

U.S. PATENT DOCUMENTS

| | | |
|---|---|---|
| 2,183,900 A | 12/1939 | Voit et al. |
| 3,788,322 A | 1/1974 | Michaels |
| (Continued) | | |

FOREIGN PATENT DOCUMENTS

| | | |
|---|---|---|
| CN | 101249006 | 8/2008 |
| DE | 3540936 | 10/1986 |
| (Continued) | | |

OTHER PUBLICATIONS

Al Kahtani et al., Bio-Enteric Intragastric Balloon in Obese Patients: A Retrospective Analysis of King Faisal Specialist Hospital Experience, OBES SURG, Aug. 28, 2008, 8 pp.
(Continued)

*Primary Examiner* — Anh T Dang
(74) *Attorney, Agent, or Firm* — Knobbe, Martens, Olson & Bear, LLP

(57) ABSTRACT

Devices and methods for treating obesity are provided. More particularly, intragastric devices and methods of fabricating, deploying, inflating, monitoring, and retrieving the same are provided.

26 Claims, 51 Drawing Sheets

Related U.S. Application Data

Mar. 27, 2014, now Pat. No. 9,351,862, which is a continuation of application No. 13/510,921, filed as application No. PCT/US2011/022165 on Jan. 21, 2011, now Pat. No. 8,740,927.

(56) References Cited

U.S. PATENT DOCUMENTS

| | | |
|---|---|---|
| 3,797,492 A | 3/1974 | Place |
| 4,133,315 A | 1/1979 | Berman et al. |
| 4,234,454 A | 11/1980 | Strope |
| 4,236,521 A | 12/1980 | Lauterjung |
| 4,246,893 A | 1/1981 | Berson |
| 4,340,626 A | 7/1982 | Rudy |
| 4,416,267 A | 11/1983 | Garren et al. |
| 4,485,805 A | 12/1984 | Foster, Jr. |
| 4,489,440 A | 12/1984 | Chaoui |
| 4,517,979 A | 5/1985 | Pecenka |
| 4,545,367 A | 10/1985 | Tucci |
| 4,560,392 A | 12/1985 | Basevi |
| 4,607,618 A | 8/1986 | Angelchik |
| 4,694,827 A | 9/1987 | Weiner et al. |
| 4,718,639 A | 1/1988 | Sherwood et al. |
| 4,723,547 A | 2/1988 | Kullas et al. |
| 4,739,758 A | 4/1988 | Lai et al. |
| 4,812,315 A | 3/1989 | Tarabishi |
| 4,813,934 A | 3/1989 | Engelson et al. |
| 4,857,029 A | 8/1989 | Dierick et al. |
| 4,899,747 A | 2/1990 | Garren et al. |
| 4,917,885 A | 4/1990 | Chiba et al. |
| 4,925,446 A | 5/1990 | Garay et al. |
| 4,929,214 A | 5/1990 | Liebermann |
| 5,049,106 A | 9/1991 | Kim et al. |
| 5,084,061 A | 1/1992 | Gau et al. |
| 5,129,915 A | 7/1992 | Cantenys et al. |
| 5,234,454 A | 8/1993 | Bangs |
| 5,259,399 A | 11/1993 | Brown |
| 5,270,086 A | 12/1993 | Hamlin |
| 5,308,326 A | 5/1994 | Zimmon |
| 5,431,917 A | 7/1995 | Yamamoto et al. |
| 5,713,141 A | 2/1998 | Mitchell et al. |
| 5,728,119 A | 3/1998 | Smith et al. |
| 5,817,099 A | 10/1998 | Skolik et al. |
| 5,852,889 A | 12/1998 | Rinaldi |
| 5,868,141 A | 2/1999 | Ellias |
| 5,897,205 A | 4/1999 | Sinsteden |
| 5,910,128 A | 6/1999 | Quinn |
| 5,938,669 A | 8/1999 | Klaiber |
| 6,427,089 B1 | 7/2002 | Knowlton |
| 6,454,785 B2 | 9/2002 | De Hoyos Garza |
| 6,579,301 B1 | 6/2003 | Bales et al. |
| 6,627,206 B2 | 9/2003 | Lloyd |
| 6,682,473 B1 | 1/2004 | Matsuura et al. |
| 6,689,141 B2 | 2/2004 | Ferrera |
| 6,733,512 B2 | 5/2004 | McGhan et al. |
| 6,981,980 B2 | 1/2006 | Sampson et al. |
| 6,988,983 B2 | 1/2006 | Connors et al. |
| 7,101,396 B2 | 9/2006 | Artof et al. |
| 7,112,186 B2 | 9/2006 | Shah |
| 7,192,397 B2 | 3/2007 | Lewkowicz et al. |
| 7,674,396 B2 | 3/2010 | Sterling |
| 7,682,306 B2 | 3/2010 | Shah |
| 7,699,863 B2 | 4/2010 | Marco et al. |
| 7,753,949 B2 | 7/2010 | Lamphere et al. |
| 7,785,291 B2 | 8/2010 | Marco |
| 7,854,745 B2 | 12/2010 | Brister et al. |
| 7,879,355 B2 | 2/2011 | Sterling |
| 7,972,378 B2 | 7/2011 | Tabor et al. |
| 8,066,780 B2 | 11/2011 | Chen |
| 8,162,969 B2 | 4/2012 | Brister et al. |
| 8,202,291 B1 | 6/2012 | Brister et al. |
| 8,282,666 B2 | 10/2012 | Birk |
| 8,287,562 B2 | 10/2012 | Kasic et al. |
| 8,292,911 B2 | 10/2012 | Brister |
| 8,562,589 B2 | 10/2013 | Imran |
| 8,647,358 B2 | 2/2014 | Brister et al. |
| 8,721,620 B2 | 5/2014 | Imran |
| 8,734,429 B2 | 5/2014 | Imran et al. |
| 8,740,927 B2 | 6/2014 | Brister et al. |
| 8,764,733 B2 | 7/2014 | Imran |
| 8,809,269 B2 | 8/2014 | Imran |
| 8,809,271 B2 | 8/2014 | Imran |
| 8,845,674 B2 | 9/2014 | Brister et al. |
| 8,870,966 B2 | 10/2014 | Schwab et al. |
| 8,992,561 B2 | 3/2015 | Brister et al. |
| 9,011,477 B2 | 4/2015 | Brister et al. |
| 9,173,758 B2 | 11/2015 | Brister et al. |
| 9,351,862 B2 | 5/2016 | Brister et al. |
| 9,468,550 B2 | 10/2016 | Brister et al. |
| 9,539,132 B2 | 1/2017 | Brister et al. |
| 9,662,239 B2 | 5/2017 | Brister et al. |
| 9,827,128 B2 | 11/2017 | Brister et al. |
| 2003/0021822 A1 | 1/2003 | Lloyd |
| 2003/0171768 A1 | 9/2003 | McGhan |
| 2004/0044351 A1 | 3/2004 | Searle |
| 2004/0044357 A1 | 3/2004 | Gannoe |
| 2004/0102677 A1 | 5/2004 | Frering |
| 2005/0118370 A1 | 6/2005 | Varma et al. |
| 2005/0222329 A1 | 10/2005 | Shah et al. |
| 2005/0266109 A1 | 12/2005 | Chin et al. |
| 2005/0267405 A1 | 12/2005 | Shah |
| 2005/0267595 A1 | 12/2005 | Chen et al. |
| 2006/0058829 A1 | 3/2006 | Sampson et al. |
| 2006/0224145 A1 | 10/2006 | Gillis et al. |
| 2007/0078476 A1 | 4/2007 | Hull et al. |
| 2007/0100208 A1 | 5/2007 | Lewkowicz et al. |
| 2007/0100369 A1 | 5/2007 | Cragg et al. |
| 2007/0104754 A1 | 5/2007 | Sterling et al. |
| 2007/0104755 A1 | 5/2007 | Sterling et al. |
| 2007/0118168 A1 | 5/2007 | Lointier |
| 2007/0149994 A1 | 6/2007 | Sosnowski et al. |
| 2007/0156248 A1 | 7/2007 | Marco et al. |
| 2007/0173881 A1 | 7/2007 | Birk et al. |
| 2007/0207199 A1 | 9/2007 | Sogin et al. |
| 2007/0212559 A1 | 9/2007 | Shah |
| 2007/0250087 A1 | 10/2007 | Makower |
| 2007/0250101 A1 | 10/2007 | Horn et al. |
| 2007/0288033 A1 | 12/2007 | Murature et al. |
| 2008/0051866 A1 | 2/2008 | Chen et al. |
| 2008/0172079 A1 | 7/2008 | Birk |
| 2008/0215003 A1 | 9/2008 | Kornerup |
| 2008/0243166 A1 | 10/2008 | Paganon |
| 2008/0255601 A1 | 10/2008 | Birk |
| 2008/0306506 A1 | 12/2008 | Leatherman et al. |
| 2009/0082644 A1 | 3/2009 | Li |
| 2009/0118756 A1 | 5/2009 | Valencon et al. |
| 2009/0182368 A1 | 7/2009 | Lunsford et al. |
| 2009/0182424 A1 | 7/2009 | Marco et al. |
| 2009/0192535 A1 | 7/2009 | Kasic, II et al. |
| 2009/0222065 A1 | 9/2009 | Dlugos et al. |
| 2009/0259246 A1 | 10/2009 | Eskaros et al. |
| 2010/0063530 A1 | 3/2010 | Valencon |
| 2010/0100115 A1 | 4/2010 | Soetermans et al. |
| 2010/0168782 A1 | 7/2010 | Hancock |
| 2010/0198249 A1 | 8/2010 | Sabliere |
| 2010/0222802 A1 | 9/2010 | Gillespie et al. |
| 2011/0202127 A1 | 8/2011 | Mauch et al. |
| 2011/0295300 A1 | 12/2011 | Verd et al. |
| 2012/0010590 A1 | 1/2012 | Imran |
| 2012/0269365 A1 | 1/2012 | Ochiai et al. |
| 2012/0191124 A1 | 7/2012 | Brister |
| 2012/0265234 A1 | 10/2012 | Brister |
| 2012/0296365 A1 | 11/2012 | Nguyen |
| 2013/0165859 A1 | 6/2013 | Imran |
| 2013/0226219 A1 | 8/2013 | Brister et al. |
| 2013/0267983 A1 | 10/2013 | Pavlovic et al. |
| 2014/0066968 A1 | 3/2014 | Pavlovic et al. |
| 2014/0221912 A1 | 8/2014 | Imran |
| 2014/0221927 A1 | 8/2014 | Imran et al. |
| 2015/0374525 A1 | 12/2015 | Brister et al. |
| 2016/0193064 A1 | 7/2016 | Brister et al. |
| 2016/0257911 A1 | 9/2016 | Denison et al. |
| 2017/0027728 A1 | 2/2017 | Brister et al. |
| 2017/0079821 A1 | 3/2017 | Brister et al. |

(56) References Cited

U.S. PATENT DOCUMENTS

| | | |
|---|---|---|
| 2017/0127778 A1 | 6/2017 | Tuning |
| 2017/0172778 A1 | 6/2017 | Brister et al. |
| 2018/0008446 A1 | 1/2018 | Brister et al. |
| 2018/0064569 A1 | 3/2018 | Brister et al. |
| 2018/0221633 A1 | 8/2018 | Brister et al. |
| 2019/0000655 A1 | 1/2019 | Brister et al. |

FOREIGN PATENT DOCUMENTS

| | | |
|---|---|---|
| EP | 0 103 481 | 3/1984 |
| EP | 0 213 748 | 3/1987 |
| EP | 0 246 999 | 11/1987 |
| WO | WO 87/00034 | 1/1987 |
| WO | WO 99/25418 | 5/1999 |
| WO | WO 01/68007 | 9/2001 |
| WO | WO 02/16001 | 2/2002 |
| WO | WO 02/40081 | 5/2002 |
| WO | WO 02/091961 | 11/2002 |
| WO | WO 03/055420 | 7/2003 |
| WO | WO 04/084763 | 10/2004 |
| WO | WO 05/094257 | 10/2005 |
| WO | WO 06/020929 | 2/2006 |
| WO | WO 07/136735 | 11/2007 |
| WO | WO 09/055386 | 4/2009 |
| WO | WO 09/059802 | 5/2009 |
| WO | WO 09/059803 | 5/2009 |
| WO | WO 09/086119 | 7/2009 |

OTHER PUBLICATIONS

Al-Momen et al., Intragastric Balloon for Obesity: A Retrospective Evaluation of Tolerance and Efficacy, OBES SURG, 2005, 15(1):101-105.

Benjamin et al., Double-Blind Controlled Trial of the Garren-Edwards Gastric Bubble: An Adjunctive Treatment for Exogenous Obesity, Gastroenterology, Sep. 1988, 95(3):581-588.

Carvalho et al., An Improved Intragastric Balloon Procedure Using a New Balloon: Preliminary Analysis of Safety and Efficacy, OBES SURG, 2008, 6 pp.

Coskun et al., Bioenterics Intragastric Balloon: Clinical Outcomes of the First 100 Patients—A Turkish Experience, OBES SURG, Sep. 2008, 18(9):1154-6. published online Jun. 3, 2008.

Dastis et al., Intragastric Balloon for Weight Loss: Results in 100 Individuals Followed for at Least 2.5 Years, Endoscopy, Jul. 2009, 41(7):575-580.

De Waele et al., Endoscopic Volume Adjustment of Intragastric Balloons for Intolerance, OBES SURG, Apr. 2001, 11(2):223-224.

Doldi et al., Treatment of Morbid Obesity With Intragastric Balloon in Association With Diet, OBES SURG, 2002, 12(4):583-587.

Dumonceau, Evidence-Based Review of the Bioenterics Intragastric Balloon for Weight Loss, OBES SURG. Dec. 2008,18(12):1611-1617.

Durrans et al., Comparison of Weight Loss With Short Term Dietary and Intragastric Balloon Treatment, Gut 1989, 30:565-568.

Eckhauser et al., Hydrostatic Balloon Dilation for Stomal Stenosis after Gastric Partitioning, Surgical Gastroenterology, 3(1):43-50, 1984.

Evans et al., Intragastric Balloon in the Treatment of Patients With Morbid Obesity, British Journal of Surgery, 2001, 88:1245-1248.

Fernandes et al., Intragastric Balloon for Obesity (Review), Cochrane Review, Jan. 24, 2007, Issue 1.

Forestieri et al., Heliosphere Bag in the Treatment of Severe Obesity: Preliminary Experience, OBES SURG, May 2006, 16(5):635-637.

Gaggiotti et al., Adjustable Totally Implanted Intragastric Prosthesis (ATIIP). Endogast for Treatment of Morbid Obesity: One Year Follow-Up of a Multicenter Prospective Clinical Survey, Obesity Surgery, 2007, 17, 949-956.

Geliebter et al., Gastric balloon to treat obesity: a double-blind study in nondieting subjects, The American Journal of Clinical Nutrition, 1990, 51:584-588.

Genco et al., Bioenterics Intragastric Balloon (BIB): A Short-Term, Double-Blind, Randomized, Controlled, Crossover Study on Weight Reduction in Morbidly Obese Patients, International Journal of Obesity (Lond), Jan. 2006, 30(1):129-33, published online Sep. 27, 2005.

Genco et al., Bioenterics Intragastric Balloon: The Italian Experience With 2,515 Patients, OBES SURG, 2005, 15(8):1161-1164.

Genco et al., Intragastric Balloon or Diet Alone? A Retrospective Evaluation, OBES SURG, Aug. 2008, 18(8):989-92. published online May 16, 2008.

Genco et al., Laparoscopic Sleeve Gastrectomy Versus Intragastric Balloon: A Case-Control Study, Surg Endosc. Springer Science & Business Media, published online Jan. 24, 2009.

Gottig et al., Analysis of Safety and Efficacy of Intragastric Balloon in Extremely Obese Patients, OBES SURG, Jun. 2009, 19(6):677-683. published online Mar. 17, 2009.

Imaz et al., Safety and Effectiveness of the Intragastric Balloon for Obesity. A Meta-Analysis, OBES SURG, Jul. 2008,18(7):841-846, published online May 6, 2008.

Langer, R., Drug delivery and targeting, Nature, Suuplement to, Apr. 1998, 392(6679):5-10.

Malik, Endoluminal and Transluminal Surgery: Current Status and Future Possibilities, Surgical Endoscopy, 2006, 20(8):1179-1192.

Martin et al., Safety of the Ullorex Oral Intragastric Balloon for the Treatment of Obesity, Journal of Diabetic Science and Technology, Jul. 2007, 1(4):574-581.

Mathus-Vliegen et al., Intragastric Ballon in the Treatment of Super-morbid Obesity—Double-Blind, Sham-Controlled, Crossover Evaluation of 500-Milliliter Balloon, Gastroenterology, Aug. 1990, 99(2):362-369.

Melissas et al., The Intragastric Balloon—Smoothing the Path to Bariatric Surgery, OBES SURG, 2006, 16:897-902.

Mion et al., Tolerance and Efficacy of an Air-Filled Balloon in Non-Morbidly Obese Patients: Results of a Prospective Multicenter Study, OBES SURG, Jul. 2007, 17(7):764-769.

Nieben et al., Ingtragastric Balloon as an Artificial Bezoar for Treatment of Obesity, The Lancet, Jan. 1982, 1(8265):198-199.

Ramhamadany et al, Effect of the Gastric Balloon Versus Sham Procedure on Weight Loss in Obese Subjects, Gut, 1989, 30:1054-1057.

Rodriguez-Hermosa et al., Gastric Necrosis: A Possible Complication of the Use of the Intragastric Balloon in a Patient Previously Submitted to Nissen Fundoplication, OBES SURG, 19:1456-1459, published online Jun. 9, 2009.

Roman et al., Intragastric Balloon for "Non-Morbid" Obesity: A Retrospective Evaluation of Tolerance and Efficacy, OBES SURG, Apr. 2004, 14(4):539-544.

Sallet et. al. Brazilian Multicenter Study of the Intragastric Balloon, Obesity Surgery, Aug. 2004, 14(7):991-998.

Totte et al., Weight Reduction by Means of Intragastric Device: Experience With the Bioenterics Intragastric Balloon, OBES SURG, Aug. 2001 11(4):519-523.

Trande et al., Efficacy, Tolerance and Safety of New Intragastric Air-Filled Balloon (Heliosphere BAG) for Obesity: The Experience of 17 Cases, OBES SURG, Dec. 10, 2008.

Vansonnenberg et al., Percutaneous Gastrostomy: Use of Intragastric Ballon Support, Radiology, Aug. 1984, 152(2):531-532.

Wahlen et al., The Bioenterics Intragastric Balloon (BIB): How to Use It, OBES SURG, 2001,11(4):524-527.

International Search Report and Written Opinion dated Oct. 31, 2011 for PCT/US2011/022165 filed Jan. 21, 2011.

DuPont, Newest Online Modeling Tool Simplifies Tie Layer Selection, product brochure, http://www2.dupont.com/Packaging_Resins/en_US/whats_new/article20120618_tie_resin_tool.html, Jun. 18, 2012.

DuPont™ Bynel® resins, product brochure, http://www2.dupont.com/Bynel/en_US/—Copyright© 2012.

LyondellBasell, Selecting a Tie-Layer Adhesive, product brochure, http://www.lyondellbasell.com/Products/ByCategory/polymers/type/Polyethylene/SpecialtyPolyethylene/TieLayerResins/Selecting_a_Tie_layer_Adhesive.htm—2012.

LyondellBasell, Tie-Layer Resins, product brochure, http://www.lyondellbasell.com/Products/ByCategory/polymers/process/TieLayerResins/—2012.

(56) References Cited

OTHER PUBLICATIONS

Mitsui Chemicals America, Inc., ADMER™ Adhesive Resin, product brochure, http://www.mitsuichemicals.com/adm.htm, Copyright 1999-2012.

Westlake Chemical, Tie Layer, product brochure, http://www.westlake.com/fw/main/Tie-Layer-170.html—2012.

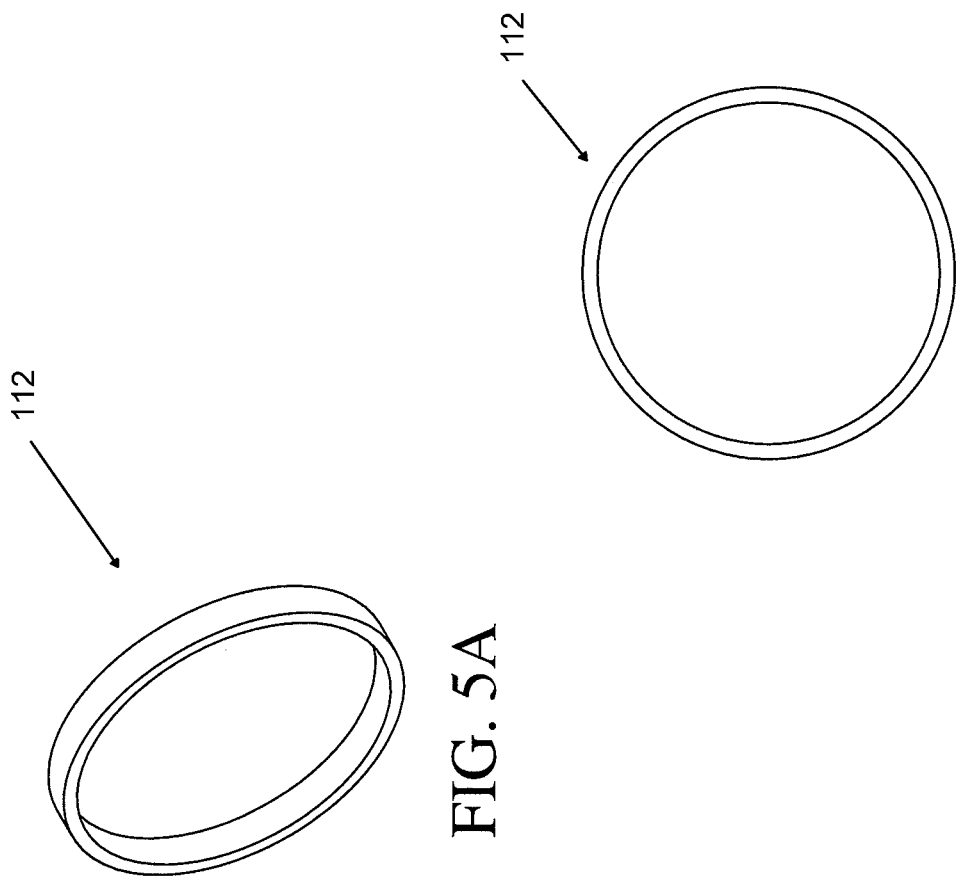

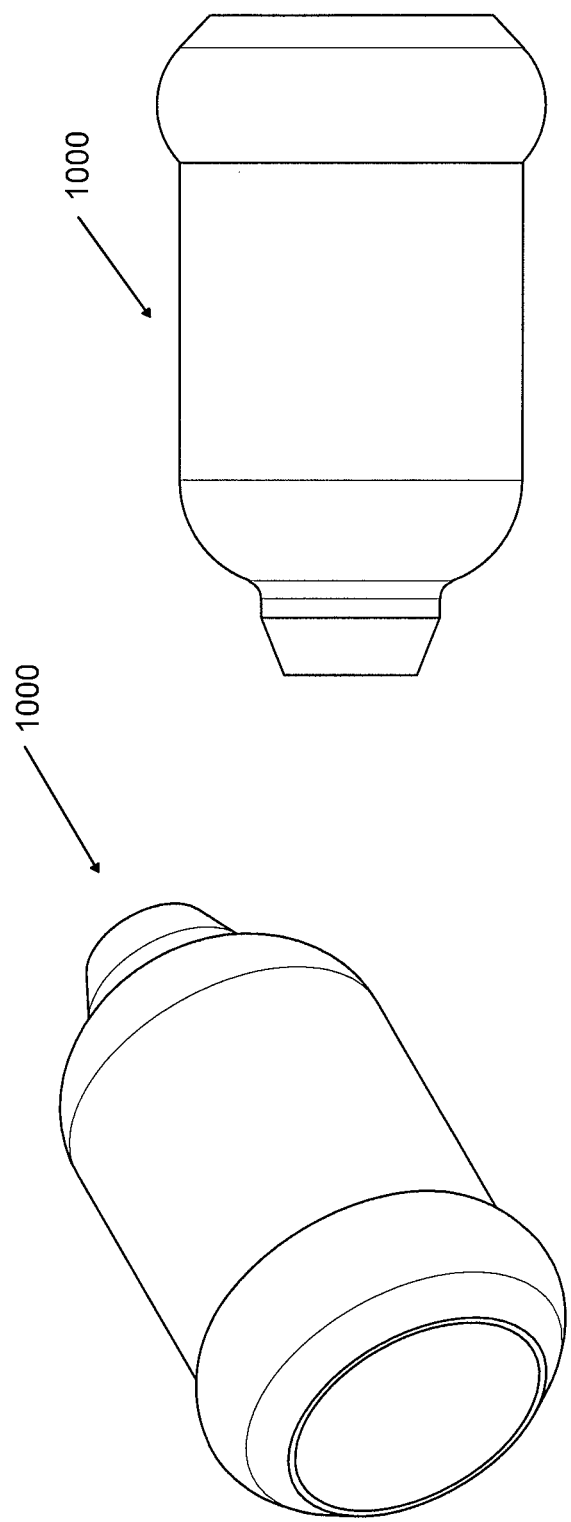

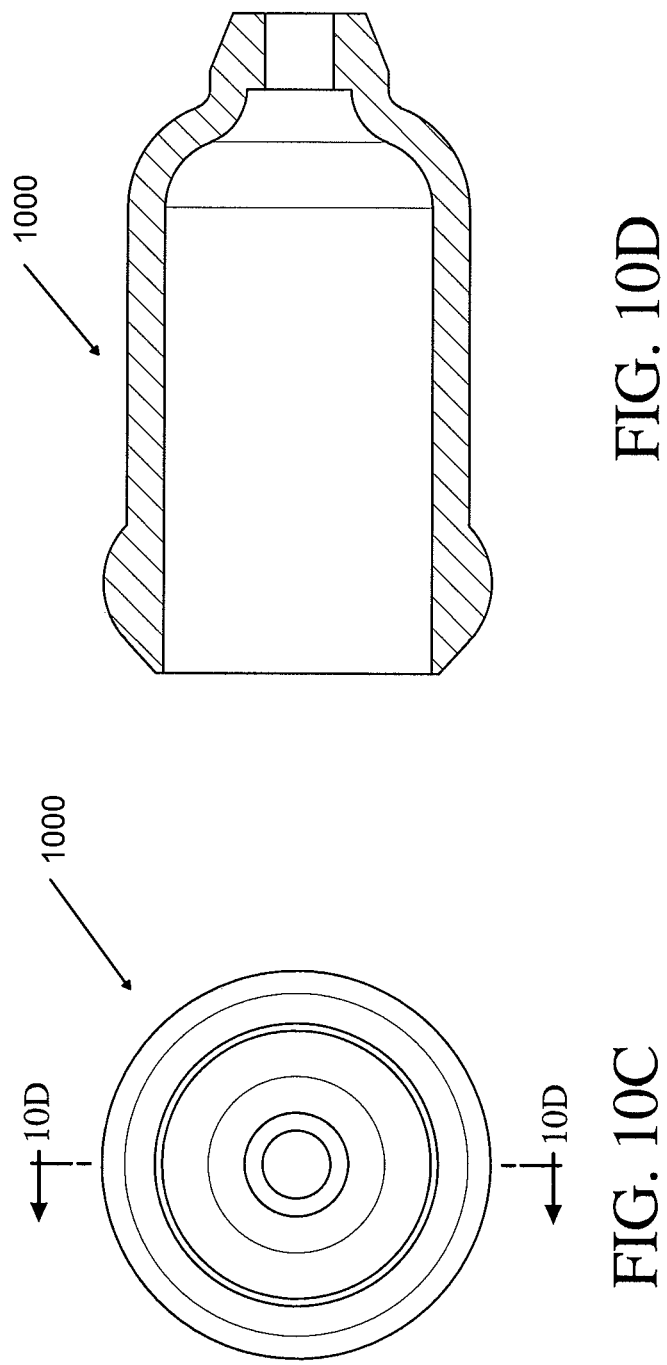

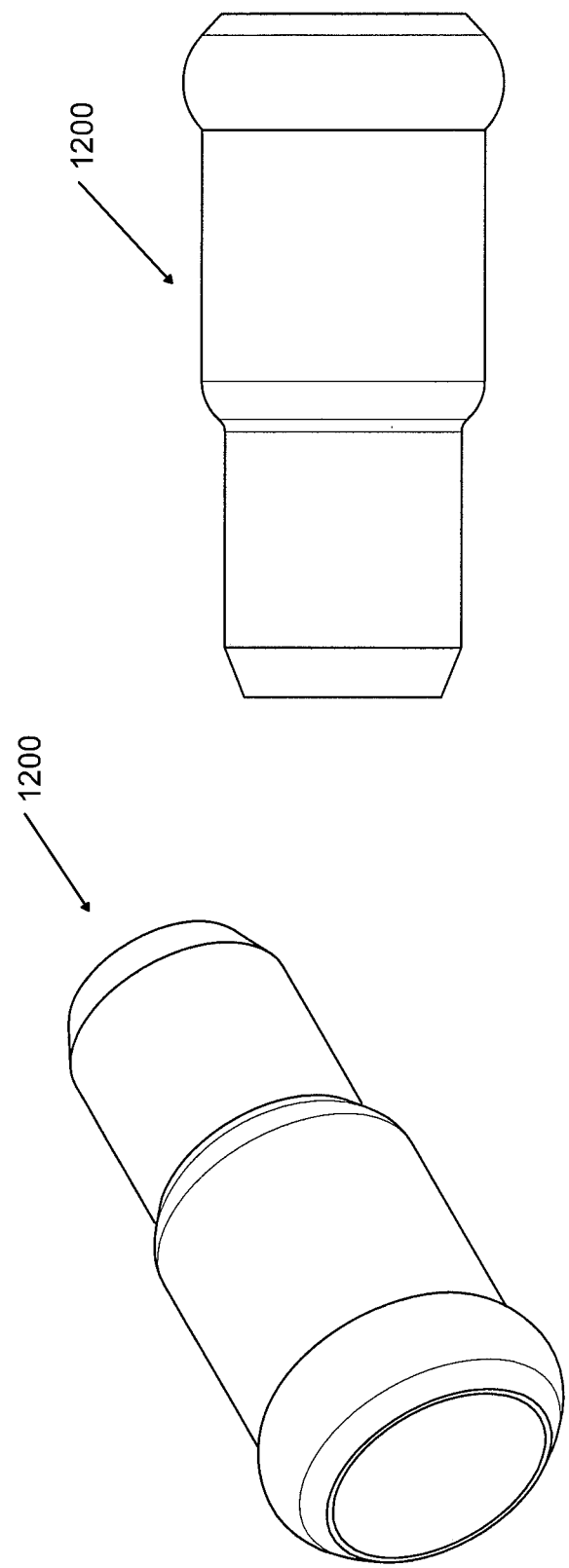

INTRAGASTRIC DEVICE

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 15/690,095, filed Aug. 29, 2017, which is a continuation of U.S. application Ser. No. 14/860,538, filed Sep. 21, 2015, now U.S. Pat. No. 9,827,128, which is a continuation of U.S. application Ser. No. 14/227,195, filed Mar. 27, 2014, now U.S. Pat. No. 9,351,862, which is a continuation of U.S. application Ser. No. 13/510,921, filed on May 18, 2012, now U.S. Pat. No. 8,740,927, which is the national phase under 35 U.S.C. § 371 of prior PCT International Application No. PCT/US2011/022165 which has an International Filing Date of Jan. 21, 2011. Each of the aforementioned applications is incorporated by reference herein in its entirety, and each is hereby expressly made a part of this specification.

FIELD OF THE INVENTION

Devices and methods for treating obesity are provided. More particularly, intragastric devices and methods of fabricating, deploying, inflating, monitoring, and retrieving the same are provided.

BACKGROUND OF THE INVENTION

Obesity is a major health problem in developed countries. Obesity puts you at greater risk of developing high blood pressure, diabetes and many other serious health problems. In the United States, the complications of being overweight or obese are estimated to affect nearly one in three American adults, with an annual medical cost of over $80 billion and, including indirect costs such as lost wages, a total annual economic cost of over $120 billion. Except for rare pathological conditions, weight gain is directly correlated to overeating.

Noninvasive methods for reducing weight include increasing metabolic activity to burn calories and/or reducing caloric intake, either by modifying behavior or with pharmacological intervention to reduce the desire to eat. Other methods include surgery to reduce the stomach's volume, banding to limit the size of the stoma, and intragastric devices that reduce the desire to eat by occupying space in the stomach.

Intragastric volume-occupying devices provide the patient a feeling of satiety after having eaten only small amounts of food. Thus, the caloric intake is diminished while the person is satisfied with a feeling of fullness. Currently available volume-occupying devices have many shortcomings. For example, complex gastric procedures are required to insert some devices.

U.S. Pat. No. 4,133,315, the contents of which are incorporated herein by reference in their entirety, discloses an apparatus for reducing obesity comprising an inflatable, elastomeric bag and tube combination. The bag can be inserted into the patient's stomach by swallowing. The end of the attached tube distal to the bag remains in the patient's mouth. A second tube is snaked through the nasal cavity and into the patient's mouth. The tube ends located in the patient's mouth are connected to form a continuous tube for fluid communication through the patient's nose to the bag. Alternatively, the bag can be implanted by a gastric procedure. The bag is inflated through the tube to a desired degree before the patient eats so that the desire for food is reduced. After the patient has eaten, the bag is deflated. The tube extends out of the patient's nose or abdominal cavity throughout the course of treatment.

U.S. Pat. Nos. 5,259,399, 5,234,454 and 6,454,785, the contents of which are incorporated herein by reference in their entirety, disclose intragastric volume-occupying devices for weight control that must be implanted surgically.

U.S. Pat. Nos. 4,416,267, 4,485,805, 4,607,618, 4,694,827, 4,723,547, 4,739,758, and 4,899,747 and European Patent No. 246,999, the contents of which are incorporated herein by reference in their entirety, relate to intragastric, volume-occupying devices for weight control that can be inserted endoscopically. Of these, U.S. Pat. Nos. 4,416,267, 4,694,827, 4,739,758 and 4,899,747, the contents of which are incorporated herein by reference in their entirety relate to balloons whose surface is contoured in a certain way to achieve a desired end. In U.S. Pat. Nos. 4,416,267 and 4,694,827, the contents of which are incorporated herein by reference in their entirety, the balloon is torus-shaped with a flared central opening to facilitate passage of solids and liquids through the stomach cavity. The balloon of U.S. Pat. No. 4,694,827, the contents of which are incorporated herein by reference in their entirety, has a plurality of smooth-surfaced convex protrusions. The protrusions reduce the amount of surface area which contacts the stomach wall, thereby reducing the deleterious effects resulting from excessive contact with the gastric mucosa. The protrusions also define channels between the balloon and stomach wall through which solids and liquids may pass. The balloon of U.S. Pat. No. 4,739,758, the contents of which are incorporated herein by reference in their entirety, has blisters on its periphery that prevent it from seating tightly against the cardia or pylorus.

The balloons of U.S. Pat. Nos. 4,899,747 and 4,694,827, the contents of which are incorporated herein by reference in their entirety, are inserted by pushing the deflated balloon and releasably attached tubing down a gastric tube. U.S. Pat. No. 4,723,547, the contents of which are incorporated herein by reference in their entirety discloses a specially adapted insertion catheter for positioning its balloon. In U.S. Pat. No. 4,739,758, the contents of which are incorporated herein by reference in their entirety, the filler tube effects insertion of the balloon. In U.S. Pat. No. 4,485,805, the contents of which are incorporated herein by reference in their entirety, the balloon is inserted into a finger cot that is attached by string to the end of a conventional gastric tube that is inserted down the patient's throat. The balloon of European Patent No. 246,999 is inserted using a gastroscope with integral forceps.

In U.S. Pat. Nos. 4,416,267, 4,485,805, 4,694,827, 4,739,758, and 4,899,747 and European Patent No. 246,999, the contents of which are incorporated herein by reference in their entirety, the balloon is inflated with a fluid from a tube extending down from the patient's mouth. In these patents, the balloon also is provided with a self-sealing hole (U.S. Pat. No. 4,694,827, the contents of which are incorporated herein by reference in their entirety), injection site (U.S. Pat. Nos. 4,416,267 and 4,899,747, the contents of which are incorporated herein by reference in their entirety), self-sealing fill valve (U.S. Pat. No. 4,485,805, the contents of which are incorporated herein by reference in their entirety), self-closing valve (European Patent No. 246,999, the contents of which are incorporated herein by reference in their entirety) or duck-billed valve (U.S. Pat. No. 4,739,758, the contents of which are incorporated herein by reference in their entirety). U.S. Pat. No. 4,723,547, the contents of which are incorporated herein by reference in their entirety, uses an elongated thick plug and the balloon is filled by inserting a needle attached to an air source through the plug.

U.S. Pat. No. 4,607,618, the contents of which are incorporated herein by reference in their entirety, describes a collapsible appliance formed of semi-rigid skeleton members joined to form a collapsible hollow structure. The appliance is not inflatable. It is endoscopically inserted into the stomach using an especially adapted bougie having an ejector rod to release the collapsed appliance. Once released, the appliance returns to its greater relaxed size and shape.

U.S. Pat. No. 5,129,915, the contents of which are incorporated herein by reference in their entirety, the contents of which are incorporated herein by reference, relates to an intragastric balloon that is intended to be swallowed and that inflates automatically under the effect of temperature. Three ways that an intragastric balloon might be inflated by a change in temperature are discussed. A composition comprising a solid acid and non-toxic carbonate or bicarbonate is separated from water by a coating of chocolate, cocoa paste or cocoa butter that melts at body temperature. Alternatively, citric acid and an alkaline bicarbonate coated with non-toxic vegetable or animal fat melting at body temperature and which placed in the presence of water, can produce the same result. Lastly, the solid acid and non-toxic carbonate or bicarbonate are isolated from water by an isolation pouch of low-strength synthetic material which it will suffice to break immediately before swallowing the bladder. Breaking the isolation pouches causes the acid, carbonate or bicarbonate and water to mix and the balloon to begin to expand immediately. A drawback of thermal triggering of inflation is that it does not afford the degree of control and reproducibility of the timing of inflation that is desirable and necessary in a safe self-inflating intragastric balloon.

SUMMARY OF THE INVENTION

A free-floating, intragastric, volume-occupying device that can be inserted into the stomach by the patient swallowing it and letting peristalsis deliver it into the stomach in the same manner that food is delivered, or by positioning it with a catheter, is desirable.

Volume-occupying devices and methods for manufacturing, deploying, inflating, tracking, deflating and retrieving of such devices are provided. The devices and methods of the preferred embodiments may be employed for treating over weight and obese individuals. Methods employing the device of the preferred embodiments may be swallowed by a patient, with or without a catheter attached. Once in the stomach of the patient, the device is inflated with a preselected gas or mixture of gases, to a preselected volume. After a predetermined time period, the device can be removed using endoscopic tools or decreases in volume or deflate so as to pass through the remainder of the patient's digestive tract.

Inflation may be achieved by use of a removable catheter that initially remains in fluid contact with the device after it has been swallowed by the patient.

The volume-occupying subcomponent of devices may be formed by injection, blow or rotational molding of a flexible, gas-impermeable, biocompatible material, such as, for example, polyurethane, nylon or polyethylene terephthalate. Materials that may be used to control the gas permeability/impermeability of the volume-occupying subcomponent include, but are not limited to, silicon oxide (SiOx), gold or any noble metal, saran, conformal coatings and the like, when it is desired to reduce permeability. To enhance gas-impermeable characteristics of the wall of the device, if desirable, the volume-occupying subcomponent may be further coated with one or more gas-barrier compounds, or be formed of a Mylar polyester film coating or kelvalite, silver or aluminum as a metallized surface to provide a gas impermeable barrier.

In further embodiments, the device employs a delivery state in which the device is packaged such that the device may be swallowed while producing minimal discomfort to the patient. In a delivery state, the device may be packaged into a capsule. Alternatively, the device may be coated with a material operable to confine the device and facilitate swallowing. Various techniques may also be employed to ease swallowing of the device including, for example, wetting, temperature treating, lubricating, and treating with pharmaceuticals such as anesthetics.

In other embodiments, the devices may incorporate a tracking or visualization component that enables physicians to determine the location and/or orientation of the device within the patient's body. Tracking subcomponents may include incorporating a barium stripe or geometric shape into the wall of the volume-occupying subcomponent. Tracking and visualization, may also be achieved by incorporation of a microchip, infrared LED tag, ultraviolet absorbing compounds, fluorescent or colored compounds and incorporation of metallized strips and patterns into the volume-occupying subcomponent or other subcomponents of the device. Such techniques may also be used to obtain certain device specific information and specifications while the device remains inside the patient's body.

In a first aspect, a system is provided for inflating an intragastric balloon, the system comprising: an inflation catheter, wherein the inflation catheter comprises a needle assembly comprising a hollow needle, a bell-shaped needle sleeve, and a mechanism for detachment of the inflation catheter after inflation of a balloon in vivo is complete; an intragastric balloon comprising a polymeric wall, wherein the polymeric wall comprises one or more layers, and a balloon valve system comprising a self-sealing septum in a retaining structure, wherein the septum is configured for piercing by the needle, wherein the retaining structure comprises a concentric valve system with a smaller inner cylinder housing the septum and a larger outer cylinder housing a material providing compressive forces against the bell-shaped needle sleeve of the inflation catheter for inflation and detachment, wherein the material providing compressive forces is a harder durometer material than the septum, and wherein the smaller inner cylinder comprises a lip configured for an interference fit with the bell-shaped needle sleeve to provide sealing of the valve to the inflation catheter sufficient to maintain the seal during inflation of the balloon; a balloon outer container; and an inflation source container, wherein the inflation source container is configured to connect to the inflation catheter; wherein the inflation catheter connected to the intragastric balloon prior to inflation is of a size and shape configured for swallowing by a patient in need thereof.

In an embodiment of the first aspect, the polymeric wall comprises a barrier material comprising of nylon/polyethylene.

In an embodiment of the first aspect, the polymeric wall comprises a barrier material comprising of nylon/polyvinylidene chloride/polyethylene.

In an embodiment of the first aspect, the outer container is selected from the group consisting of a push-fit capsule, a wrap, and a band, and wherein the outer container comprises a material selected from the group consisting of gelatin, cellulose, and collagen.

In an embodiment of the first aspect, the septum is cone-shaped.

In an embodiment of the first aspect, the inflation source container is configured to connect to the inflation catheter via a connector or an inflation valve.

In an embodiment of the first aspect, the inflation catheter is from 1 French to 6 French in diameter, and is from about 50 cm to about 60 cm in length.

In an embodiment of the first aspect, the inflation catheter is a dual lumen catheter comprising an inflation lumen and a detachment lumen, wherein the inflation lumen is in fluid connection to the inflation source container, and wherein the detachment lumen is configured for connection to a detachment liquid source container, wherein the detachment liquid comprises a physiological compatible liquid, and wherein the interference fit is insufficient to maintain a seal upon application of a hydraulic pressure by the detachment liquid, such that upon application of the hydraulic pressure to the needle assembly it is ejected from the balloon valve.

In an embodiment of the first aspect, the inflation catheter comprises a single lumen and a structural member providing increased tensile strength, and an inflation valve configured for connecting the single lumen to the inflation source container and a detachment liquid source container, wherein the detachment liquid comprises a physiological compatible liquid, and wherein the interference fit is insufficient to maintain a seal upon application of a hydraulic pressure by the detachment liquid, such that upon application of the hydraulic pressure to the needle assembly it is ejected from the balloon valve.

In an embodiment of the first aspect, the inner cylinder is configured to control alignment of the needle assembly with the septum, provide a barrier to the needle piercing the polymeric wall, and provide compression such that the septum reseals after inflation and needle withdrawal.

In an embodiment of the first aspect, a plurality of intragastric balloons is connected to a single inflation catheter.

In an embodiment of the first aspect, the inflation catheter is of a variable stiffness.

In an embodiment of the first aspect, the inflation source comprises a syringe.

In an embodiment of the first aspect, the inflation source is configured to utilize information regarding inflation pressure as a function of time to provide feedback to a user, wherein the feedback indicates a condition selected from the group consisting of failure by mechanical blockage, failure by esophagus constraint, failure by inflation catheter leak or detachment, and successful balloon inflation.

In a second aspect, a method is provided for inflating an intragastric balloon, the method comprising: providing an intragastric balloon in an outer container, the intragastric balloon comprising a polymeric wall, wherein the polymeric wall comprises one or more layers, and a balloon valve system comprising a self-sealing septum in a retaining structure, wherein the retaining structure comprises a concentric valve system with a smaller inner cylinder housing the septum and a larger outer cylinder housing a material configured to provide compressive forces against a bell-shaped needle sleeve of an inflation catheter, wherein the material providing compressive forces is a higher durometer material than the septum, and wherein the smaller inner cylinder comprises a lip configured for an interference fit with the bell-shaped needle sleeve; providing an inflation catheter comprising a needle assembly, the needle assembly comprising a hollow needle, a bell-shaped needle sleeve; piercing the septum by the needle of an inflation catheter, whereby an interference fit is created between the bell-shaped needle sleeve and the lip of the smaller inner cylinder; causing the intragastric balloon in an outer container attached by the interference fit to the inflation catheter to be swallowed by a patient in need thereof; degrading the outer container so as to permit inflation of the intragastric balloon; inflating the intragastric balloon in the patient's stomach via the inflation catheter, wherein the inflation catheter is connected to an inflation fluid source container; and detaching the intragastric balloon from the inflation catheter, wherein a detachment liquid comprising a physiological compatible liquid is forced through the inflation catheter to apply hydraulic pressure to the needle assembly such that the interference fit between the lip and the bell-shaped needle sleeve is broken, the needle assembly is ejected from the balloon valve and the self-sealing septum reseals.

In an embodiment of the second aspect, the inflation catheter is a dual lumen catheter comprising an inflation lumen and a detachment lumen, wherein the inflation lumen is configured for fluid connection to the inflation source container, and wherein the detachment lumen is configured for connection to a detachment liquid source container for detachment of the balloon.

In an embodiment of the second aspect, the inflation catheter is a single lumen catheter comprising a structural member providing increased tensile strength and an inflation valve configured for first connecting the single lumen catheter to the inflation source container and then to a detachment liquid source container for detachment of the balloon.

In an embodiment of the second aspect, wherein the method further comprises monitoring inflation pressure as a function of time and detaching when a predetermined ending pressure is obtained, wherein successful balloon inflation is indicated by achievement of the preselected ending pressure, which is based on a starting pressure in the inflation source and an inflation volume of the balloon.

In a third aspect, a method is provided for deflating an intragastric balloon, the method comprising: providing an intragastric balloon in an in vivo intragastric environment, the intragastric balloon comprising a polymeric wall and a valve system, the valve system comprising a self-sealing valve, a casing, an outer sealing member, a rigid retaining structure, and a deflation component; wherein the casing has one or more vent pathways and a lip configured to hold the outer sealing member in place, wherein the outer sealing member is positioned to block the one or more vent pathways when in place, wherein the rigid retaining structure provides support to the septum and the outer sealing member, and wherein the deflation component is situated in the casing and behind the retaining structure; exposing the deflation component to moisture inside of the balloon via the one or more vent pathways, whereby the deflation component expands, pushing the retaining structure and thus the outer sealing member linearly past the lip of the casing to open the one or more vent pathways so as to provide fluid communication between the in vivo gastric environment and a lumen of the balloon; and deflating the balloon through the one or more vent pathways.

In an embodiment of the third aspect, the deflation component comprises a solute material encapsulated in a binder material, wherein the deflation component is further surrounded by moisture limiting material that has a predefined moisture vapor transmission rate.

In an embodiment of the third aspect, the solute material is a polyacrylamide.

In an embodiment of the third aspect, the rigid retaining structure and the casing has a press fit lock that prevents the rigid retaining structure from being expelled from the casing after maximum displacement by the deflation component.

In a fourth aspect, a method is provided for deflating an intragastric balloon, the method comprising: providing an intragastric balloon in an in vivo intragastric environment, the intragastric balloon comprising a polymeric wall, a self-sealing valve system, and a deflation system, the deflation system comprising a casing, a sealing member, a plunger, and a deflation component; wherein the casing has one or more vent pathways and is secured in the polymeric wall, wherein the plunger provides support to the sealing member and maintains the sealing member in position to block the one or more vent pathways in the casing when in place, and wherein the deflation component is situated in the casing and behind the plunger; exposing the deflation component to moisture inside of the balloon via the one or more vent pathways, whereby the deflation component expands, pushing the plunger and thus the sealing member linearly through the casing to open the one or more vent pathways so as to provide fluid communication between the in vivo gastric environment and a lumen of the balloon; and deflating the balloon through the one or more vent pathways.

In an embodiment of the fourth aspect, the intragastric balloon further comprises a water retaining material situated between the deflation component and the one or more vent pathways, wherein the water retaining material is configured to retain water and to hold it against a surface of the deflation component in order to maintain a constant moisture environment.

BRIEF DESCRIPTION OF THE DRAWINGS

FIGS. 5A-C depict a perspective view (FIG. 5A), a side view (FIG. 5B), and a top view (FIG. 5C) a ring retainer 112—an additional retaining ring 112 to further enhance the seal between the metal and the valve silicone, as in the self sealing valve system 100 of FIGS. 1A-D.

FIG. 8A depicts the valve 830 coupled to the inflation catheter 820, and FIG. 8B depicts the valve 830 further coupled to the encased balloon (not depicted) via the inflation catheter connector 840. The inflation catheter can be a dual lumen catheter including an inflation lumen 821 and a detachment lumen 822.

FIGS. 10A-D depict a perspective view (FIG. 10A), a side view (FIG. 10B), a top view (FIG. 10C), and a cross-sectional view (FIG. 10C) of a bell-shaped needle sleeve 1000.

FIG. 11A depicts the single lumen catheter with bell-shaped needle sleeve 1000 protecting the hollow needle 1100. FIG. 11B shows a perspective cross-sectional view of the single lumen catheter showing detail of the needle 1100, bell-shaped needle sleeve 1000, and tensile cord 1120 as a structural member providing increased tensile strength. FIG. 11C shows a perspective cross-sectional view of the single lumen catheter 1110 showing additional detail of the needle 1100 and bell-shaped needle sleeve 1000 when seated in the head unit 110 of the self-sealing valve system 100 of FIGS. 1A-D.

FIGS. 12A-D depict a perspective view (FIG. 12A), a side view (FIG. 12B), a top view (FIG. 12C), and a cross-sectional view (FIG. 12C) of a needle sleeve 1200 configured to accommodate a larger diameter tube.

FIGS. 5A-C depict a perspective view (FIG. 5A), a side view (FIG. 5B), and a top view (FIG. 5C) a ring retainer 112—an additional retaining ring 112 to further enhance the seal between the metal and the valve silicone, as in the self sealing valve system 100 of FIGS. 1A-D.

FIG. 8A depicts the valve 830 coupled to the inflation catheter 820, and FIG. 8B depicts the valve 830 further coupled to the encased balloon (not depicted) via the inflation catheter connector 840. The inflation catheter can be a dual lumen catheter including an inflation lumen 821 and a detachment lumen 822.

FIGS. 10A-D depict a perspective view (FIG. 10A), a side view (FIG. 10B), a top view (FIG. 10C), and a cross-sectional view (FIG. 10C) of a bell-shaped needle sleeve 1000.

FIG. 11A depicts the single lumen catheter with bell-shaped needle sleeve 1000 protecting the hollow needle 1100. FIG. 11B shows a perspective cross-sectional view of the single lumen catheter showing detail of the needle 1100, bell-shaped needle sleeve 1000, and tensile cord 1120 as a structural member providing increased tensile strength. FIG. 11C shows a perspective cross-sectional view of the single lumen catheter 1110 showing additional detail of the needle 1100 and bell-shaped needle sleeve 1000 when seated in the head unit 110 of the self-sealing valve system 100 of FIGS. 1A-D.

FIGS. 12A-D depict a perspective view (FIG. 12A), a side view (FIG. 12B), a top view (FIG. 12C), and a cross-sectional view (FIG. 12C) of a needle sleeve 1200 configured to accommodate a larger diameter tube.

FIG. 19A (perspective view) and FIG. 19B (side view) depict an eroding core 1910 with a protective barrier 1930 between the core and the intragastric environment 1950, held in place by a housing 1920. In another embodiment, a compressed radial seal 1960' is held in place against the housing by an erodible core 1965 with a protective barrier 1975 (FIG. 19C). After the core erodes (FIG. 19D), the radial seal 1960", now uncompressed, is released from against the housing 1970.

FIG. 22A depicts a compressed view of the compressed pellet or gas releasing pellet 2218' and FIG. 22B depicts an expanded view of the compressed pellet or gas releasing pellet 2218". The mechanism further includes an eroding plug 2210" after expansion of the compressed pellet or gas releasing pellet 2218', a water restricting membrane 2216, and a solid casing 2214.

FIG. 27A depicts a cross-section of the mechanism with the seal blocking the vents 2790, 2792. The mechanism includes a silicon head 2780, catheter needle sleeve 2700, needle 2710, compression seal 2770, septum 2760, press fit 2750, casing 2740, expanding device 2730, insert 2720, and balloon film 2712. FIG. 27B depicts a cross section of the mechanism with the seal displaced, enabling fluid communication through the vent. An iso image of the mechanism with the seal displaced, enabling fluid communication through the vent is provided in FIG. 27C. An iso image of the mechanism positioned for inflation of the balloon is provided in FIG. 27D.

FIG. 28A depicts a cross-section of the deflation mechanism 2800' with the seal 2860' blocking the vents 2850', with the expanding device in a contracted state 2830'. FIG. 28B depicts a cross section of the deflation mechanism 2800" with the seal 2860" displaced by expansion of the expanding device into an expanded state 2830", enabling fluid communication through the vent 2850". An iso image of the mechanism 2800' with the seal 2860' blocking the vents 2850' is provided in FIG. 28C. An iso image of the mechanism 2800" with the seal 2860" displaced, enabling fluid communication through the vent 2850", is provided in FIG. 28D.

DETAILED DESCRIPTION OF THE PREFERRED EMBODIMENT

Figure 1B:
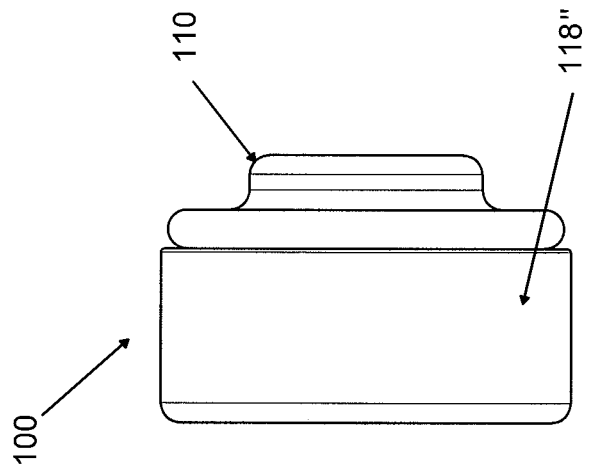
FIGS. 1A-D depict a perspective view (FIG. 1A), a side view (FIG. 1B), a top view (FIG. 1C) and a cross-sectional view (FIG. 1D) of a head assembly of a self-sealing balloon valve system 100 which contains a self-sealing septum (plug) 114 housed within a metallic concentric cylinder. The self sealing balloon valve system includes retaining rings 112, a ring stop 116, and a tube septum 118. The retaining structure includes tube septum 118, which includes a portion that is a larger outer cylinder 118" and a portion that is a smaller inner cylinder 118', the inner cylinder 118' housing the septum 114 and the larger outer cylinder 118" housing the head unit 110, which is made of a material configured to provide compressive forces against a bell-shaped needle sleeve (not depicted). The inner cylinder 118' of the tube septum 118 includes a lip 118' configured for an interference lip with a bell-shaped needle sleeve (not depicted). The entire outer cylinder 118" is filled with a material forming the head unit 110, and a small circular lip 111 of this same material is provided that is slightly larger than the diameter of the inner cylinder 118' and extends to the outside surface of the balloon (not depicted).
Figure 1A:
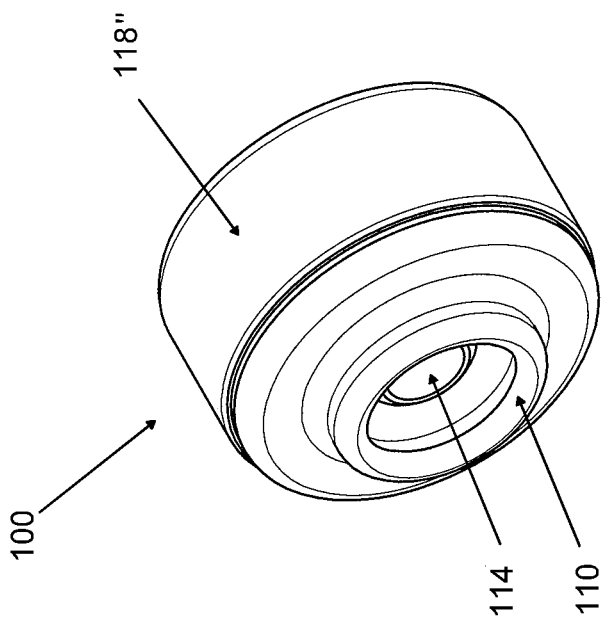
Figure 1D:
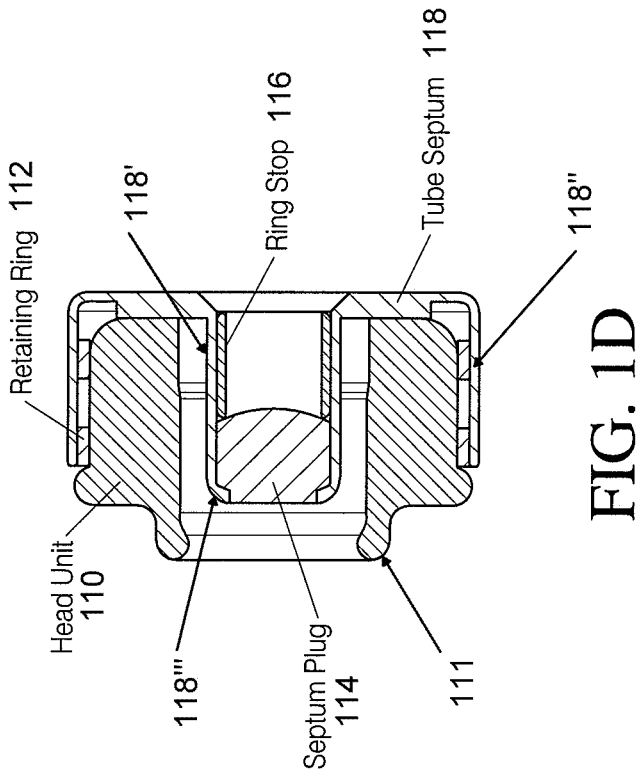
Figure 1C:
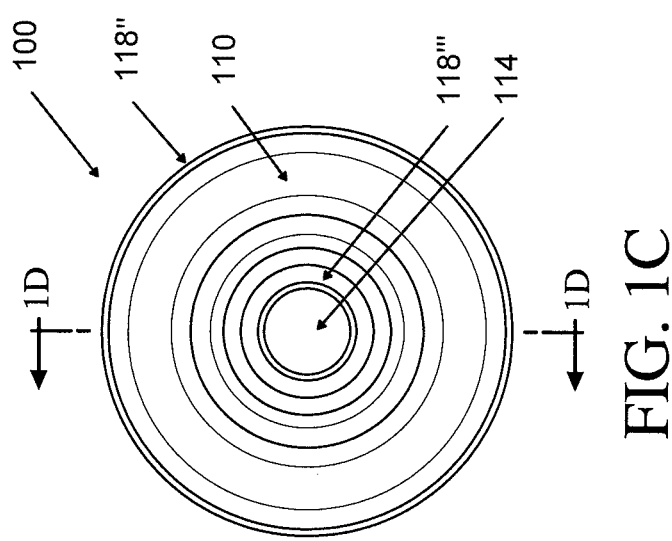
Figure 2B:
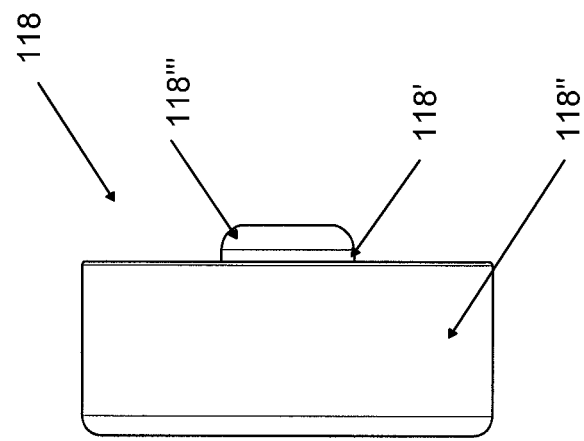
FIGS. 2A-D depict a perspective view (FIG. 2A), a side view (FIG. 2B), a cross-sectional view (FIG. 2C), and a top view (FIG. 2C) of tube septum 118. It includes a smaller inner cylinder 118' of a concentric metallic retaining structure into which a septum can be inserted or otherwise fabricated into, as in the self sealing valve system 100 of FIGS. 1A-D.
Figure 2A:
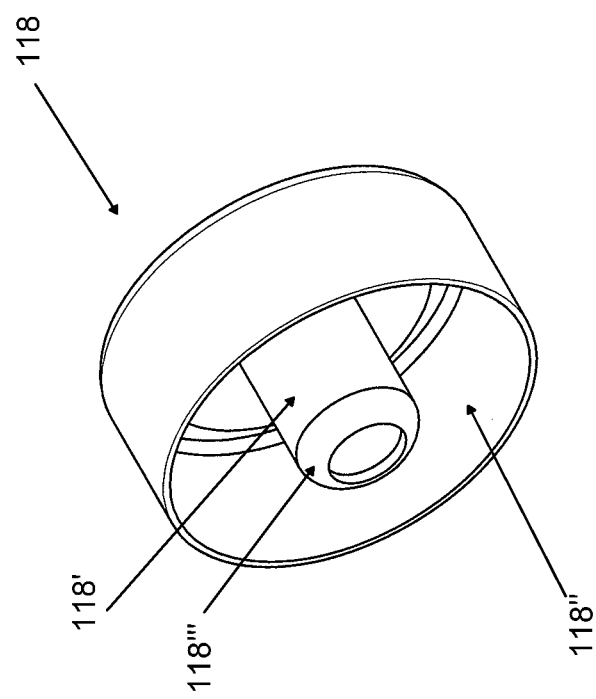
Figure 2D:
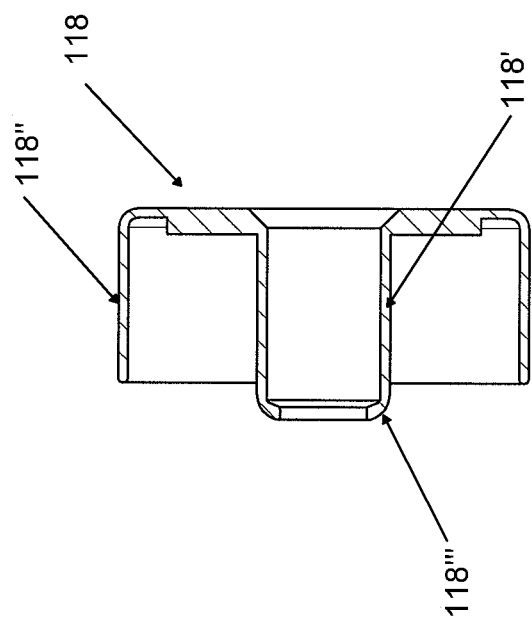
Figure 2C:
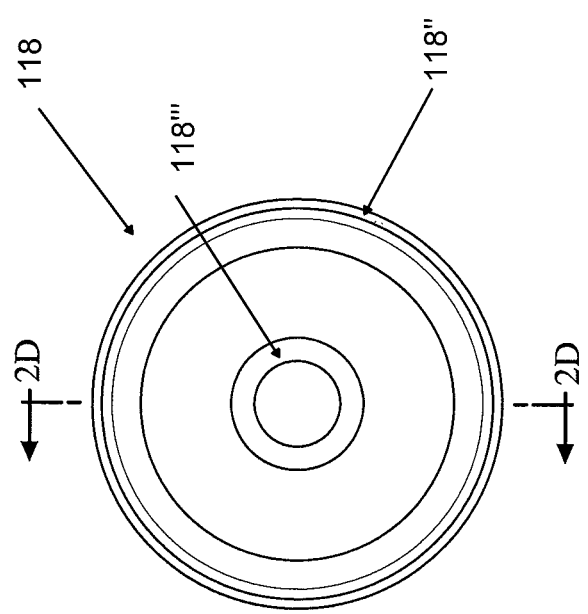

The following description and examples illustrate a preferred embodiment of the present invention in detail. Those of skill in the art will recognize that there are numerous variations and modifications of this invention that are encompassed by its scope. Accordingly, the description of a preferred embodiment should not be deemed to limit the scope of the present invention.

The term "degradable" as used herein is a broad term, and is to be given its ordinary and customary meaning to a person of ordinary skill in the art (and is not to be limited to a special or customized meaning), and refers without limitation to a process by which structural integrity of the balloon is compromised (e.g., by chemical, mechanical, or other means (e.g., light, radiation, heat, etc.) such that deflation occurs. The degradation process can include erosion, dissolution, separation, digestion, disintegration, delamination, comminution, and other such processes.

The term "swallowable" as used herein is a broad term, and is to be given its ordinary and customary meaning to a person of ordinary skill in the art (and is not to be limited to a special or customized meaning), and refers without limitation to ingestion of a balloon by a patient such that the outer capsule and its constituents are delivered to the stomach via normal peristalsis movement. While the systems of preferred embodiments are swallowable, they are also configured by ingestion by methods other than swallowing. The swallowability of the system is derived, at least in part, by the outer container size for the self-inflating system and the catheter and outer container size for the manual inflation system. For the self-inflating system, the outer capsule is sufficient to contain the inner container and its constituents, an amount of activation agent injected prior to administration, the balloon size and the balloon material thickness. The system is preferably of a size less than the average normal esophagus diameter.

Described herein is an orally ingestible device. In preferred embodiments, the device is able to traverse the alimentary canal. The device may be useful, for example, as an intragastric volume-occupying device. The device overcomes one or more of the above-described problems and shortcomings found in current intragastric volume-occupying devices.

In order to more clearly describe the subject matter of the preferred embodiments, different embodiments of the same subcomponent will be described under a single relevantly-titled subheading. This organization is not intended to limit the manner in which embodiments of different subcomponents may be combined in accordance with the present invention.

Swallowable Intragastric Balloon System

A swallowable, self-inflating or inflatable intragastric balloon system according to selected preferred embodiments includes the following components: self-sealing valve system for addition of fluid to the lumen of the balloon or to the inner container ("valve system"), a balloon in a deflated and compacted state ("balloon") and an outer capsule, container, or coating ("outer container") that contains the balloon. For self-inflating balloons, an inner capsule or other container ("inner container") that contains one or more $CO_2$ generating components is present inside the lumen of the balloon. For inflatable balloons, an inflation fluid source, a catheter and tubing ("inflation assembly") are provided for inflating the balloon after ingestion or placement in the stomach. In the self-inflating balloon configuration, the valve is preferably attached to the inner surface of the balloon by an adhesive or other means (e.g., welding), and provided with an inoculation spacer to prevent puncture of the wall of the balloon and inner container by a needle or other means for injecting an liquid activation agent into the lumen of the balloon via the self-sealing valve. A valve providing releasable attachment of the tubing to the balloon is provided in the inflatable balloon configuration. Preferably, the self-sealing valve system attached to the balloon (e.g., on its inside surface) in the inflatable configuration is "universal" or compatible with a swallowable catheter or a physician-assisted catheter. The valve system serves to allow for balloon inflation using a miniature catheter that includes a needle assembly and also provides a mechanism for detachment of the catheter after inflation has been completed.

The outer container preferably incorporates the balloon in a compacted state (e.g., folded and rolled), preferably with sufficient space to allow for activation liquid to be injected into the balloon in the self-inflating balloon configuration, wherein the liquid activation agent initiates separation, erosion, degradation, and/or dissolution of the inner container and generation of $CO_2$ upon contact with the inflation agent contained within the inner container, which subsequently causes outer container separation, erosion, degradation, and/or dissolution due to $CO_2$ gas pressure. In the inflatable balloon configuration, the outer container need only incorporate the balloon in a compacted state.

Selected components of a swallowable intragastric balloon system of a preferred embodiment can include a silicone head with radiopacity ring, trimmed 30 D silicone septum, Nylon 6 inoculation spacer, compacted balloon, inner container (if self-inflating), and outer container as constituents of the system in unassembled form. A fully assembled outer container can include a vent hole aligned with a septum for puncture to inject liquid activation agent (if self-inflating) or a port for connection of tubing (if inflatable). As discussed further below, the components of particularly preferred systems possess the attributes described herein; however, in certain embodiments systems can be employed which utilize components having other attributes and/or values.

Devices according to the preferred embodiments are intended for ingestion by a patient and deployment without the need to resort to invasive methods. It is therefore desirable that the device of the preferred embodiments be operable to conform to a compact delivery state which can be swallowed by a patient with minimal discomfort. Once in the stomach, it is desirable for the device to assume a substantially larger deployed state. In order to achieve the transition from a delivery state to a deployed state the device is subjected to inflation.

Inner Container

In order to initiate inflation in the self-inflating configuration, the inflation subcomponent may require outside inputs such as an activation agent. The activation agent is preferably injected using a syringe having a needle with a gauge diameter of from 25 to 32. The needle length is preferably from about 0.25 inches (0.6 cm) to 1 inches (2.54 cm) in length so as to create a flow rate that allows for delivery of the full volume of inflation agent within 30 seconds, but in a manner/stream/flow that does not physically damage the inner container, thereby causing premature $CO_2$ generation and inflation. The activation agent is preferably pure water, or a solution containing up to 50% concentration of anhydrous citric acid at 20° C., or the equivalent thereof at varying solution temperatures based on solubility of anhydrous citric acid. Preferably, the system is configured to have an occupyable void space in the central lumen of the balloon when in compacted form in the outer container of from about 0.3 ml to about 4.5 ml, such that a corresponding volume of activation agent can be injected into the void space.

In one embodiment, prior to folding, the free-floating inner container with inflation agent for $CO_2$ generation is preferably vertically aligned with the self-sealing valve system such that the septum/inoculation spacer is placed directly above the tip of the capsule. The balloon contains an inner container. A self-sealing valve system is adhesively adhered to the interior of the wall of the balloon, and the inverted configuration of the balloon is provided by inversion through a hole sealed with a patch. The top approximate ¼ of the balloon wall is folded over the inner capsule, and the pleats where the capsule is creased are similar to the pleats formed in the second step of making a paper airplane, then folded over to the left or to the right. The bottom approximate ¾ of the sphere is then accordioned using no more than 2 creases and folded over the capsule. The left half is then folded over the right half of the capsule or vice versa so that the wings touch. Then the material is rolled over until it creates a tight roll. The device is then placed inside the outer container.

In a self-inflating configuration, the balloon is folded so as to form a pocket around the inner capsule, to insure that the liquid injected through the self-sealing valve system is contained in an area less than 10% of the entire balloon surface area. It is not necessary to provide a pocket in the inflatable configuration, as no inner capsule is provided. The balloon is folded such that the number of total folds is minimized so as to minimize possible damage to the outer material or compromise of barrier properties. The number of total folds is preferably less than 10 folds. The balloon material is rolled when at all possible such that the number of creases required to fit the balloon in an outer container is minimized. This is done in effort to also to prevent lumen material damage. The self-sealing valve is also preferably constructed off-center of the balloon so as to minimize the number of folds that layer on top of each other.

In the self-inflating configuration, the material forming the wall of the balloon is processed and folded to maximize reaction efficiency by localizing the initiation agent injected into the balloon so that it is maintained proximal to the reactants within the inner container. The balloon is folded such that once the reaction initiates and the outer container separates, the balloon unfolds in a manner that creates the largest possible surface area, which prohibits the balloon from readily passing through the pyloric sphincter. The ratio of reactants in the inflation agent and activation agent are selected such that the pH of any remnant liquid inside the lumen of the balloon is acidic, with a pH of less than 6, such that any balloon leakage or breach that allows stomach acid to enter does not cause additional $CO_2$ generation and resulting unintentional re-inflation.

In a self-inflating configuration, an inflation agent is compressed, formed or otherwise held in a shape which provides good surface area availability for the reactants for $CO_2$ generation, while minimizing the space and/or volume sufficient to hold the inner container. Preferably, the inner container has a length (longest dimension) of from about 0.748 inches (1.9 cm) to 1.06 inches (2.7 cm) and a diameter or width of from about 0.239 inches (0.6 cm) to about 0.376 inches (1 cm). The volume of the inner container is preferably from about 0.41 ml to about 1.37 ml. The inner container is preferably in the form of a standard push-fit gelatin capsule but a gelatin tape may be used in lieu of a push-fit capsule. The container is preferably relied upon for containing the inflation agent; however, additional sealing or other encapsulation can be employed to control timing of inflation. Gelatin is particularly preferred for use as the inner container; however other materials can also be suitable for use, e.g., cellulose. In order to minimize the internal volume of the system, it is generally preferred to include only a single inner container; however, in certain embodiments two or more internal containers can advantageously be employed. Timing of self-inflation is selected based on a normal esophageal transit time and a normal time of gastric emptying of large food particles, such that the balloon does not inflate to a size that can block the esophageal passageway or prematurely pass through the pyloric sphincter. Timing is also controlled by compacting the balloon such that the activation agent is substantially localized in the balloon next to the inner capsule, creating an efficient $CO_2$ self-inflation method. Balloon inflation is initiated by the liquid activation agent causing degradation of the inner container, such that the inflation agent in the inner container contacts the liquid activation agent, thereby initiating the gas generation reaction.

Inflation Assembly

In certain preferred embodiments, the volume-occupying subcomponent is filled with a fluid using tubing which is subsequently detached and pulled away from the volume-occupying subcomponent. One end of the volume-occupying subcomponent has a port connected to tubing of sufficient length that when unwound can span the entire length of the esophagus, from mouth to stomach. This tubing is connected to the volume-occupying subcomponent with a self-sealable valve or septum that can tear away from the volume-occupying subcomponent and self-seal once the volume-occupying subcomponent is inflated. A physician or other health care professional secures one end of the tubing as the patient swallows the device. Once the device is residing within the stomach, the physician uses the tube to transmit a fluid, such as air, other gas(es), saline solution, pure water, or the like, into the volume-occupying subcomponent and thereby inflate it. After the volume-occupying subcomponent is fully inflated, the tubing is released and can be pulled out from inside the patient.

The tube may be released in a number of manners. For example, the tubing may be detached by applying a gentle force, or tug, on the tubing. Alternatively, the tubing may be detached by actuating a remote release, such as a magnetic or electronic release. Additionally, the tubing may be released from the volume-occupying subcomponent by an automatic ejection mechanism. Such an ejection mechanism may be actuated by the internal pressure of the inflated volume-occupying subcomponent. For example, the ejection mechanism may be sensitive to a specific pressure beyond which it will open so as to release any excess pressure and simultaneously release the tube. This embodiment provides a desirable feature through combining release of the tubing with a safety valve that serves to avert accidental over inflation of the volume-occupying subcomponent in the patient's stomach.

This automatic release embodiment also provides the benefit that the device inflation step may be more closely monitored and controlled. Current technology allows for a self-inflating intragastric volume-occupying subcomponent which generally begins to inflate in a four minute timeframe after injection with an activation agent such as citric acid. In this approach, the volume-occupying subcomponent may, in some instances, begin to inflate prior to residing within the stomach (e.g., in the esophagus), or, in patients with gastric dumping syndrome or rapid gastric emptying, the volume-occupying subcomponent may end up in the small intestine prior to the time that inflation occurs. Accordingly, in certain embodiments it can be desirable to inflate the volume-occupying subcomponent on command, once it is ascertained that the volume-occupying subcomponent is residing in the correct location.

In certain embodiments, it may also be advantageous for the volume-occupying subcomponent to inflate gradually or in several steps over time. For example, if gas escapes the volume-occupying subcomponent prior to the desired deflation time, it can be beneficial for the device to re-inflate in order to preserve it in its expanded state.

Outer Container

The balloon is preferably provided in a deflated and folded state in a capsule or other retaining, containing or coating structure ("outer container"). The outer container is preferably in the form of a standard push-fit gelatin capsule, with the push-fit relied upon for containing the deflated/folded balloon; however, a gelatin wrap can advantageously be employed in certain embodiments. Gelatin is particularly preferred for use as the outer container; however other materials can also be suitable for use, e.g., cellulose, collagen, and the like. Preferably, the outer container has a length (longest dimension) of from about 0.95 inches (2.4 cm) to 2.5 inches (6.3 cm) and a diameter or width of from about 0.35 inches (0.9 cm) to about 0.9 inches (2.4 cm). The volume of the inner container for the self-inflatable version is preferably from about 1.2 ml to about 8.25 ml. In the self-inflating configuration, the outer container is preferably configured with one or more holes, slits, passageways or other egresses, preferably on each end, which can act as vents such that any gas created due to inflation agent exposure to condensation or other ambient moisture present during processing does not cause premature separation or degradation of the inner container prior to 30 seconds after inoculation of the liquid activation agent, which may have an undesirable effect on reaction efficiency. Such egresses can also expedite dissolution of the outer container to prepare the balloon for inflation in the inflatable configuration. The process of the outer capsule degrading (e.g., separates, dissolves, or otherwise opens) is expedited by pressure build up caused by inflation (self-inflation or inflation via catheter) of the balloon. The outer capsule can be dipped in water for a brief time to soften the materials but not release the balloon prior to swallowing to minimize the time lapse between swallowing and balloon inflation. In the inflatable configuration, the outer container is provided with a hole to house the inflation tube needle assembly, wherein the diameter of the catheter needle housing is mechanically compatible with the diameter of the outer container hole such that the needle can be inserted into the self-sealing valve while maintaining therein the housed balloon to facilitate pushing or swallowing of the balloon assembly. In a preferred embodiment, the outer container is a capsule. The distal half of the capsule may be flared to prevent abrasion of the balloon materials by the leading edge of the capsule as the compacted balloon is inserted into the capsule. The capsule can also comprise two parts held together with a gel band and encompassing the folded balloon that allows for quicker separation of the capsule so that inflation can take place more expeditiously. The outer capsule degrades (e.g., separates, dissolves, or otherwise opens) due to contact with ingested fluid ingestion (e.g., water intake) and preferably degrades within 5 minutes or less, more preferably within 2 minutes or less, so as not to cause discomfort to the patient while the balloon/catheter tube is in place.

In a preferred embodiment, the device is fitted into a standard sized gelatin capsule. The capsule may be formed of a material that has a known rate of degradation such that the device will not be released from the capsule or otherwise deployed prior to entry into the stomach. For example, the capsule materials may include one or more polysaccharide and/or one or more polyhydric alcohols.

Alternatively, the device, in its delivery state, may be coated in a substance that confines the device in its delivery state while also facilitating swallowing. The coating may be applied by a dipping, sputtering, vapor deposition, or spraying process which may be conducted at an ambient or positive pressure. The balloon may also be encapsulated by wrapping gelatin tape around the balloon and then placing the wrapped balloon in a capsule, if so desired.

In certain preferred embodiments, the encapsulated or coated device is lubricated or otherwise treated so as to facilitate swallowing. For example, the encapsulated or coated device may be wetted, heated, or cooled, prior to swallowing by the patient. Alternatively, the encapsulated or coated device may be dipped in a viscous substance that will serve to lubricate the device's passage through the esophagus. Examples of possible coatings can be any substances with lubricious and/or hydrophilic properties and include glycerine, polyvinylpyrrolidone (PVP), petroleum jelly, aloe vera, silicon-based materials (e.g. Dow 360) and tetrafluoroethylene (TFE). The coating may also be applied by a sputtering, vapor deposition or spraying process.

In additional embodiments the coating or capsule is impregnated or treated with one or more local anesthetics or analgesics to ease swallowing. Such anesthetics may include anesthetics in the amino amide group, such as articaine, lidocaine and trimecaine, and anesthetics in the amino ester group, such as benzocaine, procaine and tetracaine. Such analgesics may include chloraseptic.

In certain embodiments, the capsule may be weighted at a certain end in order for it to be oriented appropriately when it is administered, as it travels down the esophagus, and/or when it is in the stomach. The weighting components may include polymer materials or inflation reactants.

The swallowable, self-inflating intragastric balloon is provided with mechanisms to reliably control timing of self-inflation such that premature inflation while in the esophagus during swallowing is avoided and sufficient inflation once in the stomach so as to prevent passage through the pyloric sphincter is ensured. Normal esophageal transit time for large food particles has been documented as 4-8 seconds, and gastric emptying of large food particles through the pylorus does not occur for at least 15-20 minutes. The outer container is preferably configured to separate, dissolve, degrade, erode, and/or otherwise allow the deflated/folded balloon to begin unfolding not less than 60 seconds but not more than 15 minutes after inoculation with liquid activation agent. The inner container is preferably configured chemically, mechanically or a combination thereof to retard the initial $CO_2$ generating chemical reaction such that sufficient $CO_2$ to begin inflating the balloon is not available earlier than 30 seconds after inoculation with the liquid activation agent, but to permit generation of sufficient $CO_2$ such that at least 10% of the occupyable volume of the balloon is filled within 30 minutes, at least 60% of the occupyable volume of the balloon is filled within 12 hours, and at least 90% of the occupyable volume of the balloon is filled within 24 hours. This timing allows for injection of the activation agent into the outer container by the medical professional, passing the device to the patient, and swallowing by normal peristaltic means by the patient. This timing also prohibits potential passing of an uninflated balloon into the duodenum by the balloon being inflated to a sufficient size such that gastric emptying of the balloon cannot be easy, as objects more than 7 mm in diameter do not readily pass.

Delivery Components

It certain embodiments, it may advantageous for an administrator of the device to use a delivery tool for delivering the device to the mouth or facilitating its passage through the esophagus in the optimal orientation. A delivery tool may enable the device administrator to inject the device with one or more inflation agents as the device 10 is being administered to the patient. In a preferred embodiment, such injection may be accomplished in the same mechanical action(s) of the administrator that are employed to release the device from the delivery tool into the mouth or esophagus. For example, the delivery tool may include a plunger, a reservoir having a liquid, and an injection needle. The administrator pushes the plunger which, either in sequence or approximately simultaneously, forces the injection needle into the device and thereby injects the liquid contained in reservoir into the device. Subsequent application of force to the plunger pushes the device out of the delivery tool and into the desired location within the patient. Furthermore, the delivery tool may also include a subcomponent that administers an anesthetic or lubricant into the patient's mouth or esophagus to ease the swallowability of the device.

Balloon

The volume-occupying subcomponent ("balloon") of the preferred embodiments is generally formed of a flexible material forming a wall which defines an exterior surface and an interior cavity. Various of the above-described subcomponents may be either incorporated into the wall or interior cavity of the volume-occupying subcomponent. As shown, volume-occupying subcomponent can vary in size and shape according to the patient's internal dimensions and the desired outcome. The volume-occupying subcomponent may be engineered to be semi-compliant, allowing the volume-occupying subcomponent to stretch or expand with increases in pressure and/or temperature. Alternatively, in some embodiments, a compliant wall offering little resistance to increases in volume may be desirable.

Spherical volume-occupying subcomponents are preferred in certain embodiments. Alternatively, the volume-occupying subcomponent may be constructed to be donut-shaped, with a hole in the middle of it, and may be weighted and shaped in such a way that it orients in the stomach to cover all or part of the pyloric sphincter, similar to a check valve. The hole in the middle of the volume-occupying subcomponent can then serve as the primary passage for the contents of the stomach to enter the small intestine, limiting the passage of food out of the stomach and inducing satiety by reducing gastric emptying. Volume-occupying subcomponent may be manufactured with different-sized donut-holes according to the degree that gastric emptying is desired to be reduced. Delivery, inflation and deflation of the volume-occupying subcomponent may be accomplished by any of the methods described above.

It is advantageous in certain embodiments for the volume-occupying subcomponent wall to be both high in strength and thin, so as to minimize the compacted volume of the device as it travels the esophagus of the patient. In certain embodiments, the volume-occupying subcomponent wall materials are manufactured with a biaxial orientation that imparts a high modulus value to the volume-occupying subcomponent.

In one embodiment, the volume-occupying subcomponent is constructed of a polymeric substance such as polyurethane, polyethylene terephthalate, polyethylene naphthalate, polyvinyl chloride (PVC), Nylon 6, Nylon 12, or polyether block amide (PEBA). The volume-occupying subcomponent may be coated with one or more layers of substances that modify (increase, reduce, or change over time) gas-barrier characteristics, such as a thermoplastic substance.

Preferably, the gas-barrier materials have a low permeability to carbon dioxide or other fluids that may be used to inflate the volume-occupying subcomponent. The barrier layers should have good adherence to the base material. Preferred barrier coating materials include biocompatible poly(hydroxyamino ethers), polyethylene naphthalate, polyvinylidene chloride (PVDC), saran, ethylene vinyl alcohol copolymers, polyvinyl acetate, silicon oxide (SiOx), acrylonitrile copolymers or copolymers of terephthalic acid and isophthalic acid with ethylene glycol and at least one diol. Alternative gas-barrier materials may include polyamine-polyepoxides. These materials are commonly acquired as a solvent or aqueous based thermosetting composition and are generally spray-coated onto a preform and then heat-cured to form the finished barrier coating. Alternative gas-barrier materials which may be applied as coatings to the volume-occupying subcomponent include metals such as silver or aluminum. Other materials that may be used to improve the gas impermeability of the volume-occupying subcomponent include, but are not limited to, gold or any noble metal, PET coated with saran, conformal coatings and the like, as listed, for example, in Tables 1a-b.

In certain preferred embodiments, the volume-occupying subcomponent is injection, blow or rotational molded. Either immediately following such molding, or after a period of curing, the gas-barrier coating may be applied if not already applied within the composite wall.

In another embodiment, the intragastric volume-occupying subcomponent is formed using a Mylar polyester film coating silver, aluminum or kelvalite as a metallized surface, to improve the gas impermeability of the volume-occupying subcomponent.

In the event that the volume-occupying subcomponent's wall is composed of multiple layers of materials, it may be necessary to use certain substances or methods to connect, attach or hold together such multiple layers. Such substances can include a solvent or an ether-based adhesive. Such multiple layers may also be heat-bonded together. Once such layers are attached together to form (for example) a sheet of material to be made into a volume-occupying subcomponent, it may also be necessary to apply additional treatment steps to such material to allow it to seal together (for example, by application of a certain degree of heat and pressure) in order to be made into a volume-occupying subcomponent. Accordingly, it may be advantageous to include as an additional layer in the volume-occupying subcomponent certain materials that seal. For example, a volume-occupying subcomponent comprised of a combination of PET and SiOx layers, which impart favorable mechanical and gas impermeability characteristics to the volume-occupying subcomponent, may be sealed by including a layer of sealable polyethylene in such volume-occupying subcomponent.

According to another embodiment of the preferred embodiments, the functionality of the volume-occupying subcomponent and the deflation component is combined either in part or in whole. For example, the volume-occupying subcomponent may be formed of a substance that is degraded within the stomach over a desired period of time. Once the degradation process has formed a breach in the wall of the volume-occupying subcomponent, the volume-occupying subcomponent deflates, continues to degrade and passes through the remainder of the digestive tract.

Preferably, an automated process is employed that takes a fully constructed volume-occupying subcomponent, evacuates all of the air within the interior cavity and folds or compresses the volume-occupying subcomponent into the desired delivery state. For example, the evacuation of air from the volume-occupying subcomponent may be actuated by vacuum or mechanical pressure (e.g. rolling the volume-occupying subcomponent). In certain embodiments, it is desirable to minimize the number of creases produced in the volume-occupying subcomponent when in the delivery state.

In another embodiment, deflation of the volume-occupying subcomponent may be achieved through one or more injection site within the wall of the volume-occupying subcomponent may be achieved through one or more injection sites within the wall of the volume-occupying subcomponent. For example, two self-sealing injection sites can be incorporated at opposite sides of the volume-occupying subcomponent. The volume-occupying subcomponent may be positioned within a fixture that employs two small-gauge needles to evacuate the air from the volume-occupying subcomponent.

In one embodiment, the self-sealing injection sites may further be used to insert chemical elements of the inflation subcomponent into the interior of the volume-occupying subcomponent. After injection of the chemical elements into the volume-occupying subcomponent, the same needles may be used to perform evacuation of the volume-occupying subcomponent.

It may be desirable that the volume-occupying subcomponent is packed into the delivery state under, for example, a negative vacuum pressure or under a positive external pressure.

The volume-occupying subcomponent wall materials may also be engineered to, once they are initially punctured or torn, tear relatively easily from the point of such puncture or tear. Such properties can, for example, be advantageous if deflation of the volume-occupying subcomponent were initiated by a tearing or puncturing of the volume-occupying subcomponent wall, since such initial tear or puncture may then increase in scope, hastening and/or maximizing the deflation process.

The volume-occupying subcomponent may also be coated by a lubricious substance that facilitates its passage out of the body following its deflation. Examples of possible coatings can be any substances with lubricious and/or hydrophilic properties and include glycerine, polyvinylpyrrolidone (PVP), petroleum jelly, aloe vera, silicon-based materials (e.g. Dow 360) and tetrafluoroethylene (TFE). The coating may be applied by a dipping, sputtering, vapor deposition or spraying process which may be conducted at an ambient or positive pressure.

The balloon composite wall materials can be of similar construction and composition as those described in U.S. Patent Publication No. 2010-0100116-A1, the contents of which is hereby incorporated by reference in its entirety. The materials are able to contain a fluid, preferably in compressed or non-compressed gas form, such as, e.g., $N_2$, Ar, $O_2$, $CO_2$, or mixture(s) thereof, or atmospheric air (composed of a mixture of $N_2$, $O_2$, Ar, $CO_2$, Ne, $CH_4$, He, Kr, $H_2$, and Xe) that simulate gastric space concentrations. In certain embodiments, the balloon is able to hold the fluid (gas) and maintain an acceptable volume for up to 6 months, preferably for at least 1 to 3 months after inflation. Particularly preferred fill gases include non-polar, large molecule gases that can be compressed for delivery.

Prior to placement in the outer container, the balloon is deflated and folded. In the inverted configuration in a deflated state, the balloon is flat, with the inverted seam extending around the perimeter of the balloon. The self-sealing valve system is affixed to the inner wall of the lumen close to the center of the deflated balloon, with the inner container positioned adjacent to the self-sealing valve system. The walls of the balloon are then folded. As part of the balloon design, the self-sealing valve system is manufactured in a manner such that it can be and is preferably placed "off center" to minimize the number of folds upon themselves (e.g., doubling or tripling up) required to fit the balloon in the outer container. For example, the self-sealing valve system can advantageously be placed ½ r±¼ r from the center of the balloon, wherein r is the radius of the balloon along a line extending from the center of the balloon through the septum.

Tracking and Visualization Subcomponent

It may also be beneficial to implement tracking and visualization functionality into devices according to the present inventions. Due to the non-invasive nature of the present device, physicians may desire to determine, or confirm, the location and orientation of the device prior to inflation or during the course of treatment.

Alternatively, the marker may be applied to the volume-occupying subcomponent when the volume-occupying subcomponent is in a creased or folded state such that when the volume-occupying subcomponent is in its deflated state the marker appears concentrated when viewed on visualization equipment, and when the volume-occupying subcomponent is inflated the marker appears less concentrated when viewed on visualization equipment. Alternatively, the marker may be applied or incorporated into the volume-occupying subcomponent so as to facilitate identification and location of the various subcomponents of the device, such as a valve, head, or weight. The marker may be printed or painted onto a surface of the volume-occupying subcomponent or between layers of the material forming the volume-occupying subcomponent. Alternatively, a metal coating as described below may be used as a marker to identify and/or locate the volume-occupying subcomponent. Metal coatings for visualizing the volume-occupying subcomponent may include silver, gold, tantalum or any noble metal. Alternatively, the marker may be applied to an elastomeric sleeve that covers all or part of the volume-occupying subcomponent.

In another embodiment, the volume-occupying subcomponent incorporates a subcomponent that changes mechanically upon inflation of the volume-occupying subcomponent, which mechanical change can be visualized using x-ray or other visualization equipment. For example, a mechanical portion of the volume-occupying subcomponent containing a visualization marker may elongate upon an increase in pressure in the volume-occupying subcomponent.

Alternatively, a marker may be formed using a metallized mesh located between layers of the material from which the volume-occupying subcomponent is constructed. The pattern or patterns formed by the imbedded marker will appear when the volume-occupying subcomponent is in an inflated, deployed state.

It is envisioned that marker materials may be incorporated into the volume-occupying subcomponent to facilitate various visualization techniques such as, for example, MRI, CT and ultrasound.

The volume-occupying subcomponent may also contain a dye or marker that is released upon deflation to indicate that the volume-occupying subcomponent cavity has been breached. Such dye or marker may, for example, be apparent in the patient's urine as an indication that the volume-occupying subcomponent has begun to deflate.

In yet further embodiments, microchips and other components employing electronic modalities may be used to locate and identify a device. Microchips analogous to those utilized for the identification of pets may be used to communicate device specific information and its approximate location. For example, a Wheatstone or other bridge circuit may be incorporated into the device and, together with RF "ping and listen" technology may be used as part of a system to determine the device's approximate location and measure and communicate device specific information. Such device specific information can include internal volume-occupying subcomponent pressure, which can indicate the degree of inflation of the volume-occupying subcomponent.

In yet further embodiments, mechanical, chemical, visual and other sensors may be included as part of the device to measure, record and/or transmit information relating to the device and/or the patient's internal environment. For example, the device may contain a camera or any of the other imaging and transmission components of a Pillcam device. As an additional example, the device may contain sensors that measure, record and/or transmit information relating to stomach pH, stomach pressure, hormone levels, organ health, and organ safety.

Valve System

In preferred embodiments, a self-sealing valve system is attached to the balloon (e.g., on its inside surface) that is "universal" or compatible with the swallowable catheter and a physician-assisted catheter. The valve system serves to allow for balloon inflation using a miniature catheter that includes a needle assembly and also provides a mechanism for detachment of the catheter after inflation has been completed. FIGS. 1A-D depict views representing a design of a self-sealing valve system which contains a self-sealing septum housed within a metallic concentric cylinder is provided. In the inflatable configuration, the self-sealing valve system is preferably adhered to the underside of the balloon material such that only a portion of the valve protrudes slightly outside of the balloon surface to ensure a smooth surface. The valve system for the inflatable configuration can utilize the same self-sealing septum designed for the self-inflating configuration. The septum preferably consists of a material possessing a durometer of 20 Shore A to 60 Shore D. The septum is inserted or otherwise fabricated into the smaller cylinder of the concentric metallic retaining structure (FIGS. 2A-D) that is preferably cylindrical in shape. The smaller cylinder within the larger cylinder controls alignment of the catheter needle sleeve/needle assembly with the septum, provides a hard barrier so that the catheter needle does not pierce the balloon material (needle stop mechanism), and provides compression such that the valve/septum re-seals after inflation and subsequent needle withdrawal.

The concentric valve system can also provide radio opacity during implantation and is preferably titanium, gold, stainless steel, MP35N (nonmagnetic, nickel-cobalt-chromium-molybdenum alloy) or the like. Non-metallic polymeric materials can also be used, e.g., an acrylic, epoxy, polycarbonate, nylon, polyethylene, PEEK, ABS, or PVC or any thermoplastic elastomer or thermoplastic polyurethane that is fabricated to be visible under x-ray (e.g., embedded with barium).

Figure 3A:
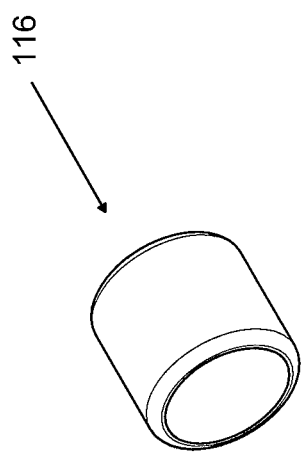
FIGS. 3A-C depict a perspective view (FIG. 3A), a side view (FIG. 3B), and a top view (FIG. 3C) of a ring stop 116—an additional ring placed at the distal end of an inner cylinder 118' to provide additional compression to ensure the septum material 114 is dense enough to re-seal itself, as in the self sealing valve system 100 of FIGS. 1A-D.
Figure 3C:
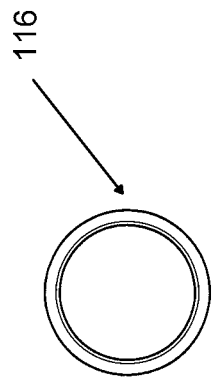
Figure 3B:
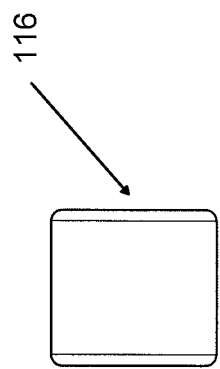
Figure 4B:
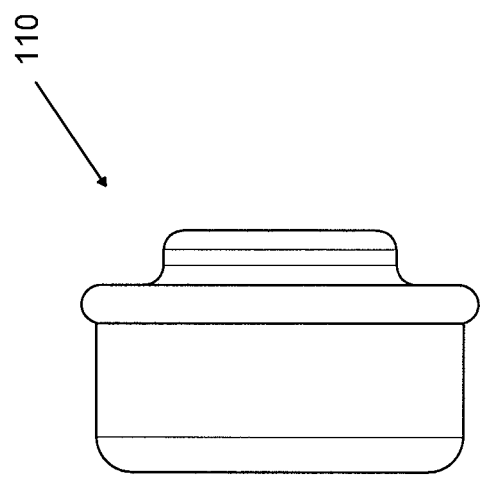
FIGS. 4A-D depict a perspective view (FIG. 4A), a side view (FIG. 4B), a cross-sectional view (FIG. 4C) and a top view (FIG. 4D) of a head unit 110 comprising an outer cylinder of a concentric valve housing comprising a higher durometer material than the inner cylinder, as in the self sealing valve system 100 of FIGS. 1A-D.
Figure 4A:
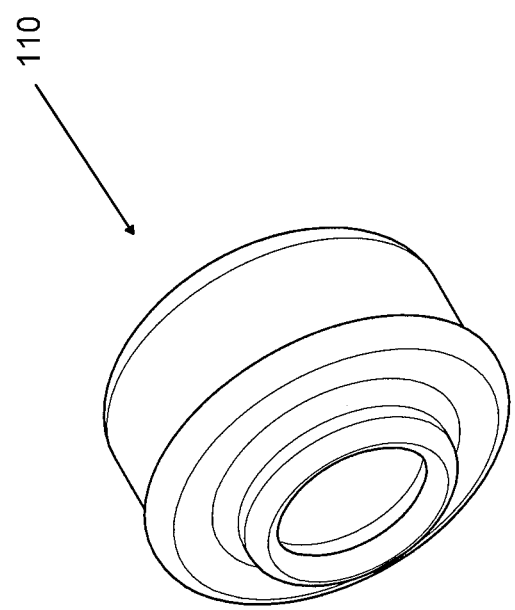
Figure 4D:
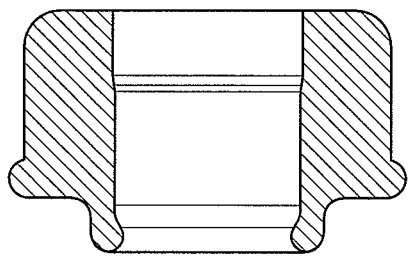
Figure 4C:
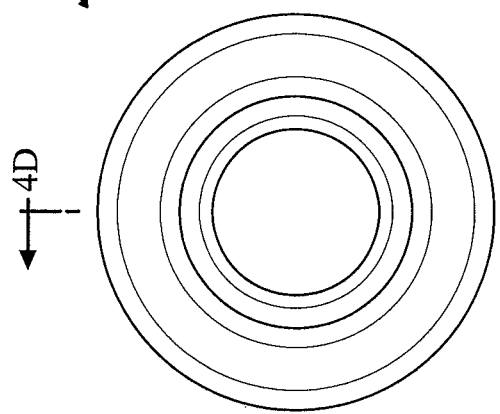

The septum can be cone shaped, so that the compressive forces are maximized for self-sealing after inflation. The self-sealing septum allows air to be evacuated from the balloon for processing/compacting and insertion into the outer container, and allows for piercing by an inflation agent syringe needle (self-inflating configuration) or inflation catheter needle (inflatable configuration), and then subsequent withdrawal of the inflation agent syringe needle or detachment of the inflation catheter and withdrawal of the catheter needle significantly limiting gas leakage outside of the balloon during the inflation process and needle withdrawal/catheter detachment. The septum is inserted into the valve using a mechanical fit mechanism to provide compression. An additional ring (FIGS. 3A-C) can be placed at the distal end of the inner cylinder to provide additional compression to ensure the septum material is pre-loaded so as to re-seal itself. The ring is preferably metallic in nature, but can also be a non-metallic polymeric material such as an acrylic, epoxy, or thermoplastic elastomer or thermoplastic polyurethane. The ring material is preferably the same material as the cylinder, titanium, but can also be gold, stainless steel, MP35N or the like.

In an inflatable configuration, a larger, outer cylinder (FIGS. 4A-D) of the concentric valve housing contains a slightly harder durometer material than the inner cylinder (50 Shore A or greater), but is also preferably silicone. The purpose of using a harder durometer material is to ensure sealing when connected to the needle sleeve for inflation. The silicone located in the outer ring of the concentric valve is adhered to the balloon from the inside surface. The entire outer cylinder is filled and a small circular lip of this same material is provided that is slightly larger than the diameter of the inner cylinder and extends to the outside surface of the balloon. The lip is compatible with the bell shaped needle sleeve and provides sealing to enhance connection of the valve to the catheter to withstand the inflation pressures applied and also increases the ejection distance or attachment force of the catheter. This silicone lip preferably does not protrude past the balloon surface more than 2 mm to ensure that the balloon surface remains relatively smooth and does not cause abrasion or ulcerations of the mucosa. It is designed to provide compressive forces against the needle sleeve of the catheter for inflation and detachment whereby when connected to the needle sleeve of the inflation catheter, the connection coupling can preferably withstand a pressure of 35 PSI during inflation. The seal is then broken during detachment using hydraulic pressure that is preferably more than 40 PSI but less than 200 PSI to separate the coupling. An additional retaining ring (FIGS. 5A-C) preferably made of the same material as concentric valve, can be included in the valve system to further enhance the seal between the metal and the valve silicone and provide additional mechanical support to ensure proper mechanical fit and are intended to disrupt slippage of the silicone material from the hard (metallic) valve system (causing an increase in tensile force).

The valve structure for the inflatable configuration uses a mechanical fit mechanism to provide the functions of the self-sealable valve for inflation by the catheter and subsequent catheter detachment; however, primer and/or adhesive may be used to provide additional support in construction of the assembly. The configuration can be modified by modifying the surfaces of the metal components, making them more sticky or slippery e.g. more or less conducive to adhesion, to provide the desired mechanical/interference fit. The interference fit between the valve and the catheter can be modified to change the pressure requirements for inflation and/or detachment. Additional assemblies can include overmolding the metallic portions or the concentric system in silicone such that additional support rings to ensure the mechanical fit and the tensile strength and forces required to sustain the assembly during catheter inflation and detachment can be omitted.

The total valve diameter in the inflatable configuration is designed to fit a miniature catheter system that does not exceed 8 French (2.7 mm, 0.105 inches) in diameter. The total diameter does not exceed 1 inch (2.54 cm) and is preferably less than 0.5 inches (1.27 cm), to facilitate swallowing. Additional valves can be added, if desired; however, it is generally preferred to employ a single valve so as to maintain the volume of the deflated/folded balloon (and thus the outer container dimensions) as small as possible. The valve system is preferably attached to the balloon and bonded such that a shear force greater than 9 lbs (40 N) is required to dislodge the valve system.

In a self-inflating configuration, the valve system can be attached to the balloon (e.g., on its inside surface) without the use of an opening, orifice, or other conduit in the wall of the balloon. The valve system can utilize a septum with a durometer of 20 Shore A to 60 Shore D. The valve can be inserted or otherwise fabricated into a retaining structure that has a higher durometer, e.g., 40 Shore D to 70 Shore D or more. The retaining structure can be fabricated from a silicone, rubber, soft plastic or any suitable non-metallic polymeric material such as an acrylic, an epoxy, a thermoplastic elastomer, or thermoplastic polyurethane. Preferably, a structure, such as a ring, that can be metallic or non-metallic but radio opaque (e.g., barium) and visible under X-ray, can be embedded in the retaining structure. Using a mechanical fit mechanism of two structures of different durometers, one softer (septum) with a large diameter, can be inserted into a snug, a higher durometer structure creates compressive forces in the once open orifice to enable $CO_2$ retention and reduce susceptibility for $CO_2$ gas leaks. The metallic ring for radio-opacity also helps to support compressive forces on the septum. The self-sealing septum allows air to be evacuated from the balloon for processing/compacting and inserting in the outer container, and also allows for the inflation agent to be injected into the outer container for inflation initiation. Additional septums can be provided, if desired; however, it is generally preferred to employ a single septum so as to minimize the volume of the deflated/folded balloon (and thus the outer capsule) to as small as possible. The valve system is preferably attached to the inside of the balloon such that a shear force greater than 9 lbs (40 N) is required to dislodge the valve system. A silicone head and radio opaque ring of a self-sealing valve system can be employed, as can a wedge-shaped septum.

In the self-inflating configuration, an inoculation spacer is preferably incorporated to guide a needle into the self-sealing valve for injection of liquid activation agent into the lumen of the balloon and to prevent the needle from penetrating the wall of the deflated/folded balloon elsewhere such that pressure within the lumen of the balloon cannot be maintained. The inoculation spacer also facilitates preventing liquid activation agent from penetrating the inner container or the folded balloon material, thereby focusing the activation agent in an appropriate manner to properly mix the reactants for $CO_2$ generation according to the criteria described above. The inoculation spacer is generally in the form of a tube or cylinder. The inoculation spacer is preferably attached to the inner container and/or the self-sealing valve system with an adhesive or other fixing means; however, in certain embodiments the inoculation spacer can be "free-floating" and maintained in position by the folding or rolling of the walls of the balloon. The inoculation spacer can comprise any suitable material that can be passed after separation, erosion, degradation, digestion, and/or dissolution of the outer container; however, preferable materials include non-metallic materials with a minimum Shore D durometer of 40 or more, any metallic material, or a combination thereof. A cupped needle stop (inoculation spacer) can be employed in preferred embodiments.

Balloon

In a preferred embodiment, a self-inflating balloon is fully sealed 360 degrees around. In the self-inflating configuration, with injection of an inflation agent by needle syringe, there are preferably no external openings or orifices to the central lumen. In the inflatable configuration, a valve structure (either protruding, recessed, or flush with the surface of the balloon) is provided for providing an inflation fluid to the central lumen. The balloon can have a "noninverted", "inverted", or "overlapped" configuration. In a "noninverted" configuration, the seams or welds and seam allowance, if any, are on the outside of the inflated balloon. In an "overlapped" configuration, layers are overlapped, optionally with one or more folds, and secured to each other via welds, a seam, adhesive, or the like, resulting in a smooth external surface. In an "inverted" configuration, the balloon has a smooth external surface with seams, welds, adhesive bead, or the like inside the inflated balloon. In order to create a balloon with an inverted configuration, e.g., a balloon with no external seam allowance (no wall material between the edge of the balloon and the weld, seam, or other feature joining the sides together), two balloon halves are joined together in some fashion (e.g., adhered using adhesive or heat or the like based on the balloon material used). One of the balloon halves encompasses an opening to allow for the balloon to be pulled through itself after adherence of the two halves and to have the seams of the balloon on the inside. The opening created is preferably circular but can be any similar shape, and the diameter of the opening preferably does not exceed 3.8 cm; however, in certain embodiments a larger diameter may be acceptable. A patch of material is adhered (adhesively, heat welded, or the like, based on the material used) to cover the original balloon-half opening. The inversion hole thus created that is subsequently patched is small enough that the forces exerted during inflation do not compromise the material used to maintain fluid in the balloon. The preferred shape for the inflated balloon in final assembly is ellipsoid, preferably spheroid or oblate spheroid, with nominal radii of from 1 inch (2.5 cm) to 3 inches (7.6 cm), a nominal height of from 0.25 inches (0.6 cm) to 3 inches (7.6 cm), a volume of from 90 cm$^3$ to 350 cm$^3$ (at 37° C. and at internal nominal pressure and/or full inflation), an internal nominal pressure (at 37° C.) of 0 psi (0 Pa) to 15 psi (103421 Pa), and a weight of less than 15 g. The self-inflating balloon is configured for self-inflation with $CO_2$ and is configured to retain more than 75% of the original nominal volume for at least 25 days, preferably for at least 90 days when residing in the stomach. The inflatable balloon is configured for inflation with an appropriate mixture of gases so as to deliver a preselected volume profile over a preselected time period (including one or more of volume increase periods, volume decrease periods, or steady state volume periods).

The preferred shape for the inflated balloon in final assembly is ellipsoid, preferably spheroid or oblate spheroid, with nominal radii of from 1 inch (2.5 cm) to 3 inches (7.6 cm), a nominal height of from 0.25 inches (0.6 cm) to 3 inches (7.6 cm), a volume of from 90 cm$^3$ to 350 cm$^3$ (at 37° C. and at internal nominal pressure and/or full inflation), an internal nominal pressure (at 37° C.) of 0 psi (0 Pa) to 15 psi (103421 Pa), and a weight of less than 15 g. In certain embodiments wherein a stable volume over the useful life of the device is preferred, the balloon is configured to maintain a volume of at least 90% to 110% of its original nominal volume. In other embodiments, it can be desirable for the balloon to increase and/or decrease in volume over its useful life (e.g., in a linear fashion, in a stepwise fashion, or in another non-linear fashion).

Inner Container

The inner container for the self-inflating balloon is contained within the lumen of the balloon and contains the $CO_2$ generator for balloon self-inflation. The $CO_2$ generator comprises an inflation agent mixture housed within the container. Preferably, from about 10% to about 80% of the total inflation agent used comprises powdered citric acid, with the remainder comprising powdered sodium bicarbonate. Sufficient inflation agent is provided such that upon completion of the $CO_2$ generating reaction, the balloon achieves inflation at the nominal inflation pressure described above. Preferably, a total of from about 0.28 to 4 grams inflation agent mixture is employed, depending upon the balloon size to be inflated; preferably up to 1.15 grams of sodium bicarbonate is used with the remainder being powdered citric acid to generate 300 cm$^3$ of $CO_2$ at nominal pressure.

Inflation Assembly

An intragastric balloon system that is manually inflated by a miniature catheter can be employed in certain embodiments. The system preferably remains "swallowable." The balloon for delivery is in a compacted state and is attached to a flexible, miniature catheter, preferably no larger than 4 French (1.35 mm) in diameter. The catheter is designed such that a portion of the catheter can be bundled or wrapped upon itself for delivery with the encapsulated balloon, allowing the patient to swallow both catheter and balloon for delivery to the stomach. The balloon can contain a self-sealable valve system for attachment of the catheter and inflation of the balloon once it reaches the stomach cavity. The proximal end of the catheter can be left just outside of the patient's mouth, permitting connection to an inflation fluid container that can house the preferred inflation fluid (gas or liquid). After inflation the catheter can be detached from the balloon valve and pulled back through the mouth. This method allows for the intragastric balloon to maintain its swallowability but allow for inflation by a fluid source or a mixture of fluid sources via the catheter. Alternatively, a more rigid, pushable system can be employed wherein the balloon valve is compatible with either the swallowable, flexible catheter or the pushable, rigid catheter assembly.

The inflation catheters (swallowable or administrator-assisted pushable) described herein are configured to deliver the balloon device orally and without any additional tools. The administration procedure does not require conscious sedation or other similar sedation procedures or require endoscopy tools for delivery. However, other versions of the device can be used in conjunction with endoscopy tools for visualization or can be adapted such that the balloon device can be delivered nasogastrically as well.

Figure 6:
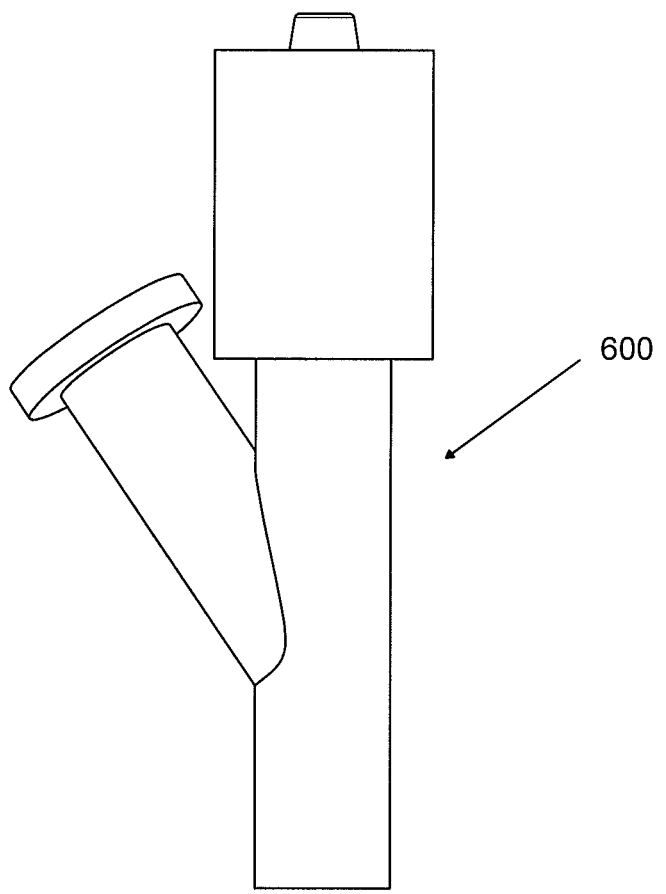
FIG. 6 depicts a connector 600 for a dual lumen catheter.
Figure 7:
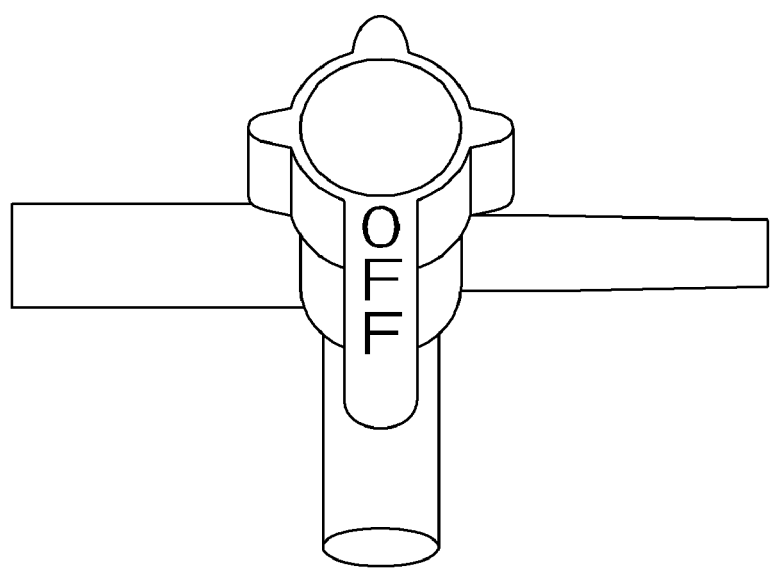
FIG. 7 depicts an inflation valve 700. The inflation valve is a 3-way valve configured for attachment to a single lumen catheter and that allows a method of exclusion for inflation and detachment of the balloon. The valve can be connected to a syringe 710 that functions as an inflation source or a source of detachment liquid.
Figure 8A:
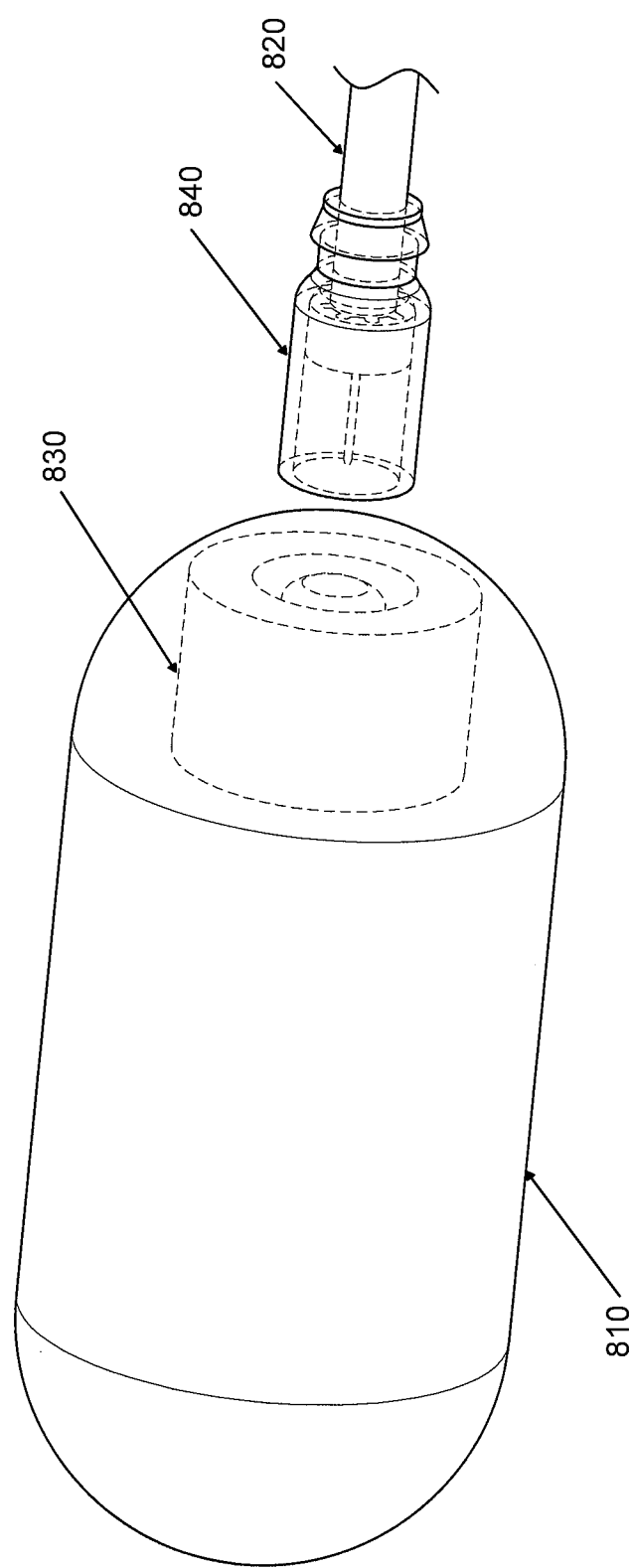
FIGS. 8A-B depicts a universal balloon valve 830 for connection to an inflation catheter 820 and a balloon (not depicted) encased in a balloon outer container 810.
Figure 8B:
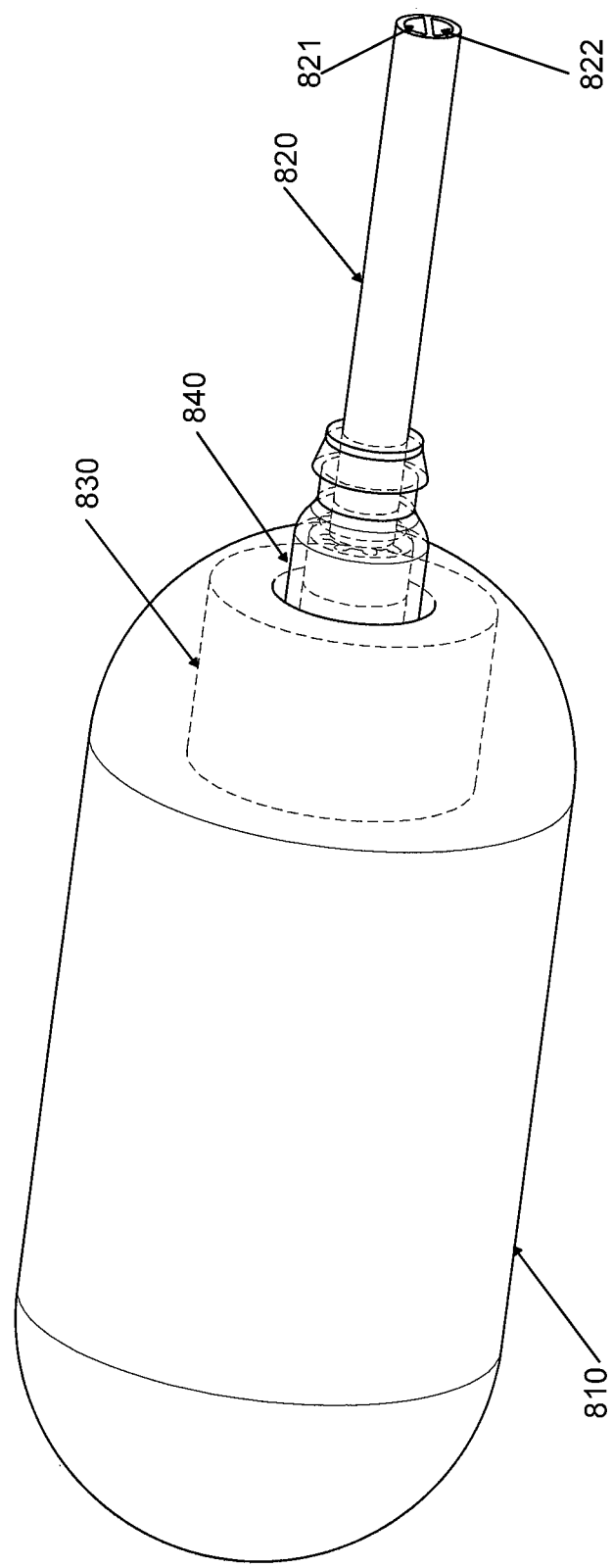

In operation, the proximal end of the inflation catheter is connected to a valve or connector that allows for connection to the inflation source or the disconnect source, this is preferably a connector or inflation valve (FIG. 6 and FIG. 7, respectively). The connector materials may consist of polycarbonate or the like and can connect to a single or multi-lumen catheter tube. The distal end of the inflation catheter is connected to the universal balloon valve of the balloon that has been compacted and housed within a gelatin capsule or compacted using gelatin bands (FIG. 8A-B). The catheter tube is preferably from 1 French (0.33 mm) to 6 French (2 mm) in diameter. The catheter is preferably long enough to extend out past the mouth (connected to the inflation connector or valve) and transverse the esophagus down to at least the middle of the stomach—approximately 50-60 cm. Measurement ticks can be added to the tubing or catheter to aid in identifying where the end of the tube is located. Timing for inflation can be initiated by having the tube contain a pH sensor that determines a location difference between the esophagus (pH 5-7) and the stomach (pH 1-4) based on the different pH between the two anatomical sources, or can be derived or verified from the expected pressure in a contained (i.e., esophagus) versus a less-constrained space (i.e., stomach). The tube can also contain nitinol that has a tunable transmission to the body temperature, taking into account the timing for swallowing. The tube can also be connected to a series of encapsulated or compacted balloons on a single catheter. Each can be inflated and released separately. The number of balloons released can be tune-able to the patient's needs and desired weight loss.

In certain embodiments, a catheter with the balloon at the distal end (inflated with air) is employed to temporarily and firmly hold the balloon in place. A small deflated balloon catheter can be positioned through the head of the gastric balloon (e.g., a "balloon within the balloon"), and then inflated with air during delivery to firmly hold the capsule and balloon in place and prevent spontaneous detachment of balloon from the catheter. This balloon catheter can incorporate a dual channel that can also allow the bigger gastric balloon to be inflated (by gas or liquid). Once the gastric balloon has been satisfactorily inflated, the small air balloon catheter can be deflated and pulled out of the valve (allowing the valve to self seal), and out of the body, leaving the inflated gastric balloon in the stomach.

In other embodiments, the catheter may be coated to enhance swallowability or is impregnated or treated with a flavored version and/or one or more local anesthetics or analgesics to ease swallowing. Such anesthetics may include anesthetics in the amino amide group, such as articaine, lidocaine and trimecaine, and anesthetics in the amino ester group, such as benzocaine, procaine and tetracaine. Such analgesics may include chloraseptic.

Dual Lumen Catheter

Figure 9A:
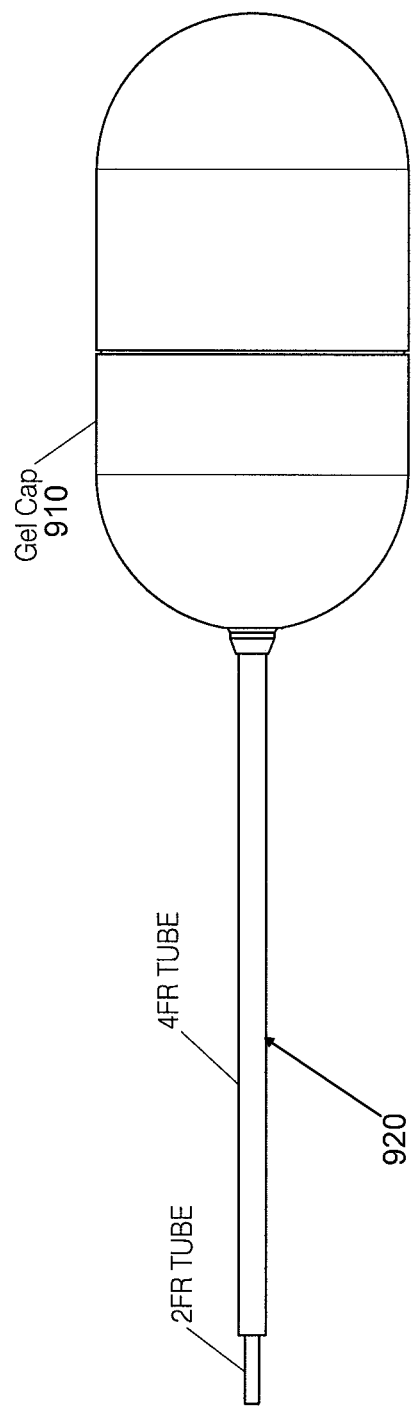
FIGS. 9A-C depict a side view (FIG. 9B), a bottom view (FIG. 9B) and a top view (FIG. 9C) of a dual lumen catheter 920 including a 2FR tube and a 4FR tube coupled to a gel cap 910 encapsulating a balloon (not depicted).
Figure 9C:
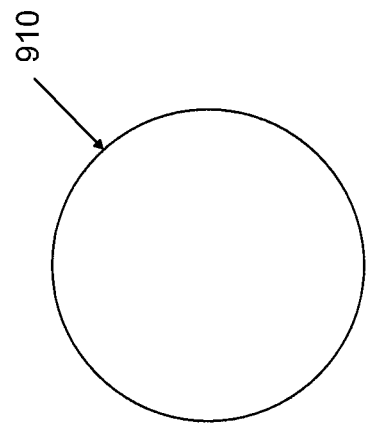
Figure 9B:
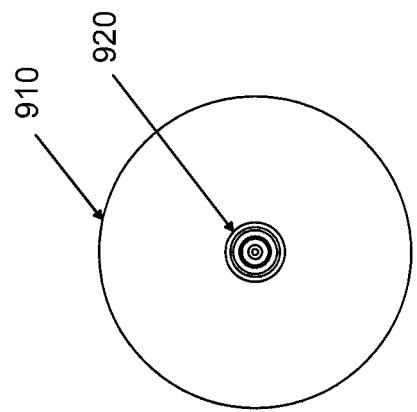

In a preferred embodiment, a swallowable dual lumen catheter is provided. The dual lumen catheter (FIGS. 9A-C) has two lumens with a diameter of the complete assembly no larger than 5 French (1.67 mm), preferably no larger than 4 French (1.35 mm). The inner lumen preferably does not exceed 3 French (1 mm) and functions as the inflation tube, and the outer lumen preferably does not exceed 5 French (1.67 mm) and functions as the disconnection tube. The catheter assembly is connected to a needle assembly, described in more detail below, at the distal end and to a dual port inflation connector at the proximal end. The tubing that the catheter assembly employs is flexible for swallowability, is kink resistant, can withstand body temperature, is resistant to acid, and is biocompatible as the tube transverses the alimentary canal into the stomach cavity. The tube materials are preferably soft and flexible and have moderate tensile strength and a significant amount of hoop strength to handle applied pressures. The lumens are preferably round and co-axial and free-floating so as to provide flexibility. The dual lumen assembly also preferably requires no adhesive or glue. Alternative lumen configurations can include two D-lumens or a combination of a D-lumen and round lumen, and can be used in stiffer configurations of the final catheter assembly. Preferred materials for the tubing include a thermo-resistant polyethylene tubing such as PEBAX® or a thermo resistant polyurethane tubing such as PELLETHANE™, PEEK or Nylon. The tubing can also be manufactured out of bioresorbable materials such as polylactic acid (PLA), poly-L-aspartic acid (PLAA), polylactic/glycolic acid (PLG), polycaprolactone (PCL), DL-lactide-co-ε-caprolactone (DL-PLCL) or the like, wherein the tube can be released after inflation and detachment and swallowed as normal.

At the distal end of the catheter assembly, the inner lumen or inflation tube is attached to the needle assembly that is used to puncture the balloon's self-sealing valve, preferably located at one of the apexes of the balloon housed inside of a gelatin capsule as outer container. The outer lumen is connected to the needle sleeve and provides connection force between the catheter assembly and balloon providing the tensile strength to withstand starting inflation pressures of preferably up to 10 psi and preferably no more than 35 PSI while maintaining the assembly together. The needle sleeve is configured to mechanically couple with the balloon valve assembly. The needle is preferably made of metal, preferably stainless steel or the like, with a maximum size of 25 gauge (0.455 mm), preferably no smaller than 30 gauge (0.255 mm) for inflation timing purposes. The needle sleeve is preferably a soft material such as nylon or the like, or can also be polycarbonate, polyethylene, PEEK, ABS or PVC. The needle sleeve covers the length of the needle in its entirety, such that the body is protected from the needle and the needle can only pierce the balloon septum. Preferably the needle sleeve is flush or extends out slightly more than the needle length. The needle is inserted into the balloon septum prior to swallowing and maintains a retention force of approximately 0.5 lb when coupled to the silicone area of the balloon valve. The needle sleeve is preferably slightly bell shaped (FIGS. 10A-D) or contains a circular relief or lip so that when inserted into the silicone area of the valve a lock and key mechanism is created to increase the tensile strength of the assembly and enhance the sealing for inflation.

At the proximal end, the catheter assembly is connected to a Y-adapter assembly preferably made of polycarbonate. The y-adapter is "keyed" so that the inflation gas and connection fluid are connected to the catheter assembly appropriately and travel down the correct lumen.

Prior to inflation, priming of the disconnection lumen may be employed using a liquid. For example, the outer lumen is first flushed with 2 cc of water, saline, DI water or the like prior to balloon inflation. Thereafter, the inflation source container is attached to the connector leading to the inner lumen. The inflation source container works on the premise of the ideal gas law and a pressure decay model. For a given compressed gas formulation, the device is designed to equalize such that a higher starting pressure is used to inflate the balloon than is the resulting end pressure of the balloon. The starting pressure and volume are dependent upon the gas formulation selected, as well as the length of the catheter and the starting temperature (typically ambient temperature) and ending temperature (typically body temperature).

After inflation, the balloon is detached from the catheter assembly using hydraulic pressure. A syringe filled with water, DI water, or preferably saline is attached to the female end of the Y-assembly. The syringe contains 2 cc of liquid and when the syringe plunger is pushed in, enough hydraulic pressure is exerted such that the needle is ejected from the balloon valve.

Single Lumen Catheter

Figure 11A:
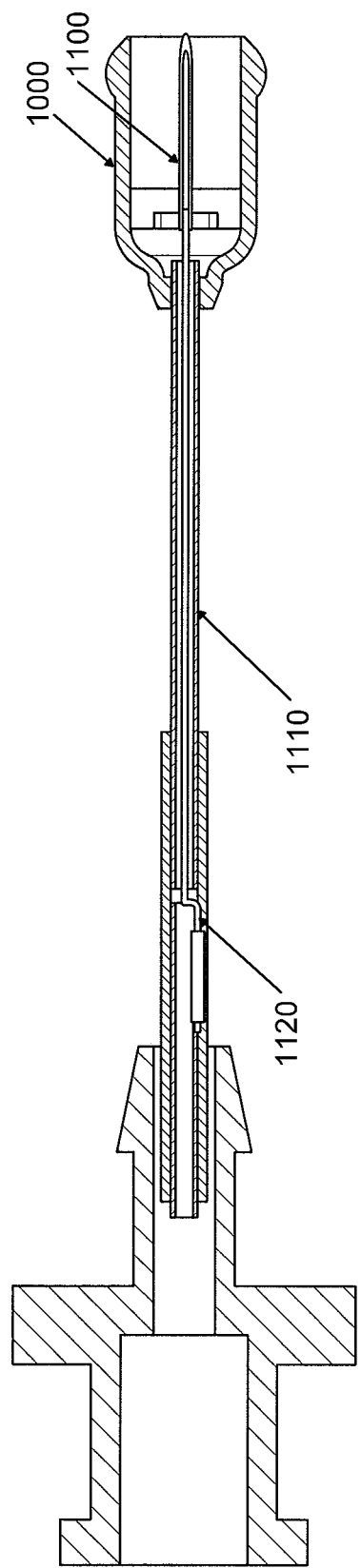
FIGS. 11A-C depict various embodiments of a single lumen catheter.
Figure 11B:
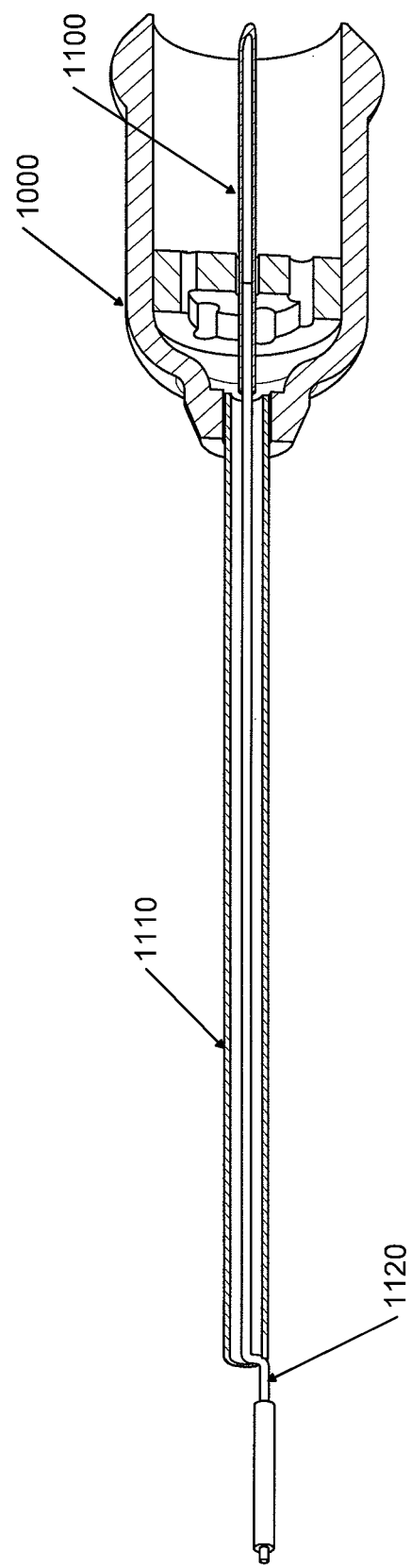

To further reduce the diameter of the inflation catheter, thereby increasing swallowability comfort of the balloon capsule and catheter, a single lumen catheter (FIG. 11A-C) can be employed that does not exceed 3 French (1.0 mm) in diameter (0.033 inches).

The needle/needle sleeve assembly is similar in design to that of the dual lumen catheter described herein. However, with the single lumen system, the distal end of the catheter lumen connects to the needle sleeve only and there is no second catheter inside. Instead, a single thread attached to a needle hub runs co-axially the length of the catheter to aid in tensile strength for detachment and overall flexibility.

The needle sleeve is slightly bell shaped or contains a circular relief or lip so that when inserted into the silicone head of the valve a lock and key mechanism is created to increase the tensile strength of the assembly, enhance the sealing for inflation, and since this is a single lumen assembly, the lip increases the force required to remove the needle from the valve so this does not occur haphazardly during the inflation process.

The proximal end of the catheter is connected to an inflation valve (FIG. 7), preferably a 3-way valve, or any valve that allows for using a method of exclusion for inflation and detachment of the balloon. The distal end of the catheter contains the needle sleeve, which is made of nylon or other similar source. The needle is metallic and preferably stainless steel.

The tubing that the catheter assembly employs is flexible for swallowability, is kink resistant, can withstand body temperature, is resistant to acid, and is biocompatible as the tube transverses the alimentary canal into the stomach cavity. The tube materials are preferably soft and flexible and resistant to necking or buckling or kinking. For a single lumen system, the catheter tubing is preferably made of PEBAX® or PELLETHANE® (an ether-based polyurethane elastomer), but can also comprise bioresorbable materials such as PLA, PLAA, PLG, PCL, DL-PLCL or the like, wherein the tube can be released after inflation and detachment and swallowed as normal. The threadlike wire (FIG. 11 B) inside the catheter tubing attached to the needle is preferably a nylon monofilament, but Kevlar or nitinol wire or other suitable materials can also be used.

Figure 11C:
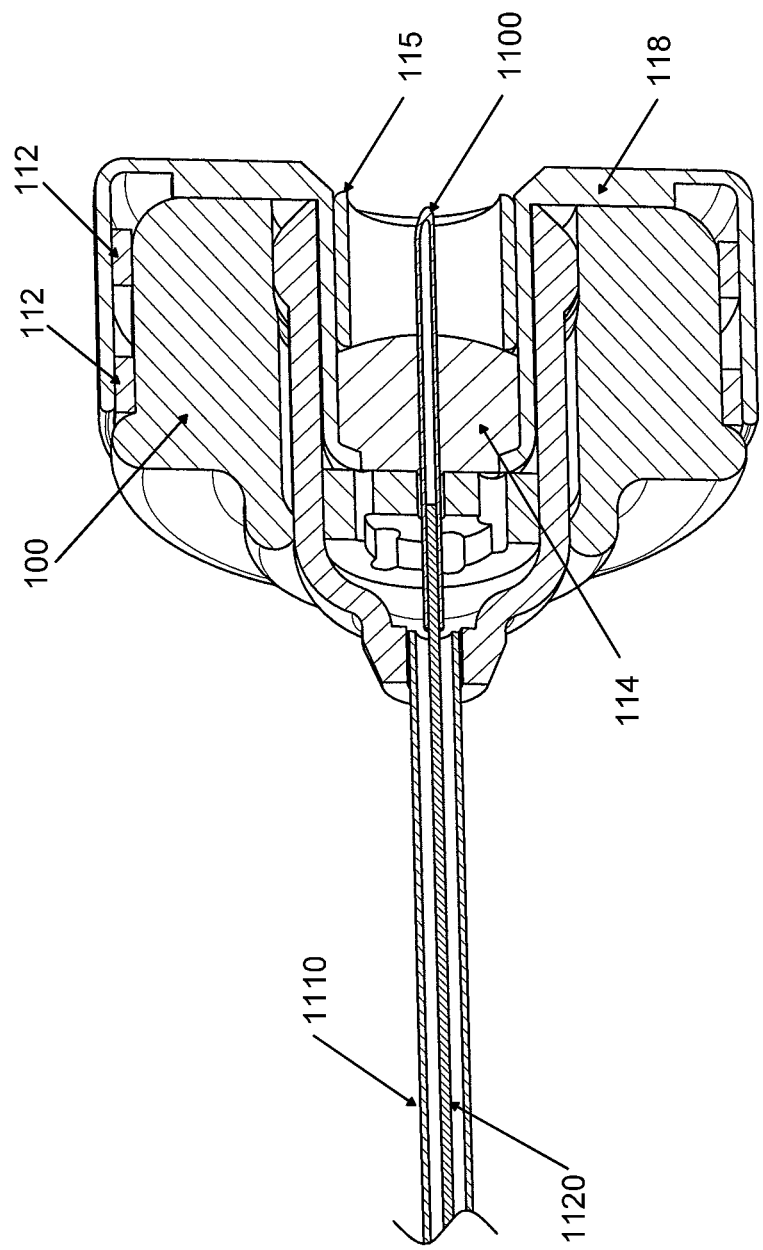
Figure 12D:
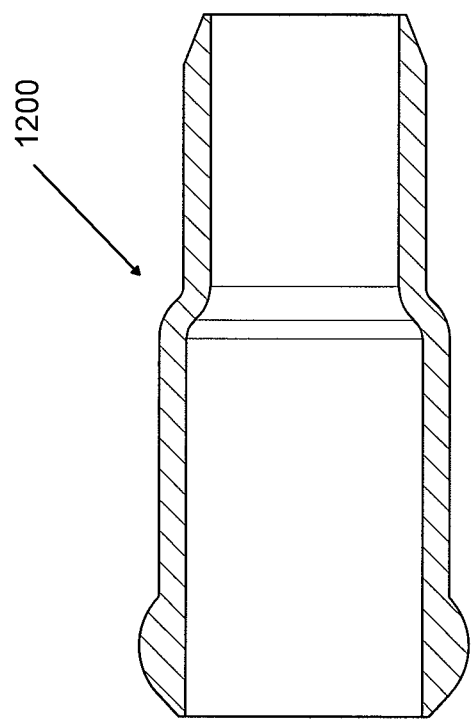
Figure 12C:
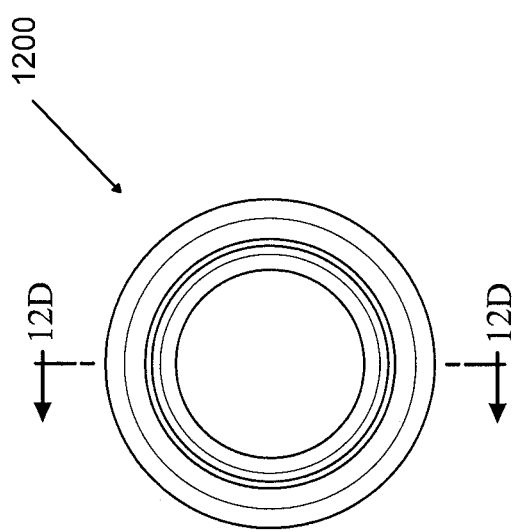

To inflate the balloon, the distal end of the catheter is attached to the balloon capsule where the needle protrudes through the self-sealable valve (FIG. 11C). The container is swallowed and a portion of the inflation catheter remains outside of the mouth. The inflation source container is connected to the proximal end of the inflation valve, where the port for inflation gas is chosen by excluding the other ports. The inflation fluid (preferably compressed nitrogen gas or a mixture of gases) travels down the single catheter lumen, whereby the inflation gas selects the path of least resistance, or more specifically through the needle cavity and into the balloon. The balloon is preferably inflated in less than 3 minutes.

To detach and withdraw the needle from the balloon valve, 2 cc or other suitable volume of water or other liquid is injected into the catheter at a high pressure. Since water has a high surface tension and viscosity, it occludes the needle pathway and the pressure is transferred to the outside needle sleeve, thereby breaking the fit between the needle sleeve and the balloon valve.

If it is desired to place a substance inside the balloon, such as water or acid or any alternative liquid, it can be done by using a lower pressure to inject the liquid.

Miniature Stiff-Bodied Inflation Catheter

In certain embodiments, a stiff-bodied inflation catheter can be employed, which can be placed orally or transnasally. This system can be from 1 French (0.33 mm) to 10 French (3.3 mm), preferably 8 French (2.7 mm) in diameter. A larger diameter is typically preferred to enhance pushability, with wall thickness also contributing to pushability and kink resistance. The length of the tube can be approximately 50-60 cm. As discussed above, measurement ticks can be added to the tubing to identify where the end of the tube is located, or a pH or pressure sensor on the catheter can be employed to detect location of the balloon.

This system for inflation/detachment is similar to the dual lumen system described above, but with a larger needle sleeve to accommodate the larger diameter tube (FIGS. 12A-D). Materials that can be used in the lumen include, e.g., expanded polytetrafluoroethylene (EPTFE) for the outer lumen and polyetheretherketone (PEEK) for the inner lumen. To also enhance pushability, a strain relief device can be added to the distal and proximal ends. It is particularly preferred to have strain relief at the distal end, e.g., 1 to 8 inches, preferably 6 inches, to ensure the catheter bypasses the larynx and follows into the esophagus. The proximal end can have strain relief as well, e.g., to ensure fit of the connector. The preferred material for the strain relief is a polyolefin. The method for inflation/detachment is the same method as for the dual lumen configuration where the outer lumen connects to the needle sleeve and the inner lumen connects to the needle. Stiffening members are strategically placed along the length of the catheter shaft to provide the correct amount of flexibility and pushability to properly place the device in the patient. As part of the procedure, the patient can swallow water or other suitable liquid so as to distend esophageal tissue for smooth passage down of the device. Patients can also be administered an anesthetic at the back of the throat to numb the area and lessen the gag reflex.

The tube can also be connected to a series of encapsulated or compacted balloons on a single catheter such that a total volume of up to 1000 cc or more can be administered, as necessary. Each can be inflated and released separately. The number of balloons released can be tunable to the patient's needs and desired weight loss.

Figure 13:
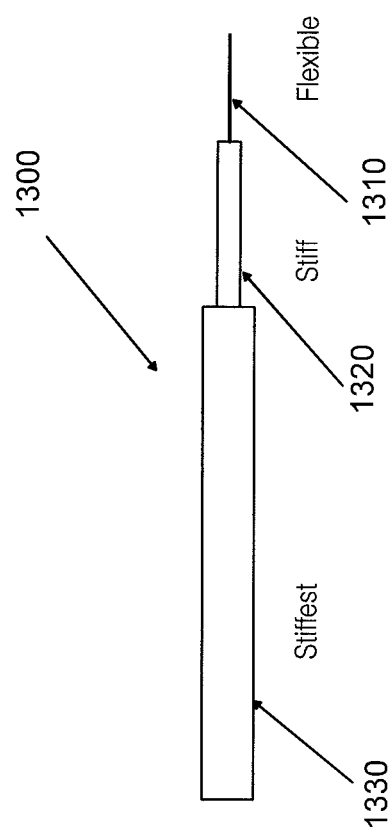
FIG. 13 depicts a variable stiffness catheter 1300 for administering a gastric balloon, the catheter including a flexible portion 1310, a stiff portion 1320, and a stiffest portion 1330.

In addition, a catheter can be used for administering a gastric balloon that is similar to balloon catheters used in angioplasty termed "over-the-wire" or rapid exchange catheters (FIG. 13). In this case where the patients attempts to swallow the catheter but fails so the stiff catheter—or physician assisted catheter can slide over the flexible catheter and the balloon can be pushed down in the same manner as the physician-assisted catheter. Different materials can be used to provide the varying degrees of flexibility or one material that is fabricated with different diameters across the length to vary the degree of stiffness can be used.

Inflation Fluid Container

Figure 14A:
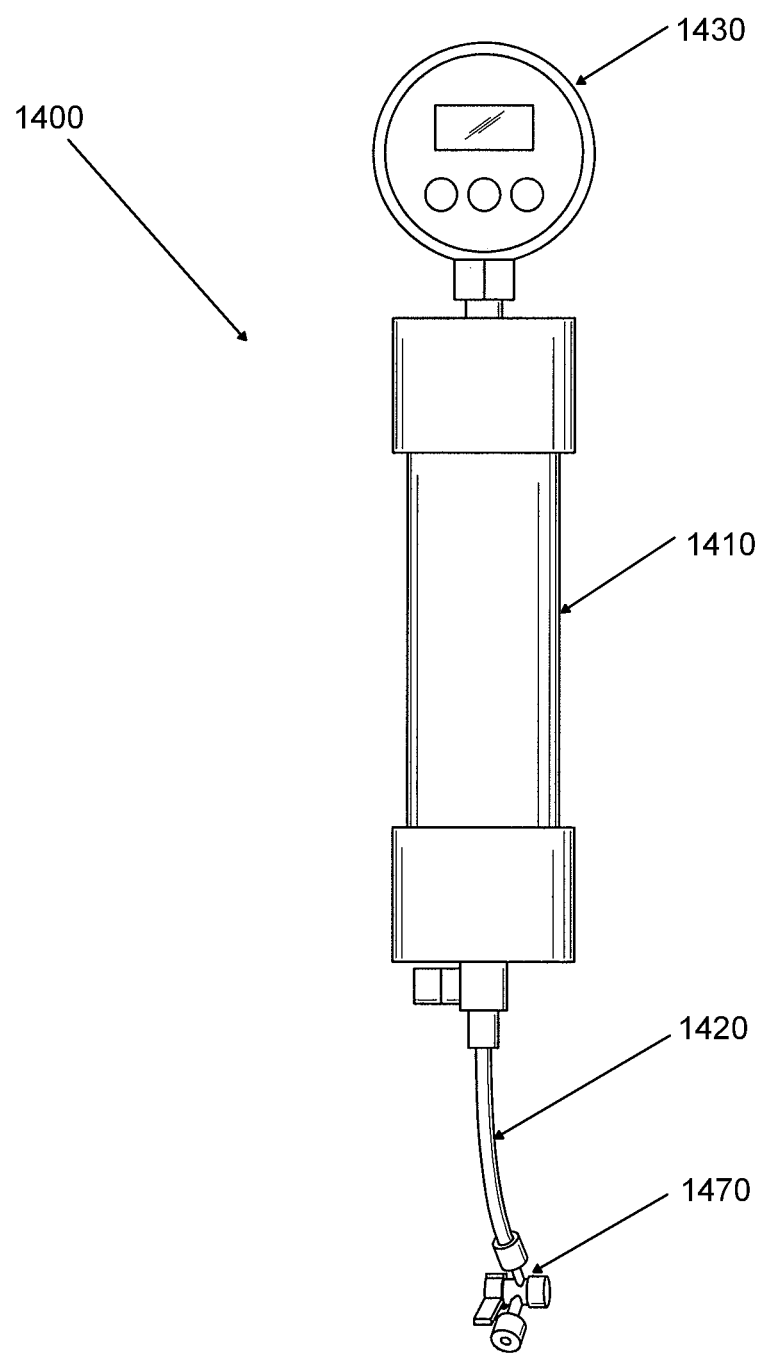
FIGS. 14A-B depict an inflation fluid container system 1400 (FIG. 14A) including a connector 1420 to the catheter (not depicted) including a valve 1470, an inflation fluid (or source) container 1410 and a pressure gauge 1430. Detail of the connector 1420, inflation fluid (or source) container 1410, and valve 1470 are provided in FIG. 14B.
Figure 14B:
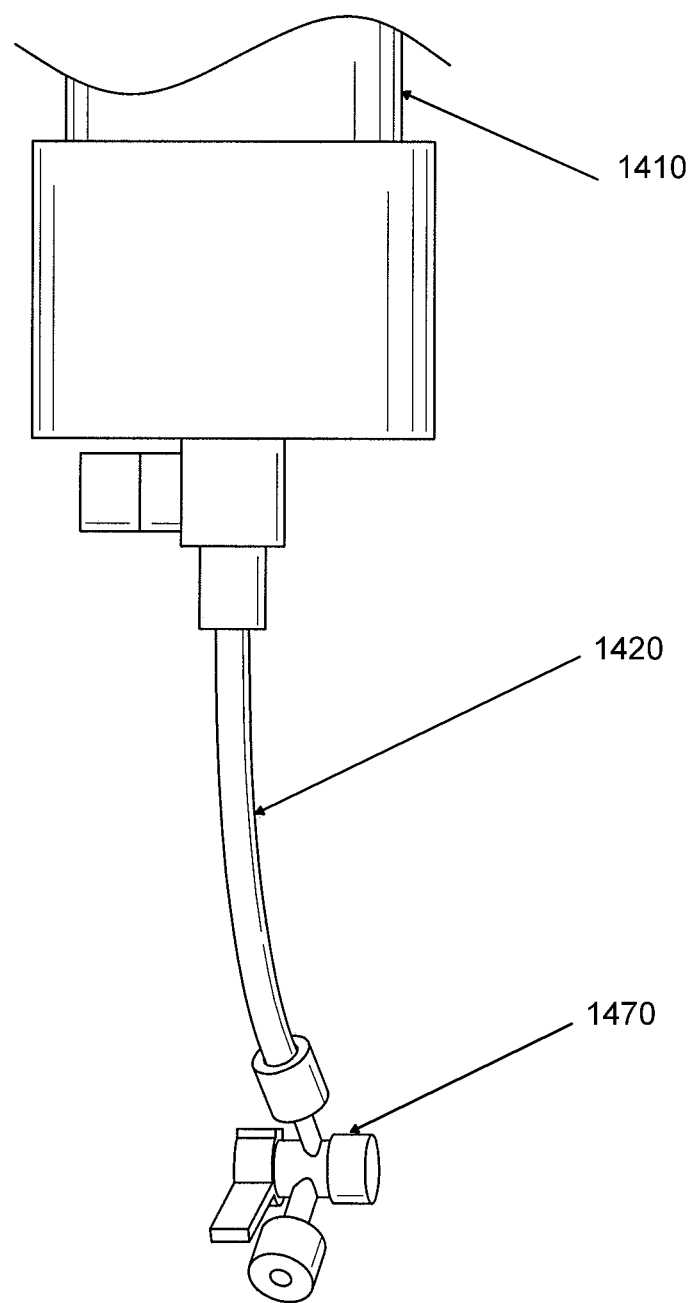
Figure 15A:
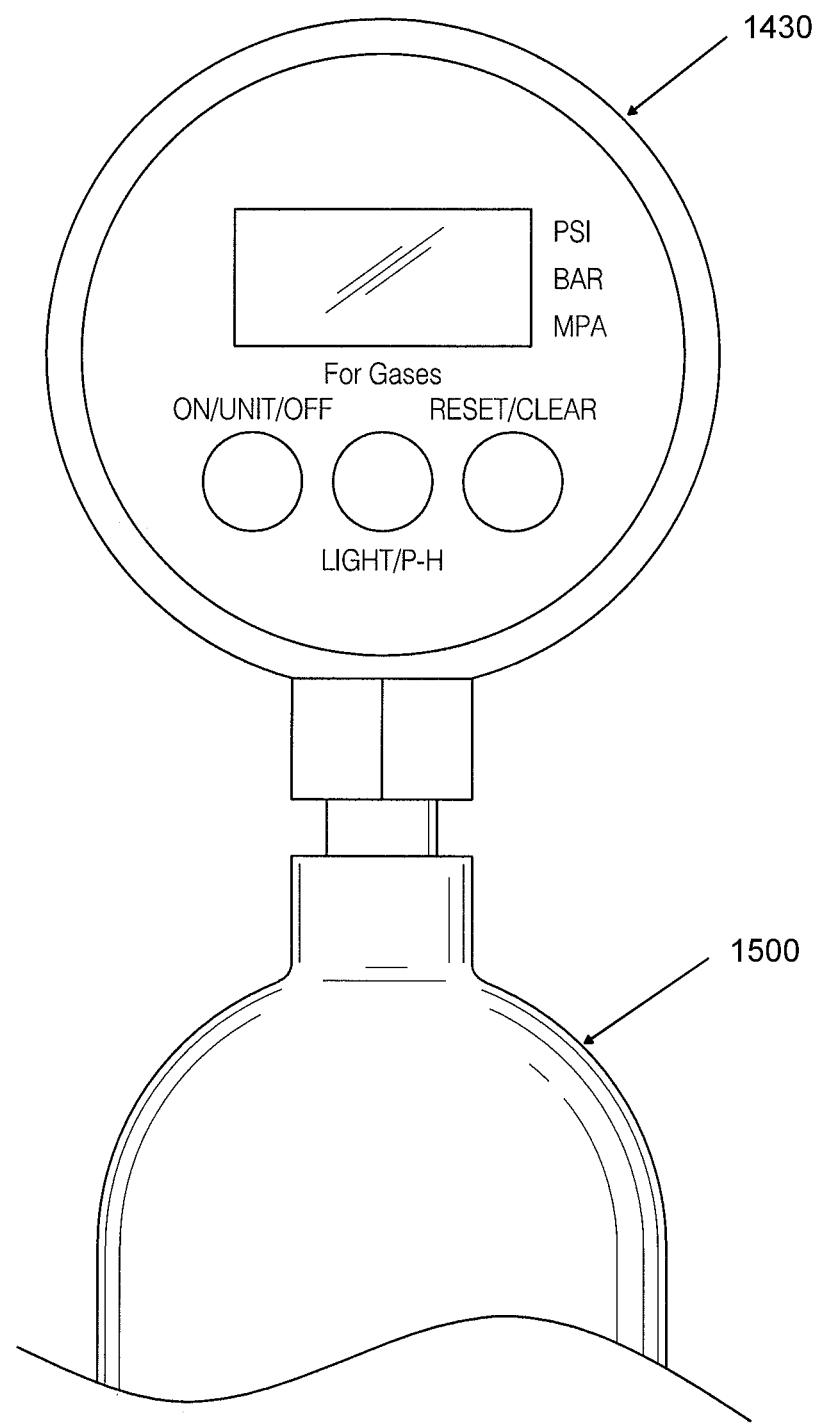
FIGS. 15A-B depict a stainless steel inflation fluid container 1500 connected to a pressure gauge 1530 (FIG. 15A) and a connector to the catheter including a valve 1540 (FIG. 15B).
Figure 15B:
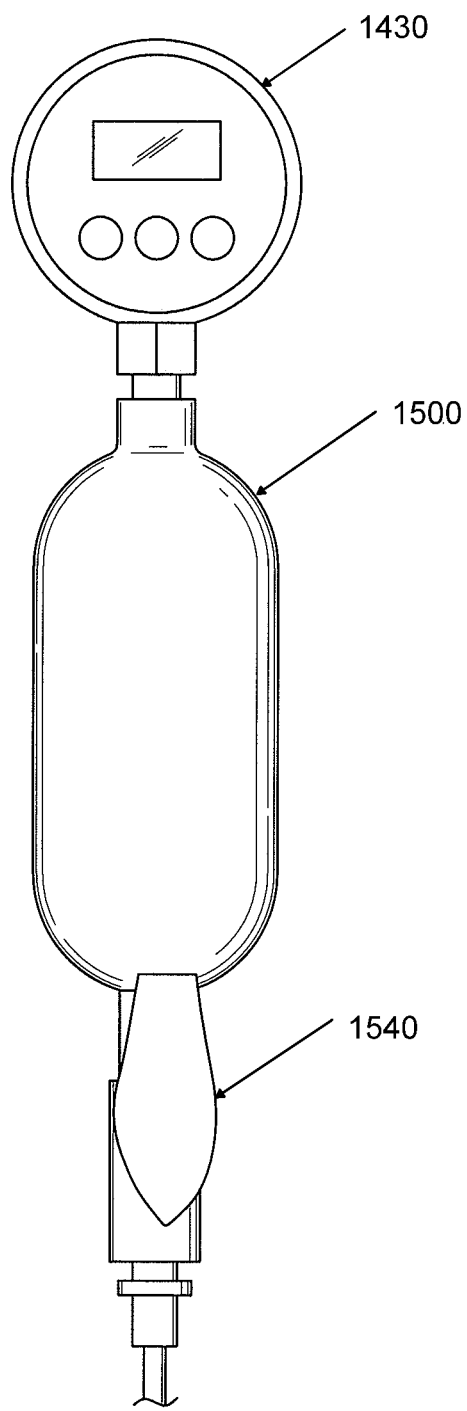

The inflation fluid container is employed to control the amount or volume of fluid placed inside of the balloon. This can be in the form of a canister of, e.g., PVC, stainless steel, or other suitable material. The container can also be in syringe form. The materials employed are able contain a fluid, preferably in gas form, e.g., compressed or non-compressed $N_2$, Ar, $O_2$, $CO_2$, or mixture(s) thereof, or compressed or non-compressed atmospheric air (a mixture of $N_2$, $O_2$, Ar, $CO_2$, Ne, $CH_4$, He, Kr, $H_2$, and Xe). The balloon composite wall materials and respective diffusion gradients and gas permeability characteristics are used to select a fluid for inflation of the intragastric balloon. The Inflation Fluid container materials are selected to ensure there is no diffusion or leakage of the fluid before it is connected to the connector or valve of the inflation catheter. The inflation fluid container system (FIGS. 14A-C) includes a connector (FIG. 14B) to the catheter and a pressure gauge (FIG. 14C). The inflation fluid container can be fabricated from any suitable material, e.g., stainless steel (FIG. 15). It can also contain a smart chip that notifies the healthcare professional of whether inflation is successful or if the balloon should be detached due to an error in the system.

To maintain "swallowability" of the balloon and to ensure comfort of the patient during the procedure, it is preferred to minimize the amount of time the catheter is placed in the mouth/esophagus. Timing of inflation is can be selected so as to minimize time in place. The outer container-catheter assembly, once swallowed, takes approximately 4-8 seconds to reach the stomach. Once in the stomach, the Inflation source container can be attached to the valve or port of catheter system. Inflation timing can be controlled by selecting the length of catheter, diameter of the catheter tube, the starting temperature, and the starting pressure. Using the Ideal Gas Law for nitrogen and Boyle's Law ($P_1V_1=P_2V_2$) the amount of starting volume/pressure can be derived, where temperature is controlled inside the inflation source container to match that of the body. It is desired to have an inflation time after swallow of less than 5 minutes, and preferably 2-3 minutes, before balloon detachment and catheter withdrawal. The inputs use to derive inflation of the balloon (preferably in less than 3 minutes) include inflation container volume, type of inflation fluid (preferably a compressed gas or compressed gas mixture), starting pressure, catheter length and diameter, and desired end volume and pressure of the balloon. Thus, due to differences in diameter, a 2 French catheter system requires a higher starting pressure to achieve the same target balloon volume and pressure in the same time frame, assuming use of the same compressed gas formulation. In general, it is understood that starting with a higher pressure with the same flow rate/volume can decrease the inflation time.

Figure 16:
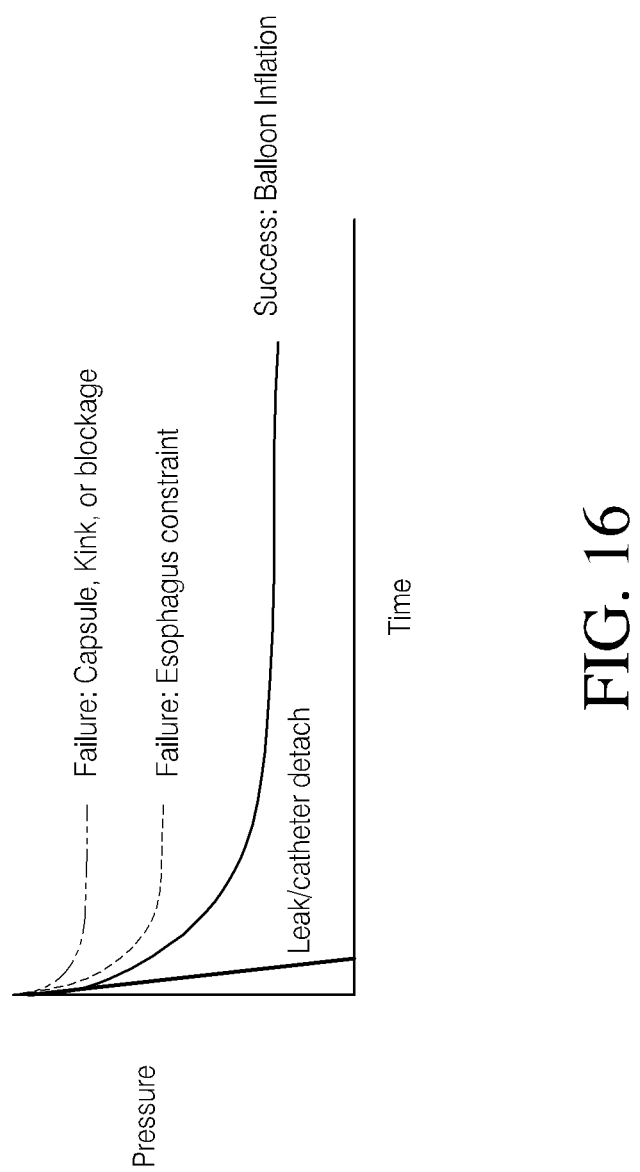
FIG. 16 is a graph depicting pressure as a function of time (pressure decay), obtained from feedback from an inflation source container.

The inflation source container provides feedback to the end user based on a pressure decay system. Where there is an expected starting pressure and expected ending pressure to indicate whether the balloon is inflated properly, there is no need for endoscopic visualization (see FIG. 16). Each scenario of expected pressure outputs depicted in FIG. 16 can have its own tolerances around it to reduce possibilities of false positives, and the inflation fluid container can provide feedback based on these tolerances as to the status of balloon inflation and detachment. This is derived based on the Ideal Gas Law, where there is an expected end pressure based on the fixed volume of the balloon. If the pressure remains high and doesn't decay as expected, this can indicate a failure in the system (e.g., the balloon container did not dissolve, the balloon is expanding in the esophagus because there is, e.g., a kink in the tube or other failure in the catheter system). For example, for a successful decay using nitrogen only as the inflation fluid, the starting pressure is 22 PSI to inflate a balloon to 250 cc and 1.7 psi (0.120 kg/cm$^2$) for a nylon-based material. To indicate successful balloon inflation, a math chip can be added to the inflation source container that provides at least one of a visual, audible, or tactile notification, or otherwise transmits a notification to a healthcare professional or administrator of whether inflation is successful or if there is an error in the system based on the pressure curve and a set of predetermined pressure tolerances and expected timing of inflation.

Figure 17:
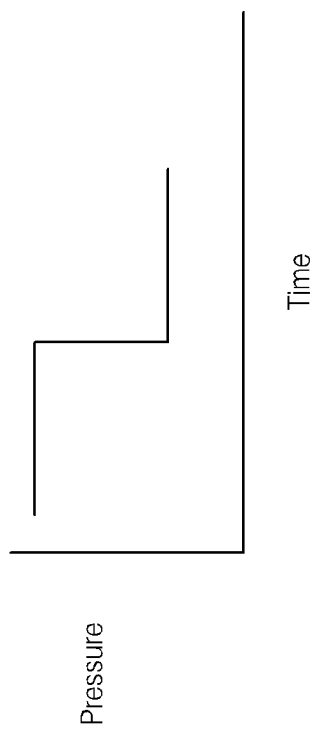
FIG. 17 depicts the expected decay curve for pressure sources using a spring mechanism or a balloon-within-balloon mechanism.

Alternatively, the balloon can be filled based on a starting pressure by using a spring mechanism, a balloon-within-balloon mechanism, or other pressure source. These mechanisms can potentially result in more predictable/consistent pressure decay curves, and again can have accompanying, predetermined tolerances for feedback back to the end user. FIG. 17 depicts the expected decay curve for these methods of pressure sources, and again would have accompanying, predetermined tolerances for feedback back to the end user.

Composite Wall

The materials selected for the composite wall of the balloon may be optimized to maintain the original inflation gas without significant diffusion, or may also allow for diffusion of the gases located in the gastric environment, e.g., $CO_2$, $O_2$, argon, or $N_2$ to diffuse through the wall of the balloon to inflate, partially or wholly, once the balloon is placed in the stomach. A fluid (a liquid or gas) can also be added inside of the balloon using the inflation catheter(s) described herein to change diffusion direction of the balloon composite wall and when it reaches stasis based on the internal and external environment.

A gastric balloon inflated by nitrogen, $CO_2$ gas, a single fluid (gas) or a mixture of gasses employs a composite wall that provides barrier properties (fluid retention), properties imparting resistance to pH and moisture conditions in the gastric environment or the environment within the central lumen of the balloon, and structural properties to resist gastric motility forces, abrasion of the balloon wall in vivo, and damage during manufacturing and folding of the balloon. Certain materials employed in the balloon materials are able to withstand a hostile gastric environment designed to break down foreign objects (e.g., food particles). Some of the variables that the gastric environment encompasses are as follows: gastric liquid pH of from 1.5-5; temperature of approx. 37° C.; a relative humidity of 90-100%; ingress of gastric space gas content; and constant gastric motility external pressures of from 0-4 psi at variable frequencies and cycle times based on the fed state of the stomach. The external pressure imparted by gastric motility can also cause abrasions on the surface of the balloon. The inside of the balloon lumen may contain moisture from a solution injected in the balloon for timing of auto-deflation or any moisture that has transferred across the membrane due to the external humid environment. In addition to these environmental stresses the wall materials meet biocompatibility requirements and are constructed such that the total thickness of the wall (barrier material) is thin enough to be compacted and placed inside of a swallowable-sized container ("outer container") without significant damage or lodging. The outer container is small enough to transcend the esophagus (which has a diameter of approximately 2.5 cm). The wall or barrier material is also heat formable and sealable for balloon construct and maintains a bond strength that can contain internal gas pressures of up to 10 psi generated by the initial inflation pressure as well as pressure due to the ingress of gas molecules from the stomach cavity until the system's gas environment reaches stasis. The film properties that are evaluated to determine suitability for use in the composite wall of the balloon include pH resistance, water vapor transmission rate, gas barrier properties, mechanical strength/abrasion properties, temperature resistance, formability, flex-crack (Gelbo) resistance, surface energy (wettability) compliance, and heat bond potential.

The various layers in the composite wall can impart one or more desirable properties to the balloon (e.g., fluid retention, resistance to moisture, resistance to acidic environment, wettability for processing, and structural strength). A list of polymer resins and coatings that can be combined into a multi-layer preformed system ("composite wall") is provided in Tables 1a-b. These films can be adhesively bonded together, co-extruded, or adhered via tie layers or a combination thereof to obtain the desired combination of properties for the composite wall, as discussed below. The materials identified as film coatings in Tables 1a-b are provided as coatings applied to a base polymer film, e.g., PET, Nylon, or other structural layer.

TABLE 1a

Film Resins

| FILM RESINS | Characteristics | | |
|---|---|---|---|
| | Good Structural/Behavior/ Mechanical Strength/Compliance | Good Fluid Retention Barrier Properties | Good Manufacturability/ Surface Energy Properties |
| Polyethylene Terephthalate (PET) | X | X | |
| Polytrimethylene Terephthalate (PTT) | | | |
| Liquid Crystal Polymer (LCP) | X | X | |
| Polytrimethylene naphthalate (PTN) | X | X | |
| Polyethylene naphthalate (PEN) | X | X | |
| Polyimide (PI) | X | X | |
| Linear Low Density Polyethylene (LLDPE) | | | X |
| Ethylene Vinyl Alcohol (EVOH) | | X | |
| Polyamide:Nylon (PA) and Nylon-6 (PAG)/Nylon 12 | | X | X |
| High Density Polyethylene (HDPE) | | | X |
| Polypropylene (PP) | | | X |
| Polyurethane | | | X |
| PVDC (Saran) | | X | X |
| Polyether Block Amide (Pebax) | | | X |
| Polyvinyl Alcohol (PVOH) | | X | |
| Silicone | X | | X |

TABLE 1b

Film Coatings

| FILM COATINGS | Characteristics | | |
|---|---|---|---|
| | Good Structural/Behavior/ Mechanical Strength/Compliance | Good Fluid Retention Barrier Properties | Good Manufacturability/ Surface Energy Properties |
| Silicone Dioxide (SiO2) | | X | |
| Aluminum Oxide (Al$_2$O$_3$) | | X | |
| Nanopolymers (Nano/Clay) | | X | |
| External Organic Coatings (e.g., epoxy amine) | | X | |

TABLE 1b-continued

Film Coatings

| | Characteristics | | |
|---|---|---|---|
| | Good Structural/Behavior/ Mechanical Strength/Compliance | Good Fluid Retention Barrier Properties | Good Manufacturability/ Surface Energy Properties |
| FILM COATINGS | | | |
| Inorganic Coatings (e.g., Amorphous Carbon) | | X | |
| Oxygen Scavengers | | X | |
| Parylene C | | X | |

Fluid Retention Layers

In preferred embodiments, a blended polymer resin using multiple layers is employed to maintain the inflated balloon's shape and volume by retaining the inflation fluid for the duration of the intended use. Certain barrier films, widely used in the food packaging and plastic bottling industries, can advantageously be employed for this purpose in the composite wall of the balloon. Preferably, the barrier materials have a low permeability to carbon dioxide (or other gases, liquids, or fluids that are alternatively or additionally used to inflate the volume-occupying subcomponent). These barrier layers preferably have good adherence to the base material. Preferred barrier coating materials and films include polyethylene terephthalate (PET), linear low density polyethylene (LLDPE), ethylene vinyl alcohol (EVOH), polyamides such as Nylon (PA) and Nylon-6 (PA-6), polyimide (PI), liquid crystal polymer (LCP), high density polyethylene (HDPE), polypropylene (PP), biocompatible poly(hydroxyamino ethers), polyethylene naphthalate, polyvinylidene chloride (PVDC), saran, ethylene vinyl alcohol copolymers, polyvinyl acetate, silicon oxide (SiOx), silicon dioxide ($SiO_2$), aluminum oxide ($Al_2O_3$), polyvinyl alcohol (PVOH), nanopolymers (e.g., nanoclay), polyimide thermoset film, EVALCA EVAL EF-XL, Hostaphan GN, Hostaphan RHBY, RHB MI, Techbarrier HX (SiOx-coated PET), Triad Silver (silver metallized PET), Oxyshield 2454, Bicor 84 AOH, acrylonitrile copolymers, and copolymers of terephthalic acid and isophthalic acid with ethylene glycol and at least one diol. Alternative gas-barrier materials include polyamine-polyepoxides. These materials are typically provided as a solvent-based or aqueous-based thermosetting composition and are typically spray-coated onto a preform and then heat-cured to form the finished barrier coating. Alternative gas barrier materials that can be applied as coatings to the volume-occupying subcomponent include metals such as silver or aluminum. Other materials that may be used to improve the gas impermeability of the volume occupying subcomponent include, but are not limited to, gold or any noble metal, PET coated with saran, and conformal coatings.

One method that is used in the packaging industry to delay diffusion of the inflation fluid is to thicken the material. Thickening the material is generally not preferred, as the total composite wall thickness preferably does not exceed 0.004 inches (0.010 cm) in order for the balloon to be foldable into the desired delivery container size for swallowing by a patient.

A multilayer polymer film that is able to withstand the gastric environment over the course of the usable life of the balloon includes linear low density polyethylene (LLDPE) adhesively bonded to a Nylon 12 film. Alternatively, an additional film layer with barrier properties, such as PVDC can be added to the composite wall.

The layers providing gas barrier properties are preferably situated as inner layers in the composite wall as they are less mechanically robust than resins that are considered "structural" such as Nylon and the like.

Structural Layers

Layers such as polyurethane, Nylon, or polyethylene terephthalate (PET) can be added to the composite wall for structural purposes, and are preferably placed as outermost (proximal to the gastric environment or proximal to the central lumen of the balloon) layers, provided that the pH resistance of such layers can withstand the acidic environment of the stomach or the central lumen of the balloon.

Fabrication of the Composite Wall

The various layers of the composite wall, including the gas barrier layers, need not be situated in any particular order, but those of superior resistance to acidity, temperature, mechanical abrasion, and superior biocompatibility profile are preferably employed as layers contacting the gastric environment. Those with superior resistance to, e.g., acidity and temperature, are preferably employed as layers contacting the central lumen of the balloon.

The various layers of the wall can include a single layer or up to 10 or more different monolayers; however, a film thickness of from 0.001 inches (0.0254 cm) to 0.004 inches (0.010 cm) thick is desirable such that the resulting balloon compacted to fit into a swallowable capsule. The resulting composite wall preferably has good performance specifications with respect to each category listed in Tables 1a-b.

Films that are co-extruded are advantageously employed, as some adhesives may contain leachables that are undesirable from a biocompatibility perspective. In addition, coextrusion allows for better blending such that the materials maintain their original properties when combined in this fashion and are less likely to be subject to delamination when exposed to gastric motility forces.

Combining films with similar properties, e.g., two film layers with excellent gas barrier properties, in a composite wall is advantageous for use in a gastric balloon containing nitrogen, oxygen, $CO_2$ or a mixture thereof as the inflation gas or where the external environment the product is to be placed in, contains a mixture of gases including $CO_2$, e.g., the stomach. A primary advantage of such composite films is that restrictions on film thickness can be observed without sacrifice of gas barrier properties. Such a configuration also contributes to reducing the effects of processing damage (e.g., manufacturing and compacting) and damage due to exposure to in vivo conditions (e.g., gastric motility forces).

In a particularly preferred embodiment, the composite wall includes a plurality of layers. The first layer is an outer protective layer that is configured for exposure to the gastric environment. This layer is resistant to mechanical forces, exposure to water (vapor), abrasion, and high acidity levels. Nylon or more specifically, Nylon 12 is particularly preferred for the layer exposed to the gastric environment, and is especially resistant to mechanical forces.

In an alternative embodiment, polyurethane is RF welded to saran to yield a 6-7 mil thick composite wall. In another embodiment, a five layer system is provided comprising a layer of saran sandwiched between two polyurethane layers. Between the saran layer and each of the polyurethane layers is a tie layer. The layers can be welded together, co-extruded or adhered using an adhesive. This tri-layer is then co-extruded to Nylon on each side, and then a final sealing layer (polyethylene or the like) is added to one of the nylon layers for the total composite wall. A representative example of material combinations that are commercially available or manufacturable is provided in Table 2. The orientation of the layers (innermost—in contact with the central balloon lumen, or outermost—in contact with the gastric environment) is also indicated if more than two layers are described to support a suggested composite wall.

Most of the film resins listed in Table 2 provide some degree of gas barrier properties. Therefore, many can be used solely to form the balloon wall as a monolayer film; however they can also be used in conjunction with other film resins to meet the desired gas retention and mechanical specifications for the useful life of the balloon based on the inflation gas and external environment the balloon is to be placed in. These film resins can also be coated with gas barrier coatings listed in Tables 1a-b. Additional film layers can be added to form the total composite wall. While such additional layers may not impart substantial barrier properties, they can provide structural and/or mechanical properties, protection for the other layers of the composite wall that are susceptible to water vapor, humidity, pH, or the like, or other desirable properties. The film layers can be assembled using various adhesives, via co-extrusion, via lamination, and/or using tie layers and such to create a composite wall that meets the requirements of an intragastric balloon suitable for use for at least 25 days, or up to 90 days or more, with the specified gas retention properties. Table 2 provides a list of layers and layer combinations suitable for use in composite walls for an intragastric balloon. The composite description, resin abbreviation, configuration (single layer, bilayer, trilayer, or the like) and trade name of commercially available combinations are listed. The number of layers indicated does not include any adhesive layers or tie layers used to fabricate the composite wall, such that a 6-layer composite wall may, for example, have two or three adhesive layers and/or tie layers that make up the total composite wall, and therefore the total number of layers can be eight or nine in final form. The term "layer" as used herein is a broad term, and is to be given its ordinary and customary meaning to a person of ordinary skill in the art (and is not to be limited to a special or customized meaning), and refers without limitation to a single thickness of a homogenous substance (e.g., a coating such as SiOx, or a layer such as PET), as well as to a supporting layer having a coating thereon (wherein a "coating" is, e.g., a material typically employed in conjunction with substrate that provides structural support to the coating layer). For example, a PET-SiOx "layer" is referred to herein, wherein a layer of Si-Ox is provided on a supporting PET layer.

TABLE 2

| Example Film Composite Walls* | Abbreviation | Trade name |
|---|---|---|
| polyethylene terephthalate | PET | Mylar |
| metallized oriented polyethylene terephthalate | metallized OPET | Custom |
| polyvinyl alcohol coated oriented polypropylene | PVOH coated OPP | Bicor |
| metallized biaxially oriented nylon 6 | metallized OPA6 | Custom |
| Biaxially oriented Nylon/ethylene vinyl alcohol/biaxially oriented Nylon | OPA/EVOH/OPA | Honeywell Oxyshield Plus |
| Nylon/ethylene vinyl alcohol/Low Density Polyethylene | Nylon/EVOH/LDPE | Custom |
| polyvinylidene chloride coated oriented polyethylene terephthalate | PVDC/OPET | Mylar |
| polyvinylidene chloride coated oriented polypropylene | PVCD/OPP | Custom |
| polyvinylidene chloride coated biaxially oriented Nylon 6 | PVCD/OPA6 | Honeywell Oxyshield |
| high density polyethylene/ethylene vinyl alcohol | HDPE/EVOH | Custom |
| polypropylene/ethylene vinyl alcohol laminate | PP/EVOH | Custom |
| polyethylene terephthalate/ethylene vinyl alcohol | PET/EVOH | Custom |
| metallized oriented polypropylene | metallized OPP | Custom |
| sealable PVDC coated oriented polypropylene | PVDC coated PP | Custom |
| polyvinylidene fluoride | PVDF | Custom |
| Polyvinyl chloride | PVC | Custom |
| polyvinyl fluoride | PVF | Tedlar |
| polychlorofluoroethylene | PCTFE | ACLAR UltRx, SupRx, Rx |
| amine-based epoxy coated Nylon | epoxy coated PA6 | Bairocade |
| polyvinyl chloride-polyvinylidene chloride copolymer | PVC-PVDC | Custom |
| medium density polyethylene | MDPE | Custom |
| Nylon/Polypropylene | Nylon/PP laminate | Custom |

TABLE 2-continued

| Example Film Composite Walls* | Abbreviation | Trade name |
|---|---|---|
| Nylon-High Density Polyethylene | Nylon-HDPE laminate | Custom |
| Nylon 12/Ethyl Methyl Acrylate/Polyvinylidene Chloride/Ethyl Methyl Acrylate/Nylon 12/Linear Low Density Polyethylene + Low Density Polyethylene | Co-extruded Nylon 12-encapsulated PVDC-Nylon 12-LLDPE + LDPE | Custom Co-extruded blend |
| Multi-layer Nylon 12/Linear Low Density Polyethylene + Low Density Polyethylene | Co-extruded multi-layer Nylon 12-LLDPE + LDPE | Custom Co-Extruded Blend |
| acetylene plasma coating on polyester | PET/A | Custom |
| difluoroethylene coating on polyethylene terephthalate | PET/DA | Custom |
| oriented polypropylene | OPP | Custom |
| cast propylene | CPP | Custom |
| high density polyethylene | HDPE | Custom |
| cyclic olefin copolymer | COC | Custom |
| oriented polystyrene | OPS | Custom |
| Fluorinated Ethylene Propylene | FEP | Custom |
| difluoroethylene coating on low density polyethylene | LDPE/D | Custom |
| difluoroethylene coating on polypropylene | PP/D | Custom |
| acetylene plasma coating on polypropylene | PP/A | Custom |
| acetylene plasma coating on low density polyethylene | LDPE/A | Custom |
| polybutylene terephthalate polyether glycol copolymer | TPC-ET | Hytrel |
| polyether block amide TPE | PEBA | Pebax |
| oxide coated biaxially oriented Nylon | oxide coated PA | Honeywell Oxyshield Ultra |
| Nanoclay/nylon | MXD6/Nanoclay | Imperm/Aegis OXCE |
| Polyethylene Terephthalate/Silicone Dioxide | PET/SiOx | BestPET/TechBarrier |
| Polyethylene Terephthalate/Oxygen scavengers | PET + O2 Scavengers | MonoxBar |
| Modified Polyethylene Terephthalate | Modified PET | DiamondClear |
| Polyethylene Terephthalate/Nylon 6 | PET/MXD6 | HP867 |
| Amorphous polyvinyl alcohol | Amorphous PVOH | Nichigo G-Polymer |
| Nylon 6/Ethyl vinyl alcohol/Linear Low Density Polyethylene | Nylon 6/EVOH/LLDPE | Custom |
| Ethyl vinyl alcohol/Poly-Propylene/Ethyl vinyl alcohol | EVOH/PP/EVOH | Custom |
| Ethyl vinyl alcohol/Nylon | EVOH/Nylon | Custom |
| Polyethylene/Ethyl vinyl alcohol/Polyethylene | PE/EVOH/PE | Custom |
| Polyethylene/Ethyl vinyl alcohol/Polyethylene Terephthalate | PE/EVOH/PET | Custom |
| Silicon dioxide-coated Polyethylene Terephthalate/Linear Low Density Polyethylene/Ethyl vinyl alcohol/Linear Low Density Polyethylene | PET-SiOx/LLDPE/EVOH/LLDPE | Custom |
| Aluminum Oxide-coated Polyethylene Terephthalate/Polyethylene | PET-Al2O3/LLDPE | Custom |
| Polyethylene/Ethyl vinyl alcohol/Linear Low Density Polyethylene | PE/EVOH/LLDPE | Custom |
| Polyethylene Terephthalate/Polyethylene/Polyethylene/Bi-axially oriented Ethyl vinyl alcohol | PET/PE/OEVOH/PE | Custom |
| Polyethylene Terephthalate/Polyethylene/Ethyl vinyl alcohol/Ethyl vinyl alcohol/Ethyl vinyl alcohol/Polyethylene | PET/PE/EVOH/EVOH/EVOH/PE | Custom |
| Polyethylene Terephthalate/Polyethylene/Nylon 6/Ethyl vinyl alcohol/Nylon 6/Polyethylene | PET/PE/Nylon 6/EVOH/Nylon 6/PE | Custom |

TABLE 2-continued

| Example Film Composite Walls* | Abbreviation | Trade name |
|---|---|---|
| Silicone dioxide-coated Polyethylene Terephthalate/ Polyethylene/Ethyl vinyl alcohol/ Polyethylene | PET-SiOx/PE/EVOH/PE | Custom |
| Polyethylene/Ethyl vinyl alcohol/polyvinylchloride | PE/EVOH/PVDC | Custom |
| Polyethylene Terephthalate/Linear Low Density Polyethylene/Ethyl vinyl alcohol/Linear Low Density Polyethylene | PET/LLDPE/EVOH/LLDPE | Custom |
| Kurrarister C-coated Polyethylene Terephthalate/Polyethylene/Ethyl vinyl alcohol/Polyethylene | PET-Kurrarister-C/PE/EVOH/PE | Custom |
| Polyethylene Terephthalate/ Polyethylene/Nylon 6/Ethyl vinyl alcohol/Nylon 6/Polyethylene | PET/PE/Nylon 6/EVOH/Nylon 6/PE | Custom |
| Nylon 6/Ethyl vinyl alcohol/ Polyvinylchloride/Low Density Polyethylene | Nylon 6/EVOH/PVDC/Nylon 6/LDPE | Custom |
| Polyimide | PI | Custom |
| Polyimide/Linear Low Density Polyethylene | PI/LLDPE | Custom |
| Polyimide/Polyvinylchloride | PI/PVdC | Custom |
| Polyimide/Polyvinylchloride/ Linear Low Density Polyethylene | PI/PVdC/LLDPE | Custom |

In particularly preferred embodiments, the composite wall has a thickness of 0.005 inches or less (5.0 mil or less); however, in certain embodiments a thicker composite wall may be acceptable. Generally it is preferred that the composite wall have a thickness of no more than 0.004 inches (4.0 mil).

Fabrication of the Balloon

To ensure good mechanical strength of the balloon, the balloon is preferably formed and sealed such that the edges of the pieces used to form the balloon are overlapping. This can be accomplished by any suitable method. For example, two flat sheets of material can be placed in a frame with magnetized edges to hold the two sheets in place. Slack can be added to the piece of film to orient the material such that it maintains its properties after the forming process. The frame can be placed over a mold that represents a hemisphere the balloon. The material, with slack put in it prior to pressure being applied, re-orients the material such that it is more evenly distributed around the hemisphere shape. The material is preferably thickest in the middle and is made thinner on the sides where it will be welded to a second piece to create a sphere or ellipsoid having a substantially uniform wall thickness. For example, starting with a 0.0295" film, the middle of the film or subsequent apex has an ending film thickness of 0.0045" and the edges have an ending thickness of 0.0265" for subsequent overlapping during the welding process.

Figure 18A:
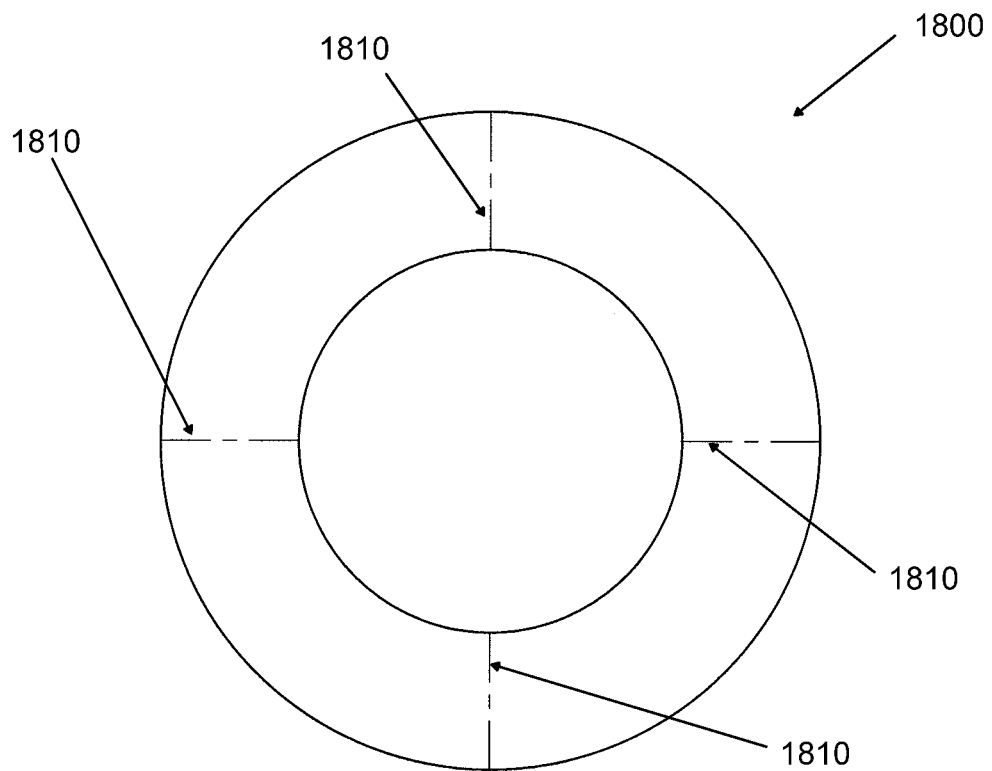
FIGS. 18A-B depict a top view (FIG. 18A) and side view (FIG. 18B) of a balloon 1800 showing the configuration of balloon seams 1810 for fabricating a balloon which resists bursting in vivo.
Figure 18B:
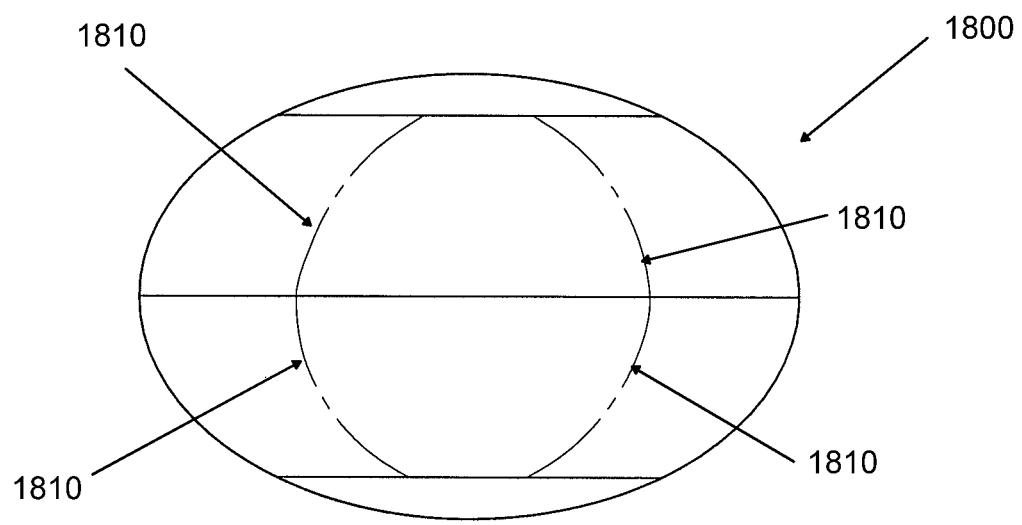

The valve can be adhered to the (e.g., polyethylene, PE) side of one of the hemispheres and protrude out of the opposite (e.g., nylon) side. One hemisphere typically consists of Nylon as the outermost layer and the second hemisphere typically has polyethylene (sealing web) as the outermost layer. The edges of the two hemispheres are preferably aligned such that they overlap by at least 1 mm and no more than 5 mm. Alignment and overlay of the two hemispheres is done to compensate for the thinning at the edges during the thermoforming process, which in turn inhibits seam bursts in vivo. Each half of the spheroid is placed on a fixture and the excess from the forming process is trimmed. On a multi-layer film, the sealing layer, a PE or similar layer is bonded to the sealing layer of the second film half. To do this the film of the hemisphere that has the nylon exposed to the external environment is folded up along the edges of the sphere on one half (see FIGS. 18A-B) such that it can be bonded to the hemisphere with the polyethylene on the outermost layer.

The two film pieces are then sealed using a roller bonder or a band heater. In the roller bonder, a pneumatic cylinder provides the compression, the heater provides the sealing heat, and a motor that moves the bonder around the area controls the time that is required to ensure proper sealing. In the band heater, there is a heating element, an expandable plug that provides the compression, and a timer. The band is a metal, preferably copper and a spool-like fixture provides the compression needed. Using film layers of different melt temperatures helps ensure integrity of the barrier layers of the final balloon configuration. If two similar materials are welded, then an insulator can be employed. In a preferred embodiment, one sphere is provided with the Nylon layer facing out and the second sphere has a PE layer facing out.

Balloons with Resistance to Spontaneous Deflation

The largest percentage of intragastric balloon malfunctions is due to spontaneous deflations. Spontaneous deflations can occur due to (1) external puncture of the intragastric balloon due to gastric motility forces, (2) over inflation of the balloon due to increased internal pressure of the balloon from uptake of the gastric environment of the gasses and water vapor and (3) under inflation of the balloon that leads to fatiguing of the excess material and subsequent puncture of the balloon. By managing these two variables and tuning these variables to withstand the dynamic gastric environment, the balloon system can be tailored to ensure it remains inflated throughout its useful life. Instances of spontaneous deflation in this intragastric balloon can be minimized by selection of the starting inflation gas in conjunction with selection of the composite wall materials and construction. Selection of the permeability characteristics with respect to water vapor transmission and gas permeability of the composite wall so as to take advantage of the properties of the gastric space contents can enable the rate of diffusion of gases into and out of the balloon to be controlled. This method allows for a tunable method for prevention of under inflation and over inflation.

Another phenomenon seen with gastric balloons and obesity in general is stomach accommodation. In the process of stomach accommodation, the stomach grows to accommodate the space occupying device or excess food that is ingested. In the process of stomach accommodation, the volume of a stomach containing an intragastric balloon grows over time, such that the patient becomes hungrier. However, by controlling gas diffusion and water vapor transmission across the balloon wall over time, the balloon size can also be increased over time by selecting the starting inflation gas(es) and water and other in vivo gas permeability characteristics of the film so as to maintain weight loss. In addition to spontaneous deflations, selecting the permeability characteristics of the composite wall in conjunction with the starting gases and utilizing the transfer of gases and water inside of the balloon from the gastric environment, the balloon can be designed to grow over its useful life in response to stomach accommodation.

Experiments were performed wherein various starting inflation gases were selected in conjunction with varying external gas environments that mimic the stomach gas and water environment in vivo. The stomach environment consists of water, acid (hydrochloric acid), a mixture of gases, and chyme (the semifluid mass of partly digested food expelled by the stomach into the duodenum). Stomach gas usually arises from swallowing air during eating. The composition of air is nitrogen ($N_2$) 78.084%; oxygen ($O_2$) 20.9476%; argon (Ar) 0.934%; carbon dioxide ($CO_2$) 0.0314%; neon (Ne) 0.001818%; methane ($CH_4$) 0.0002%; helium (He) 0.000524%; krypton (Kr) 0.000114%; hydrogen ($H_2$) 0.00005%; and xenon (Xe) 0.0000087%.

Five gases constitute greater than 99% of the gases in gastrointestinal system: $N_2$, $O_2$, $CO_2$, $H_2$ and methane, with nitrogen predominating. Gastric $pCO_2$ closely parallels local (splanchnic) arterial and draining venous blood $pCO_2$ values. Neutralization of stomach acid can also generate gas. For example, when the stomach acid reacts with bicarbonates (e.g., as are present in certain antacids) in the digestive juices, the chemical process creates $CO_2$, which is normally absorbed into the blood stream. Digestion of food in the intestines, mainly through fermentation by colonic bacteria, generates $CO_2$, $H_2$, and methane. Microbes appear to be the sole source of all of the hydrogen and methane produced in the intestine. These arise from fermentation and digestion of nutrients (polysaccharides from fruits and vegetables are not digested in the small intestines). Small quantities of a few other gases, including hydrogen sulfide, indoles, and ammonia can also be generated.

Controlled self-inflation of the intragastric balloon in the in vivo environment can be achieved by using a semipermeable or permeable composite wall in the balloon and initially filling the balloon with a preselected single gas, such as $N_2$ or $O_2$. The balloon utilizes differences in concentrations of gases and water concentration differences between the internal balloon environment and the external environment in vivo (GI/stomach) to increase and/or decrease the volume and/or pressure over time. To achieve a controlled decrease in volume and/or pressure, a wall can be employed that has a relatively higher permeability to the single gas used to inflate the balloon than to other gases present in the in vivo gastrointestinal environment. For example, if nitrogen gas is employed as the inflation gas, over time in the in vivo environment, the volume and/or pressure in the balloon will decrease as nitrogen diffuses out into the in vivo environment through the oxygen permeable wall. Similarly, if oxygen gas is employed as the inflation gas, over time in the in vivo environment, the volume and/or pressure in the balloon will decrease as oxygen diffuses out into the in vivo environment through the oxygen permeable wall. The differential in partial pressure of the single gas in the balloon (higher) versus the in vivo environment (lower) will drive the process until equilibrium or homeostasis is reached. To achieve a controlled increase in volume and/or pressure, a wall can be employed that has a relatively lower permeability to the single gas used to inflate the balloon than to other gases present in the in vivo gastrointestinal environment. For example, if nitrogen gas is employed as the inflation gas, over time in the in vivo environment, the volume and/or pressure in the balloon will increase as $CO_2$, etc. diffuses into the balloon through the $CO_2$ permeable wall. The differential in partial pressure of the permeable gas in the balloon (lower) versus the in vivo environment (higher) will drive the process until equilibrium is reached.

In addition, maintaining and/or controlling inflation of the balloon can also be done using the differences in concentrations between the internal balloon environment and external gastric environment in which the balloon volume/pressure can be increased or decreased as needed to extend the useful life of the product. One reason to decrease the pressure can be to first inflate the balloon with a large, but highly diffusible/soluble gas molecule such as $CO_2$ in addition to a more inert gas like nitrogen to pre-stretch the balloon, with the soluble gas diffusing out of the balloon and other gases not originally present in the balloon migrating in to fill the balloon.

Inflation gases can be selected to start with the majority of the gas in the balloon comprising a large, inert gas or a gas that has low diffusivity through the selected composite wall. An inert gas in conjunction with a less inert gas(es) that are more soluble in the gastric environment, can be combined to comprise the starting balloon inflation gas composition. Patient diet and medications can also affect/control balloon inflation status—primarily by $CO_2$ concentration effects produced in the gastric environment. In addition, gastric pH also affects $CO_2$ concentration. This particular method can also allow for a greater degree of tuning of the device's useful life based on the composite wall material, e.g., barrier/non-barrier and whether the gas that diffuses in is maintained longer in the balloon if it has a barrier wall versus a non-barrier wall. This particular form of self-inflation can be employed using a self-inflating gastric balloon (e.g., initially inflated by a gas generating reaction in the balloon initiated after swallowing), or an inflatable gastric balloon (e.g., inflated using a catheter, with or without endoscopic assistance, delivered naso-gastrically or any other delivery method). The method can be used with any gastric balloon, including swallowable balloons and balloons placed in the stomach by, e.g., endoscopic methods. The method is particularly preferred for use in connection with intragastric devices; however, it can also be applied to use in, e.g., pulmonary wedge catheters and urinary incontinence balloon devices. The advantages to this technology include the ability to compensate for stomach accommodation, allowing the balloon to adapt to a stomach that may increase in volume over time, thereby maintaining patient satiety. It also permits starting with a smaller amount of inflation gas constituents for a self-inflating balloon. It can prevent spontaneous deflations by utilizing diffusion gradients between gastric balloon systems and the in vivo gastric environment.

In a particularly preferred embodiment, used in connection with $N_2$ (with or without $CO_2$) as the inflation agent, a multi-layer co-extruded blend for the wall layers is employed. A particularly preferred configuration is Nylon 12/Ethyl Methyl Acrylate/Polyvinylidene Chloride/Ethyl Methyl Acrylate/Nylon 12/Linear Low Density Polyethylene+Low Density Polyethylene (also referred to as co-extruded Nylon 12-encapsulated PVDC-Nylon 12-LLDPE+LDPE multilayer). Another particularly preferred configuration is a co-extruded multi-layer Nylon 12/Linear Low Density Polyethylene+Low Density Polyethylene. Selection of the resins for the composite wall construction (as well as selection of using a coextrusion method or adhesives) can be varied to control compliance (stretchiness), puncture resistance, thickness, adhesion, sealing bond strength, orientation, acid resistance, and permeability characteristics to gasses and water vapor to achieve a particular effect.

Automatic Deflation of Intragastric Balloon Systems

The self-inflating (also referred to as automatic inflating) or inflatable (also referred to as manually inflating) intragastric balloon is provided with mechanisms to reliably control timing of deflation. In preferred embodiments, the balloon auto-deflates and passes through the stomach, through the lower gastrointestinal tract, and out of the body at the end of its pre-determined useful life (non-spontaneous), preferably between 30 and 90 days but can be timed to deflate within 6 months. In the preferred embodiments described below, the timing of deflation can be accomplished via the external gastric environment (by conditions of temperature, humidity, solubility, and/or pH, for example) or via the environment within the lumen of the inflated balloon. It is preferable for consistency to control the initiation of the self-deflation process by manipulating the internal balloon environment.

In other embodiments, the patch applied to allow for inverted seams as described above and/or one or more additional patches or other structures added to the balloon construction are made out of an erodible, degradable, or dissolvable material (natural or synthetic) and are incorporated into the wall of the balloon. The patch(s) are of sufficient size to ensure opening of a sufficient surface area to cause rapid deflation, and to prevent re-inflation by seepage of stomach fluid into the balloon. The balloon patch(s) comprise materials that can be applied to the balloon such that a substantially smooth surface is maintained, and preferably comprise a single layer or multi-layered material. The patch(s) are constructed using an erodible, disintegrable, degradable or other such material that is preferably tissue-compatible and degrades into non-toxic products or is a material that slowly hydrolyzes and/or dissolves over time (e.g., poly(lactic-co-glycolic acid) (PLGA), poly(lactide-co-glycolide) (PLG), polyglycolic acid (PGA), polycaprolactone (PCL), polyesteramide (PEA), polyhydroxyalkanoate (PHBV), polybutylene succinate adipate (PB SA), aromatic copolyesters (PBAT), poly (lactide-co-caprolactone) (PLCL), polyvinyl alcohol (PVOH), polylactic acid (PLA), poly-L-lactic acid PLAA, pullulan, polyethylene glycol (PEG), polyanhydrides, polyorthoesters, polyaryletherketones (PEEK), multi-block polyetheresters, poliglecaprone, polydioxanone, polytrimethylene carbonate, and other similar materials). These erodible, disintegrable, or degradable materials can be used alone, or in combination with other materials, or can be cast into/co-extruded, laminated, and/or dip coated in conjunction with non-erodible polymers (e.g., PET or the like) and employed in the construction of the balloon. Degradation/erosion occurs, is initiated by, and/or is controlled by the gastric environment (e.g., by conditions of temperature, humidity, solubility, and/or pH, for example), or is controlled within the lumen of the balloon (e.g., by conditions of humidity and/or derived pH, for example) based on what the patch is exposed to. Thickness of the polymer as well as environment which affects degradation and time of exposure can also facilitate degradation timing. Degradation/erosion are timed such that they occur once the pre-determined balloon useful life is completed (e.g., inflation is maintained for from 25 to 90 days in vivo in the stomach before degradation/erosion results in formation of an opening permitting deflation). As an alternative to (or in connection with) using an degradable material for the patch, the patch can comprise a similar fluid retention barrier film or the same film as the remaining wall of the balloon which is adhered to the balloon using a weak adhesive, or welded or adhered such that after a specified amount of time the patch delaminates from the applied area and allows for an opening for inflation fluid release for deflation. Or if deemed necessary for rapid deflation the entire balloon composite wall can be made of the erodible material. The mechanism of using an erodible material or a material that mechanically fails after a pre-specified time is be similar for all embodiments for deflation mechanisms described below as well. The timing of degradation or erosion can be controlled using the external gastric environment (e.g., by conditions of temperature, humidity, solubility, and/or pH, for example) and/or can be controlled by conditions within the lumen of the balloon (e.g., by conditions of humidity and/or pH of residual liquid in the balloon).

Figure 19A:
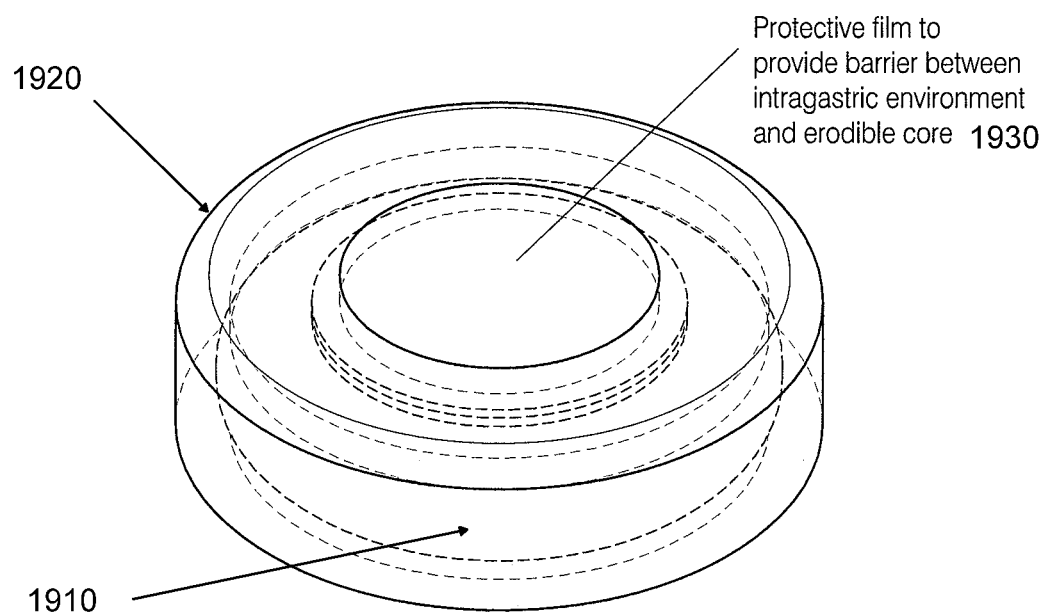
FIGS. 19A-D depict various embodiments of an eroding core 1910 to achieve deflation of a balloon (not depicted).
Figure 19B:
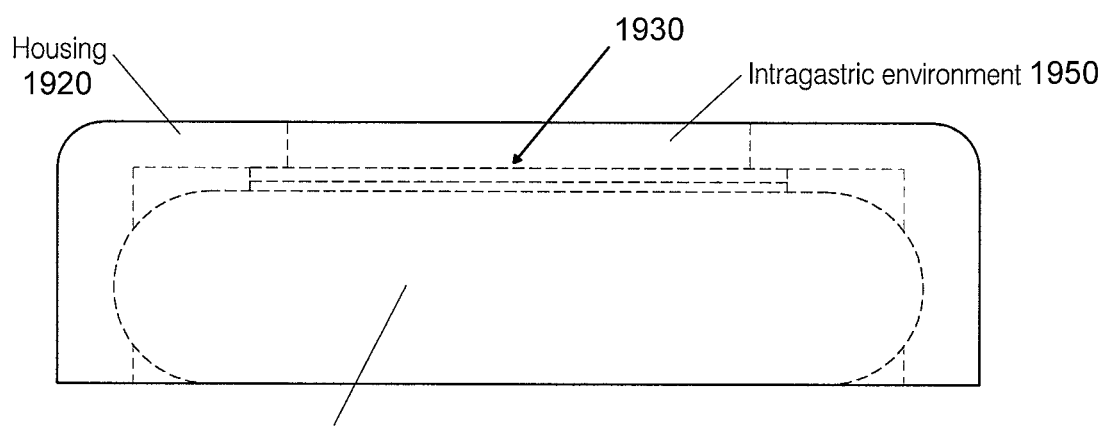
Figure 19C:
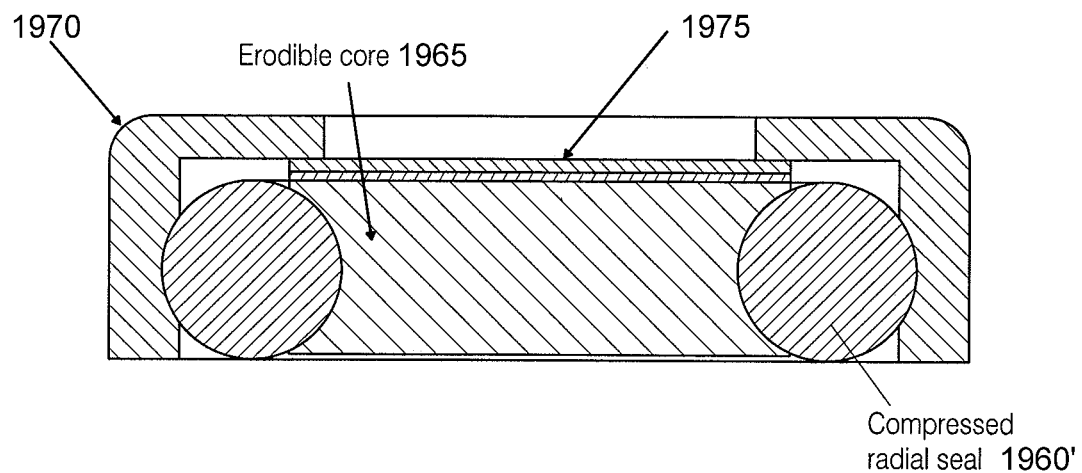
Figure 19D:
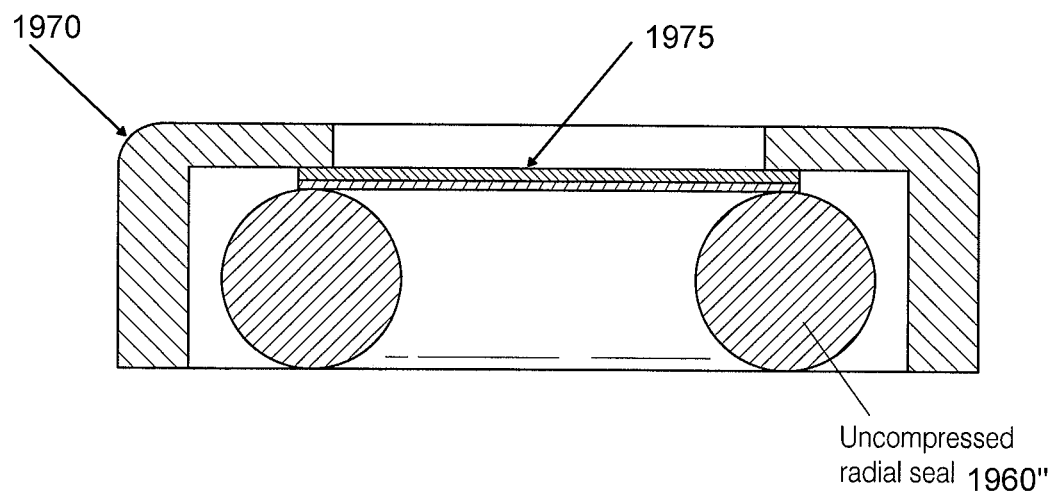
Figure 20:
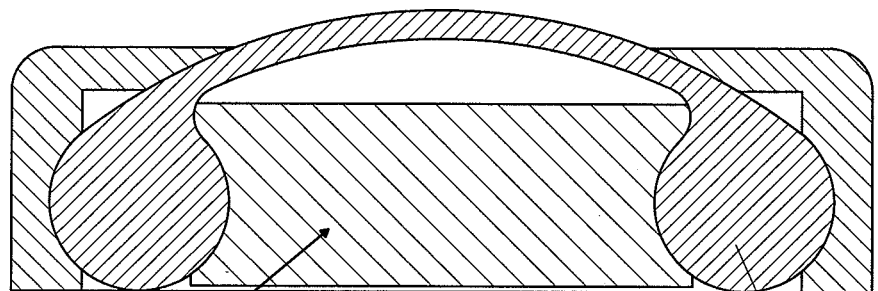
FIG. 20 depicts a one-piece seal with protective canopy 2010 held in place by an erodible core 2020.
Figure 21A:
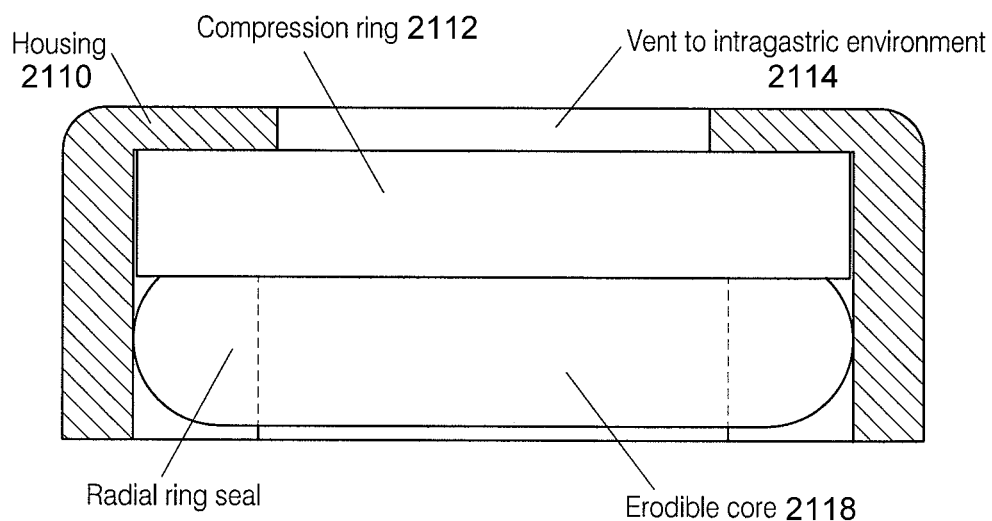
FIG. 21A depicts a deflation mechanism utilizing an erodible core 2118 in a radial ring seal 2116, with compression ring 2112 to expel the seal 2116 once support from the erodible core 2118 is removed. The mechanism further includes a housing 2110 and a vent 2114 to the intragastric environment.

In other embodiments, a plug or plugs (optionally in conjunction another degradable retaining structure) can be incorporated into the balloon construction and can consist, all or in part, of an erodible, disintegrable, or otherwise degradable synthetic or natural polymer similar to those described above (e.g., PLGA, PLAA, PEG, or the like). The plug can be formed into various shapes (e.g., cylinder shape or radial shape, as depicted in FIGS. 19A-D) to achieve various surface-to-volume ratios so as to provide a preselected and predictable bulk degradation pattern for the erodible polymer. The plug can incorporate a releasing mechanism that can be chemically initiated after degradation/erosion begins, such that the septum or plug material pops out of the balloon or falls inside of the balloon, thereby creating a passageway for fluid release and subsequent deflation of the balloon. Mechanical additions that can be used in conjunction with a plug include a degradable/erodible/disintegrable material that holds a plug (e.g., of a non-degradable or degradable material) in place or a compressed spring housed within the retaining structure or plug structure. More specifically one preferred embodiment to achieve deflation can comprise a housing, a radial seal, a solid eroding core, and a protective film attached to the external surface of the eroding core (FIGS. 19A-B). The inside of the eroding core is exposed to the internal balloon liquid. The core creates a compressive force that holds the seal against the housing. As the core erodes, the compression between the housing and the radial seal is reduced until there is clearance between the housing and the seal. Once there is clearance, gas can move freely from the inside of the balloon to the outside environment (FIG. 21A). The seal can fall out of the housing and into the balloon. The diameter, length, and material types can be adjusted in order to create the deflation at a desired time point. Example materials for each component used to achieve this deflation mechanism can be as follows. Housing—biocompatible structural material, capable of withstanding enough radial force to form an air tight seal. Materials can include polyethylene, polypropylene, polyurethane, UHMWPE, titanium, stainless steel, cobalt chrome, PEEK, or nylon. Radial Seal—composed of a biocompatible elastic material, capable of providing liquid and gas barrier to acidic environments. Materials can include silicon, polyurethane, and latex. Eroding Core—a material capable of breaking down at a predictable rate at given environmental conditions. Materials can include PLGA, PLA, or other polyanhydrides that are capable of losing integrity over time or any materials listed above that provide erodible characteristics.

Figure 21B:
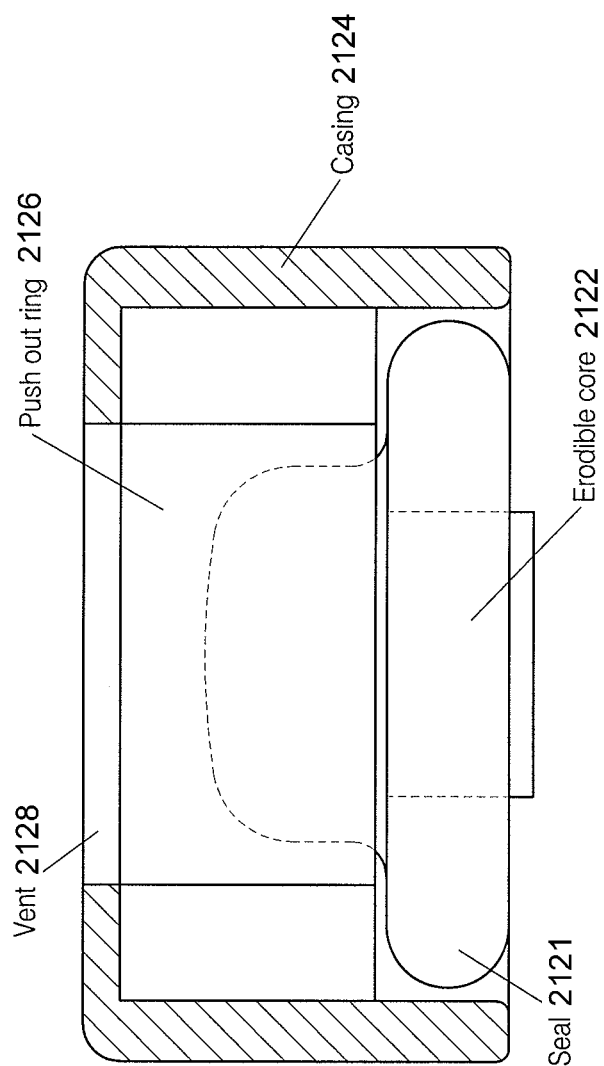
FIG. 21B depicts a deflation mechanism utilizing a seal 2121 with erodible core 2122 and a push out ring 2126, held in a casing 2124 having a vent 2128 to the intragastric environment.

For the spring mechanism, once the material degrades, the spring is released and/or the plug/septum is pulled into the balloon or pushed out of the balloon, thus releasing fluid once an orifice has been created by release of the spring mechanism and pushing out or pulling in of the plug (FIG. 21B).

Figure 21C:
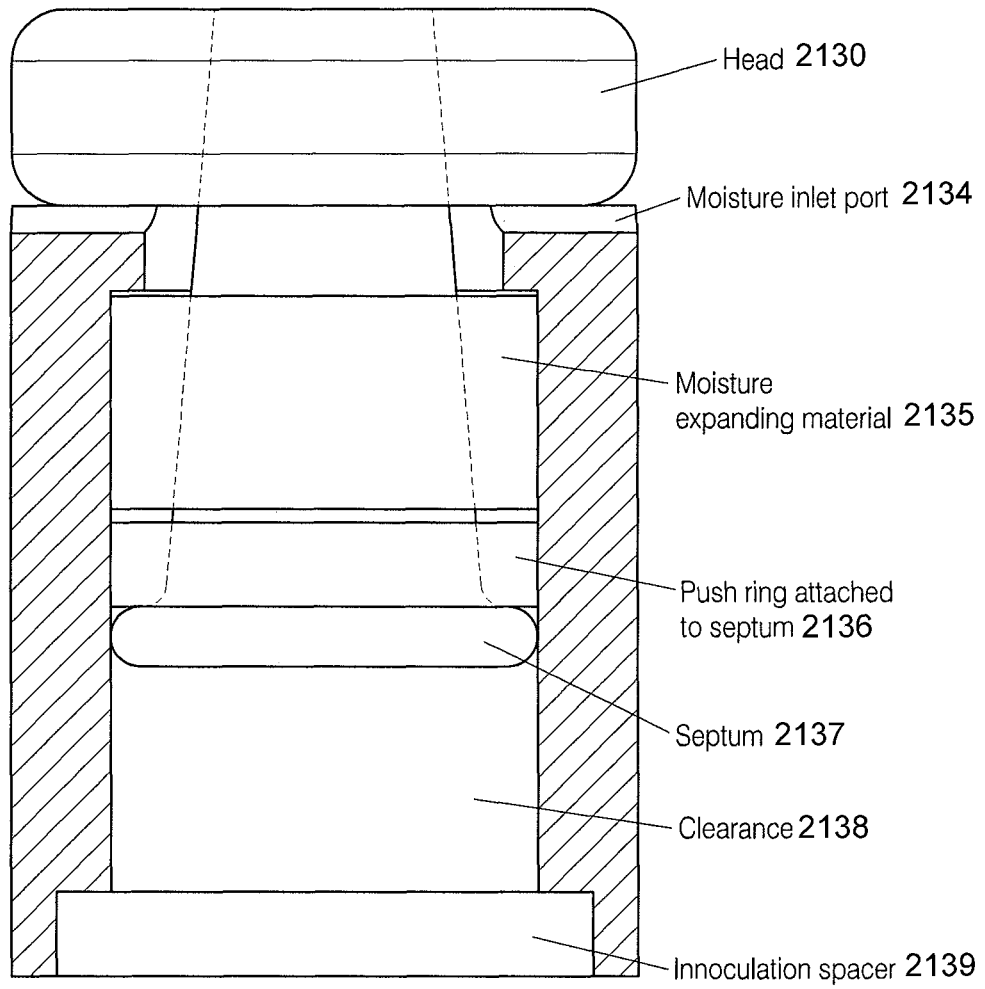
FIG. 21C depicts a moisture expanding material 2135 that pulls the septum 2137 out of position to cause balloon deflation. The mechanism further includes a head 2130, moisture inlet port 2134, push ring attached to septum 2136, clearance 2138, and inoculation spacer 2139.

Deflation mechanisms utilizing a septum and moisture absorbing expansion material and a moisture eroding material. The eroding materials slowly erode away when exposed to moisture, eventually exposing the moisture absorbing expansion material. When the moisture expanding material begins to absorb moisture, the expansion pulls the septum out of position in the head by pushing against a septum lip or a ring attached to the septum. Pulling the septum out of position causes an immediate deflation of the balloon (FIG. 21C). In order to protect the expanding material from moisture until a desired timepoint, the expanding material can be sheathed in water blocking materials, such as parylene, as well as slowly water degrading materials. The moisture contact can be controlled by small inlet ports. The inlet ports can be small holes, or a wick material that draws moisture in a controlled manner. The desired deflation time is achieved through a combination of eroding materials, blocking materials, and inlet port sizing.

Figure 22A:
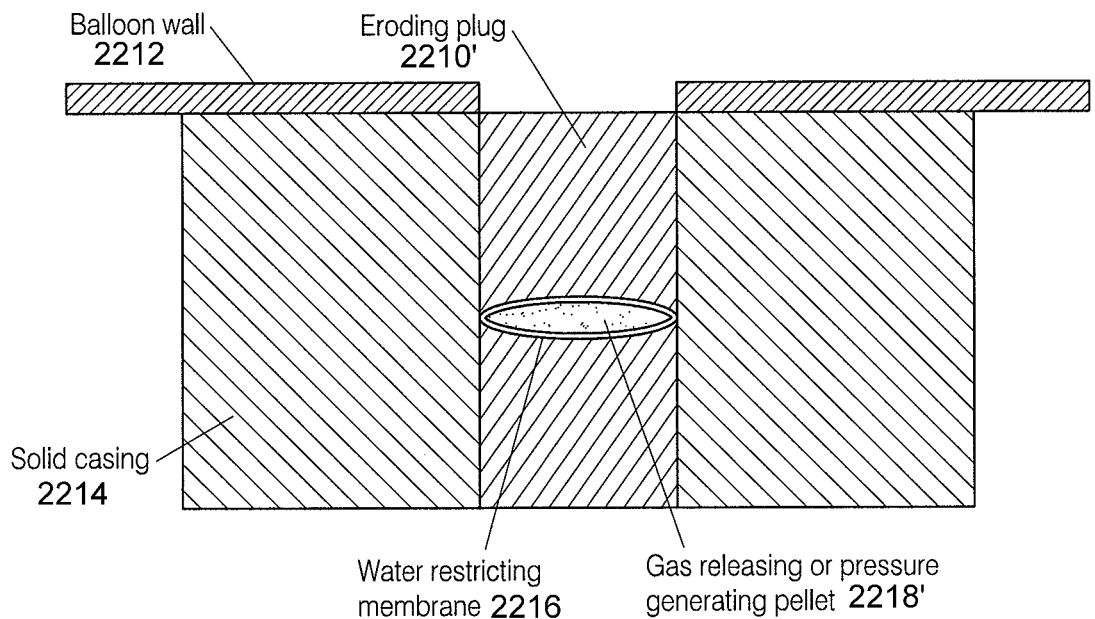
FIGS. 22A-B depicts an eroding plug 2210' in the wall 2212 of the balloon that contains a compressed pellet or gas releasing pellet 2218'.
Figure 22B:
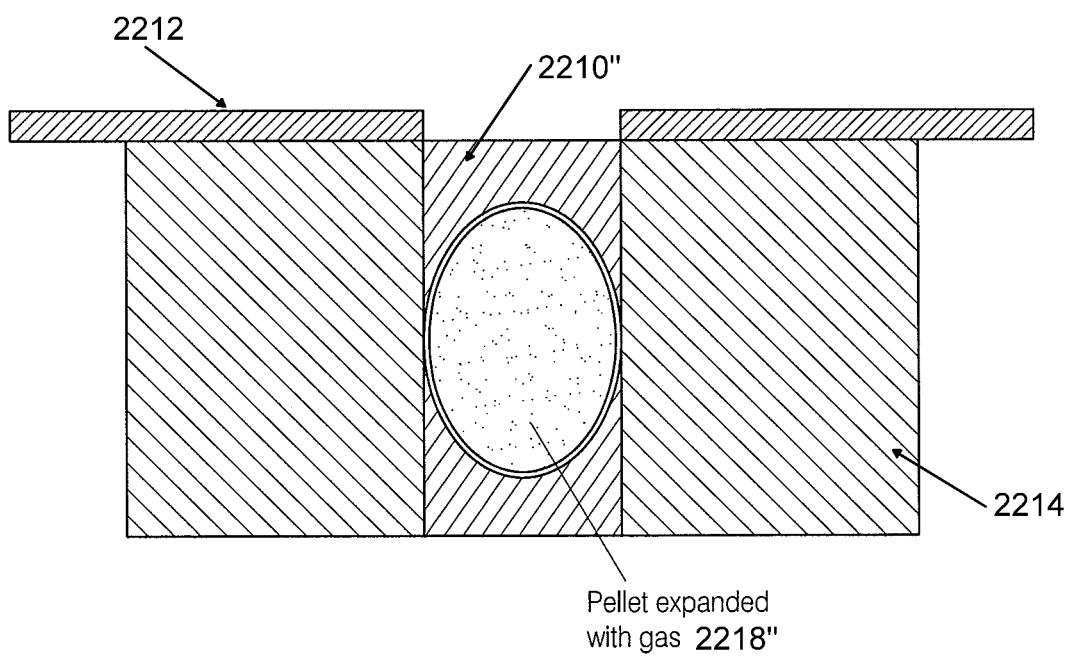

In certain embodiments, the balloon can incorporate one or more plugs in the wall of the balloon that contain a compressed pellet (FIGS. 22A-B) or gas releasing pellet. The pellet can be comprised of any combination of constituents that, when activated, emit $CO_2$ gas (e.g., sodium bicarbonate and citric acid, or potassium bicarbonate and citric acid, or the like). The pellet can be in tablet or rod form protected by an erodible, disintegrable, or degradable material that is preferably tissue-compatible and degrades into non-toxic products or that slowly hydrolyzes and/or dissolves similarly to the plugs and patches described above (e.g., poly(lactic-co-glycolic acid) (PLGA), polyvinyl alcohol (PVOH), polylactic acid (PLA), poly-L-lactic acid PLAA, Pullulan, Polyethylene Glycol, polyanhydrides, polyorthoesters, polyaryletherketones (PEEK), multi-block polyetheresters, poliglecaprone, polydioxanone, polytrimethylene carbonate, and other like materials). Degradation/erosion of the plug initiates the reaction of the two chemicals in the pellet and subsequently leads to formation of gas (e.g., $CO_2$). As sufficient gas is trapped or built up, sufficient pressure is eventually generated to push out the softened polymer material and create a larger channel for the $CO_2$ gas in the balloon to escape. External pressure applied by the stomach to the balloon (e.g., squeezing) can contribute to the process of creating a larger channel. Dimensions and properties of the plug (diameter, thickness, composition, molecular weight, etc.) comprised of the polymer drives the timing of degradation.

In other embodiments, plugs or patches of different shapes or sizes similar to those of the plugs described above can be employed within the balloon lumen in a multi-layer configuration including a semi-permeable membrane to facilitate balloon deflation. The plug or patch is made of similar degradable/erodible/dissolvable material as described above (e.g., poly(lactic-co-glycolic acid) (PLGA), polyvinyl alcohol (PVOH), polylactic acid (PLA), PLAA, pullulan, and other like materials) and contains a compartment enclosed by a semi-permeable membrane (impermeable to an osmolyte) that contains a concentrated solution of a solute or osmolyte (such as glucose, sucrose, other sugars, salts, or combination thereof). Once the plug or patch begins to degrade or erode, the water molecules move by osmosis down the water gradient from the region of greater water concentration to the region of lower water concentration across the semi-permeable membrane into the hypertonic solution in the compartment. The compartment containing the osmolyte swells and eventually bursts, pushing the membranes and the degraded plug or patch out, thereby allowing rapid gas loss through the newly created channels or areas.

In certain embodiments, a balloon composed of a septum, moisture eroding material inside an inlet port, and moisture absorbing expansion material is employed. The eroding materials slowly erode away when exposed to moisture, eventually exposing the moisture absorbing expansion material. When the moisture expanding material begins to absorb moisture, the expansion pulls the septum out of position in the head by pushing against a septum lip or a ring attached to the septum. Pulling the septum out of position causes an immediate deflation of the balloon. In order to protect the expanding material from moisture until a desired time point has been reached, the expanding material can be sheathed in water blocking materials, such as parylene, as well as slowly water degrading materials. The moisture contact can be controlled by small inlet ports. The inlet ports can be small holes, or a wick material that draws moisture in a controlled manner. The desired deflation time is achieved through a combination of eroding materials, blocking materials, and inlet port sizing.

Figure 23:
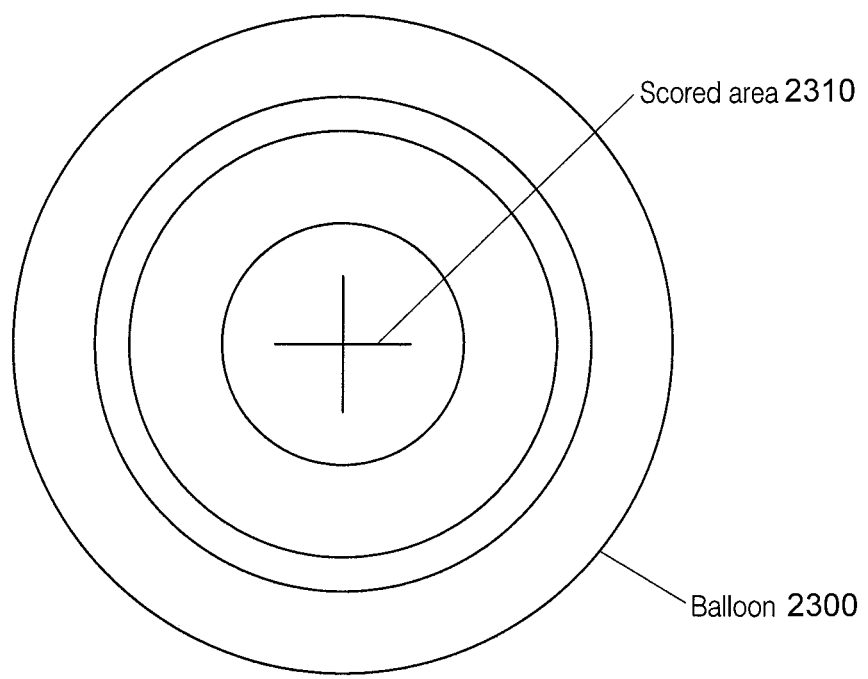
FIG. 23 depicts a top view of an outermost layer of a balloon 2300 "scored" or hatched with erodible material to create small channels 2310 that erode over time.
Figure 24A:
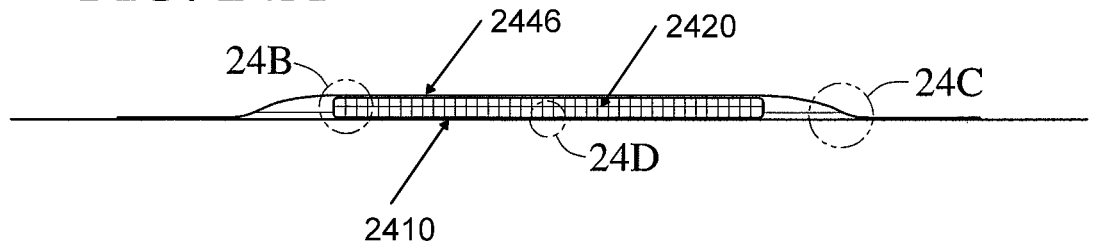
FIGS. 24A-E depicts a composite wall of a balloon including several material layers (FIG. 24A and FIG. 24B, showing detail of FIG. 24A) that are slowly penetrated by water that has been injected inside the balloon during the manufacturing process or during the inflation process, causing expansion of a water expanding material 2420 in a parylene coating 2430 situated adjacent to the polymeric wall 2410 of the balloon, in turn causing rupture of a thin external protective later 2446 (FIG. 24C). The water can penetrate through a hole 2460 (FIG. 24D) in the parylene coating 2430 and balloon material 2410 and the balloon can include a weakened area of a patch bond 2470 to control the rupture location (FIG. 24E).
Figure 24B:
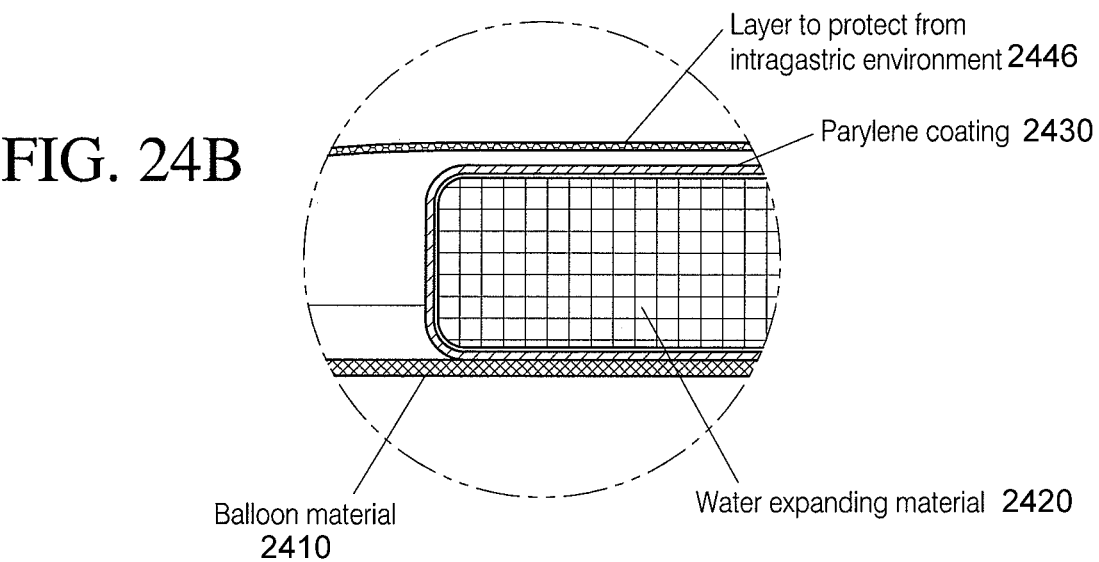
Figure 24C:
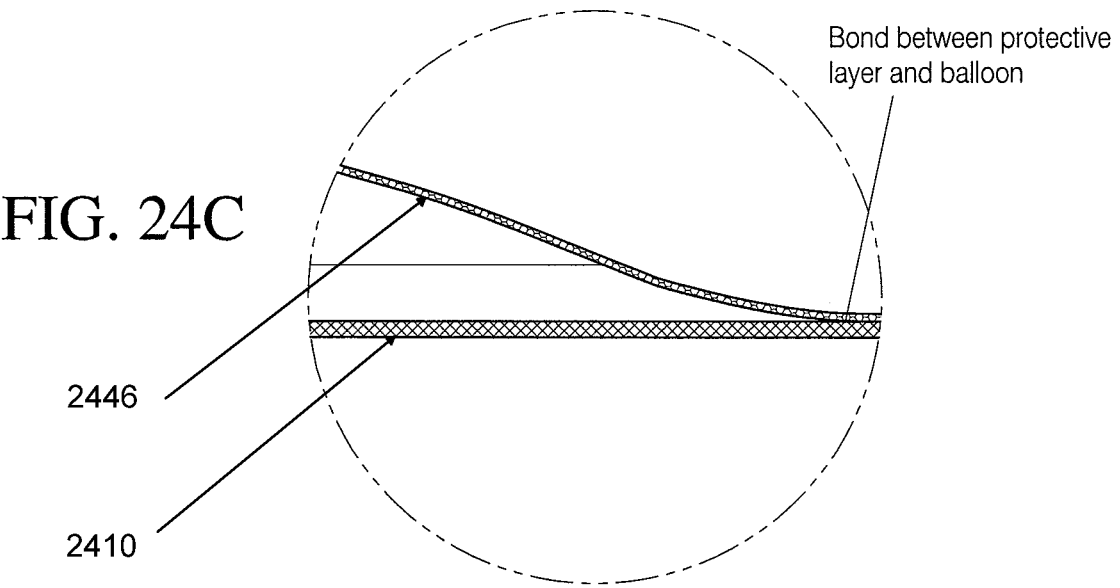
Figure 24D:
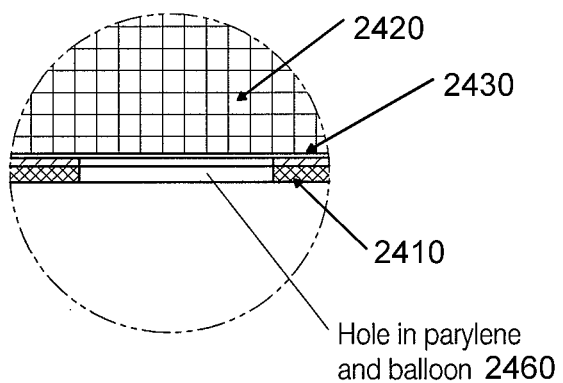
Figure 24E:
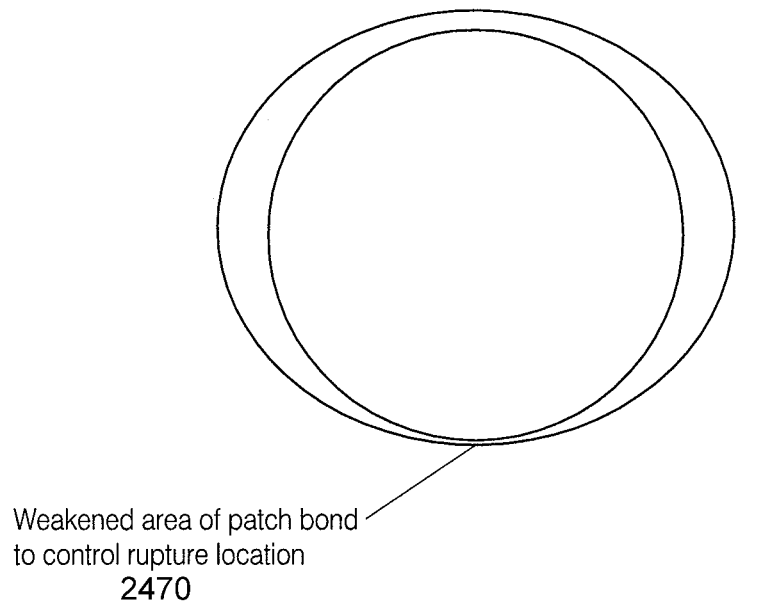

Another mechanism for self-deflation is to create a forced de-lamination scheme, which can provide a larger surface area to ensure rapid deflation. In, e.g., a balloon having a tri-layer wall, the outermost layer is substantially strong enough to hold the inflation fluid (e.g., polyethylene terephthalate (PET) or the like), the middle layer is comprised entirely of an erodible material (e.g., PVOH or the like) while the inner layer is comprised of a weaker material (e.g., polyethylene (PE) or the like). The PET or outermost layer is "scored" or hatched with erodible material to create small channels that erode over time (FIG. 23). This creates channels such that the gastric fluid seeps into the balloon layers and starts degrading the fully erodible material. When the erodible layer degrades or dissolves, the material that composes the innermost layer also erodes, degrades or dissolves since it is not strong enough to withstand the gastric forces/environment on its own. The balloon then collapses on itself and eventually passes through the lower gastrointestinal tract. Having an erodible layer sandwiched between a strong and weak layer facilitates timing of erosion by creating a longer path length than an erodible plug or patch affected by the gastric environment. The distance between scores or openings can also be selected so as to provide a desired deflation rate.

In another embodiment providing abrupt deflation of the balloon after a desired period of time has elapsed, the composite wall of the entire balloon or a section of the composite wall (patch) includes several material layers that are slowly penetrated by water that has been injected inside the balloon during the manufacturing process or during the inflation process (FIGS. 24A-E). This water penetrates through the layers, eventually reaching a material that substantially expands, rupturing a thin external protective later, and creating a large hole (FIG. 24D) for gas to escape and the balloon to deflate. The water expanding material is protected from liquid via a coating or sheath, such as parylene, which allows a controllable amount of moisture exposure. Once water reaches the expansion material, it exerts a force on the protective outer layer, causing it to rupture. The outer layer may be created with a weakened bonding area (FIG. 24E), a partially scored area, or other methods of ensuring a desired rupture location and to facilitate desired timing for auto-deflation to take place. There can be any number of layers between the moist environment and the moisture expanding center. Each material layer can have different erosion rates (e.g., fast or slow) and can be selected by the predetermined time deflation is desired to occur (e.g., after 30 days, 60 days, or more). By varying the number, thickness, and rate of each of the circumferential layers, the time to deflation can be accurately controlled.

Figure 25A:
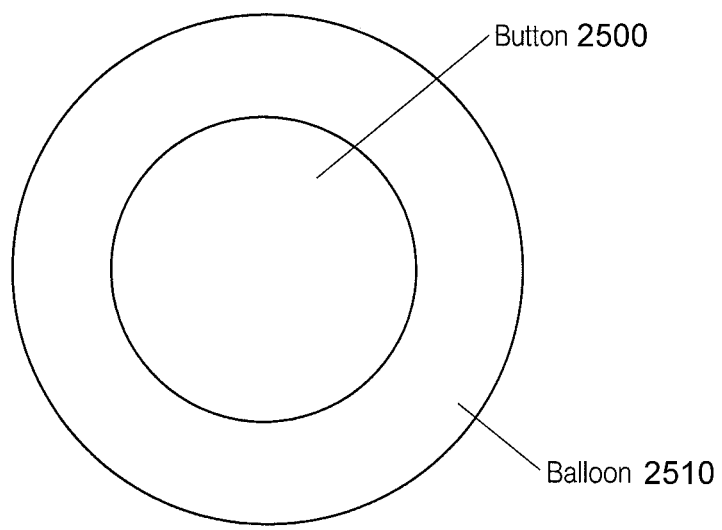
FIGS. 25A-B depict a top view (FIG. 25A) and a cross section (FIG. 25B) of a pressure sealing button 2500 that is adhesively bonded over a perforation acting as a water access hole 2514 in the balloon material 2510 for deflation. The button 2500 can be sealed in place using an adhesive 2512.
Figure 25B:
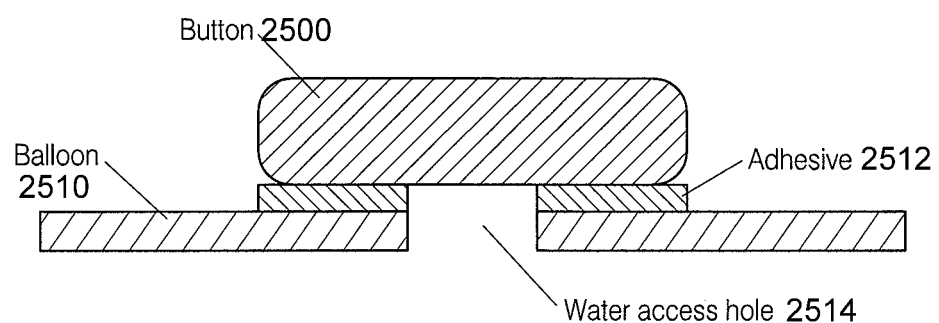

Alternatively a pressure sealing button that is adhesively bonded over a perforation in the balloon material can be provided for deflation (FIGS. 25A and B). The adhesive bonding the button erodes over time when it comes into contact with moisture derived from the gastric fluid or that has been injected inside the balloon. Once the adhesive can no longer bond and create an airtight seal between the adhesive and the button, the balloon will rapidly deflate. By controlling the hole size and moisture exposure of the adhesive, the erosion time can be accurately predicted.

Figure 26A:
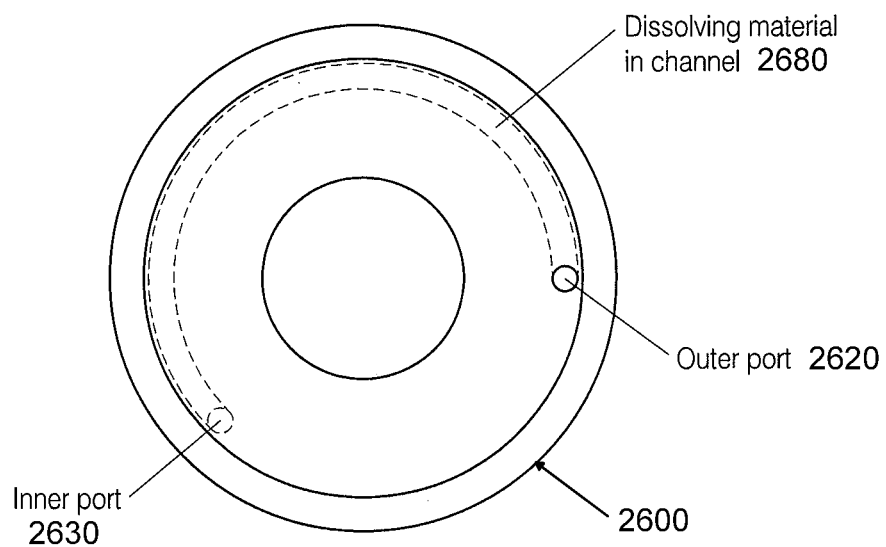
FIGS. 26A-B depicts a top view (FIG. 26A), perspective view (FIG. 26B) and perspective view with inner detail (FIG. 26C) of connecting ports within a septum 2610 in a head 2600 attached to the balloon composite wall (not depicted), wherein the ports contain a water-dissolving or acid-dissolving material 2680, and include an inner port 2630 and an outer port 2620. A plurality of internal ports 2640 and channels can be provided in a configuration utilizing an expanding material 2690 and push-out component 2670 as depicted in the system of FIG. 26D (perspective view with inner detail) and FIG. 26E (cross-section including seal 2694, balloon wall 2696 attached to casing 2698, expanding material 2690, push out component 2670, and external port 2699).
Figure 26B:
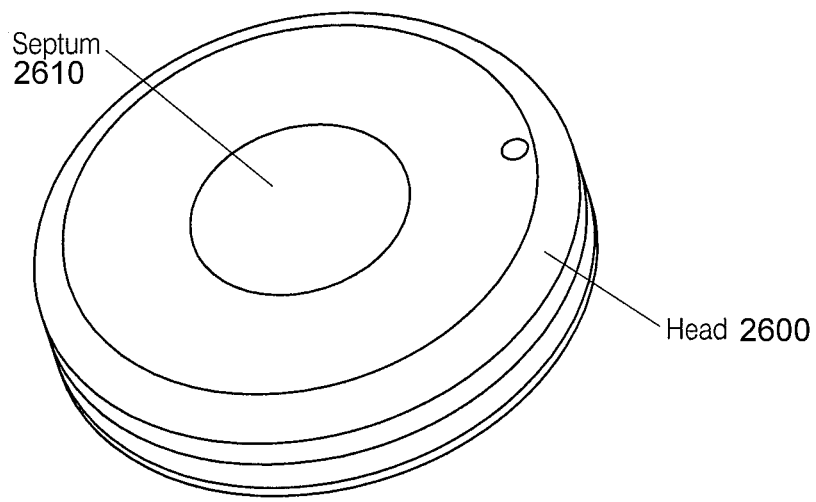
Figure 26C:
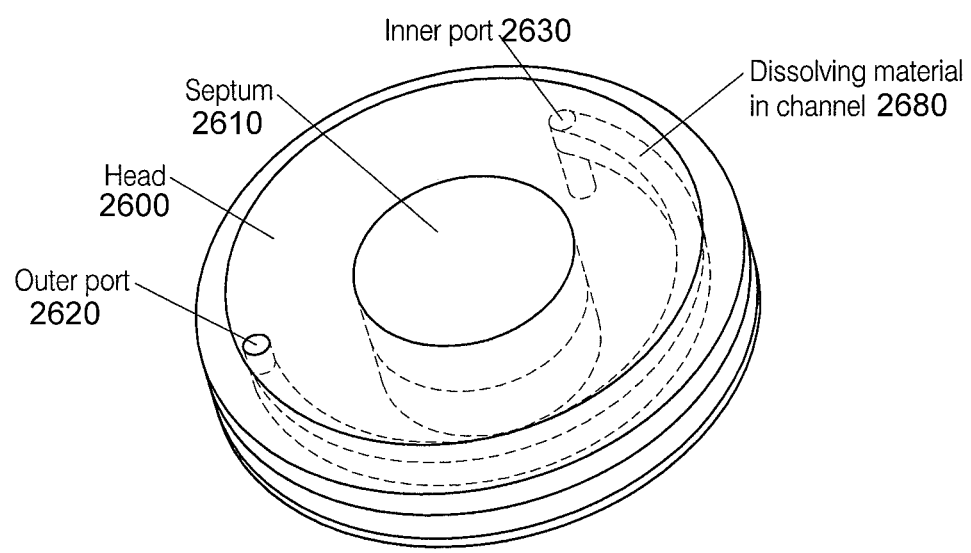
Figure 26D:
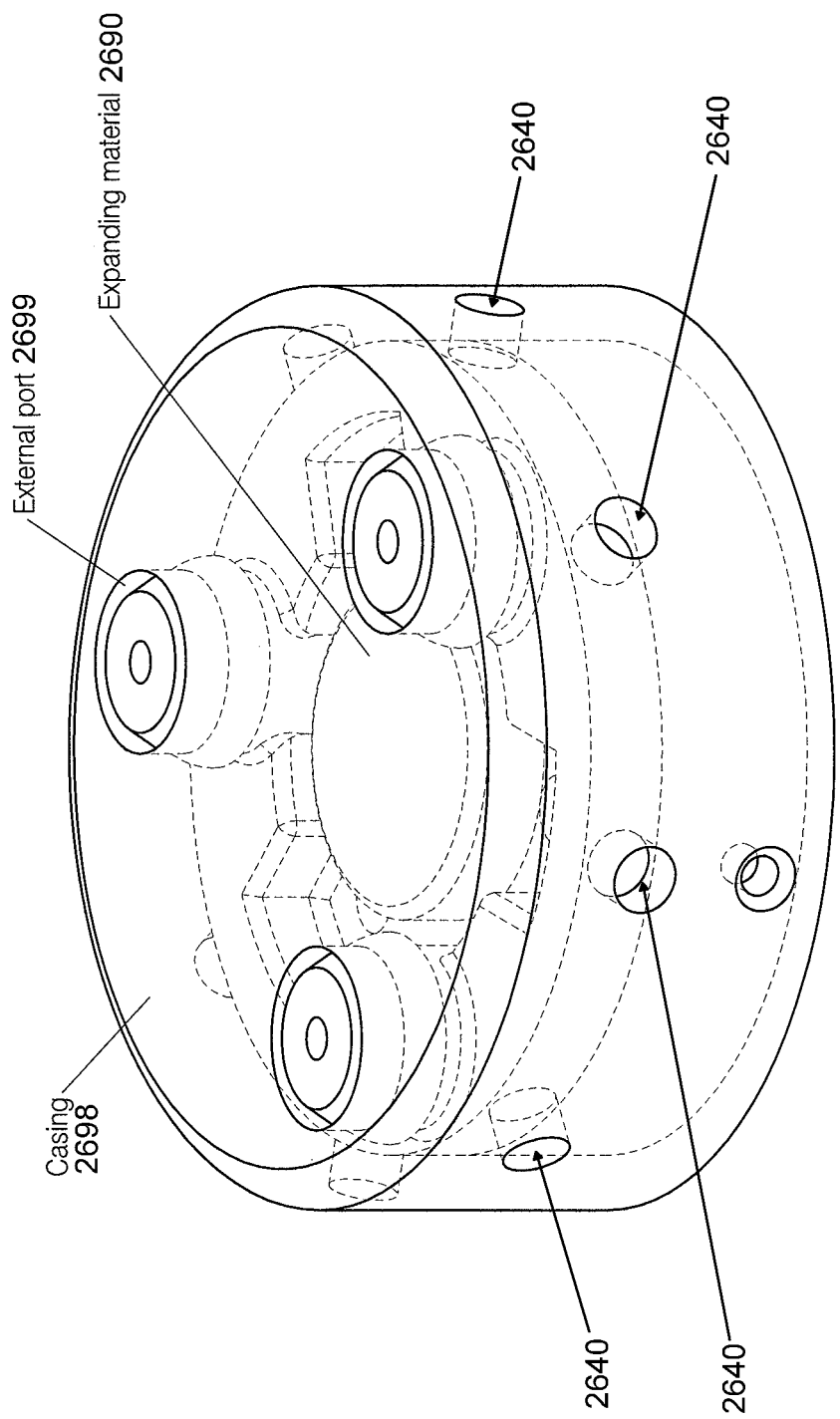
Figure 26E:
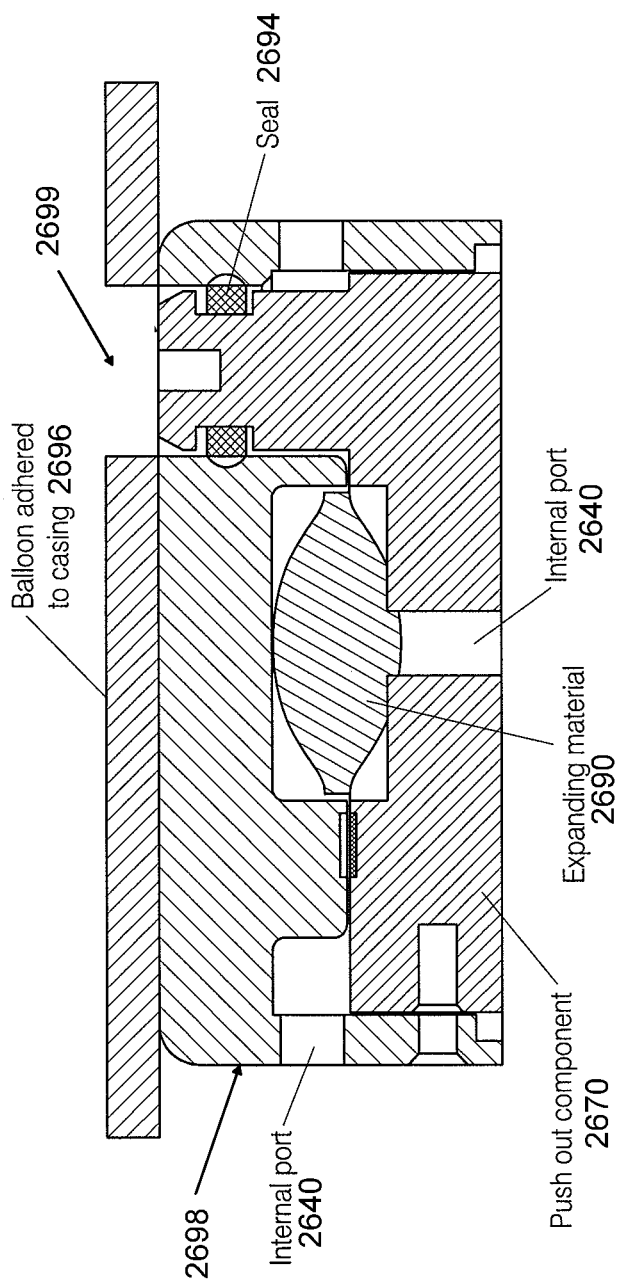

Deflation can also be facilitated by creating a series of connecting ports within the septum or on another similar structure attached to the balloon composite wall. The ports can be constructed using a water-dissolving or acid-dissolving, biologically compatible, low permeability substance, such as gelatin (FIG. 26A-B). The diameter of the hole, number of holes, channel width, and channel length can all be adjusted to control the dissolving parameters. Once the material in the ports and channel is dissolved, there is a clear path for gas trapped in the balloon to escape, eventually resulting in a deflated balloon. The water can be gastric fluid or controlled internally by including water inside the balloon at assembly or during the inflation process. There can be a plurality of port openings to guarantee gas transmits. Additionally, there are several variables that can be adjusted to control dissolution time: size of the port openings; number of port openings; the length of the internal channel; the width of the internal channel; and the rate of material dissolution. The port/channel layout design can ensure that only a small amount of surface area is exposed to moisture at any particular time, thereby controlling the rate of erosion and ultimately deflation. In an alternative embodiment, depicted in FIGS. 26D-E, an expandable material is employed to displace a push out component so as to initiate deflation.

Figure 27A:
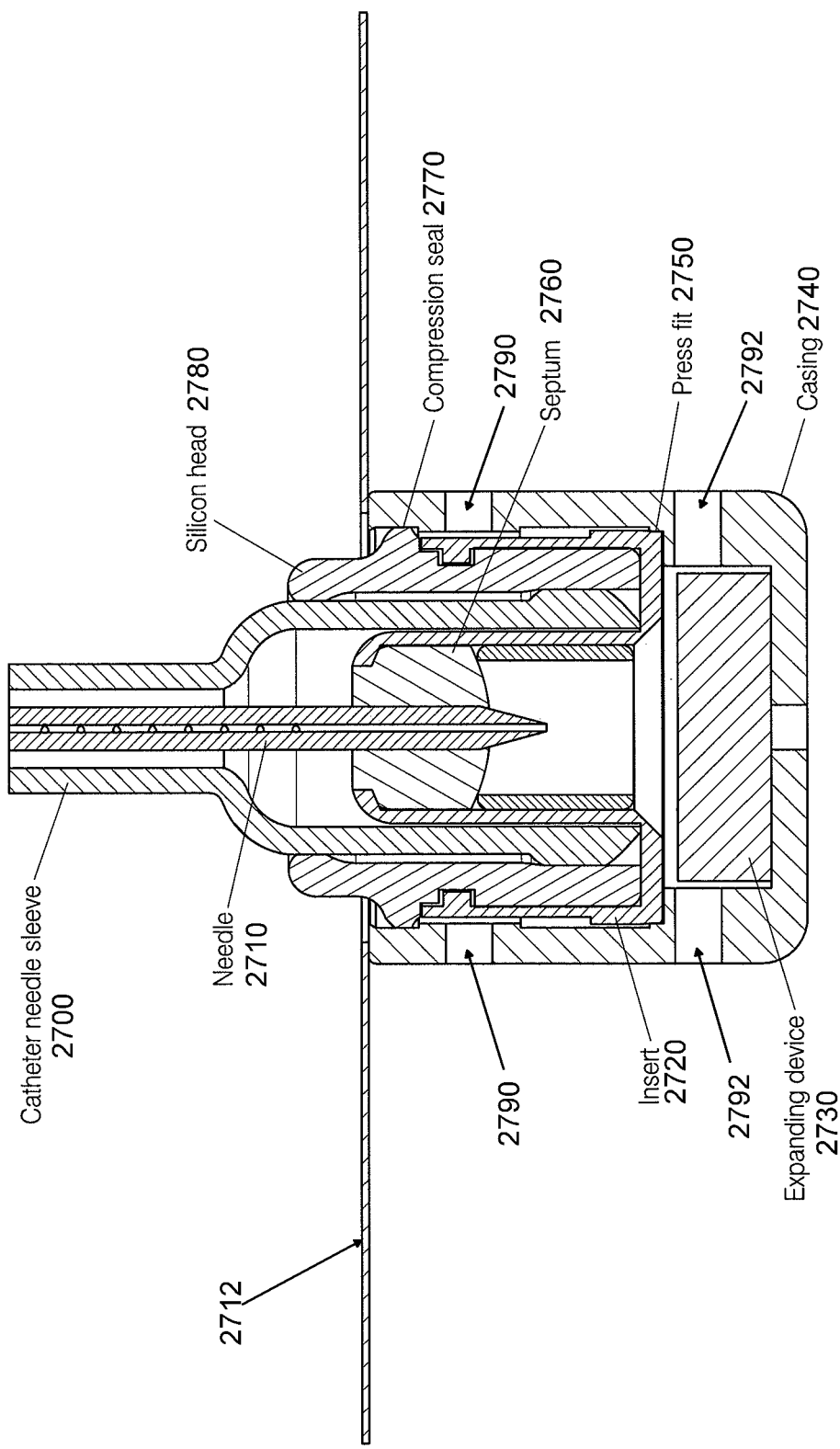
FIGS. 27A-D depicts a port that encompasses an inflation and deflation mechanism in the same location.
Figure 27B:
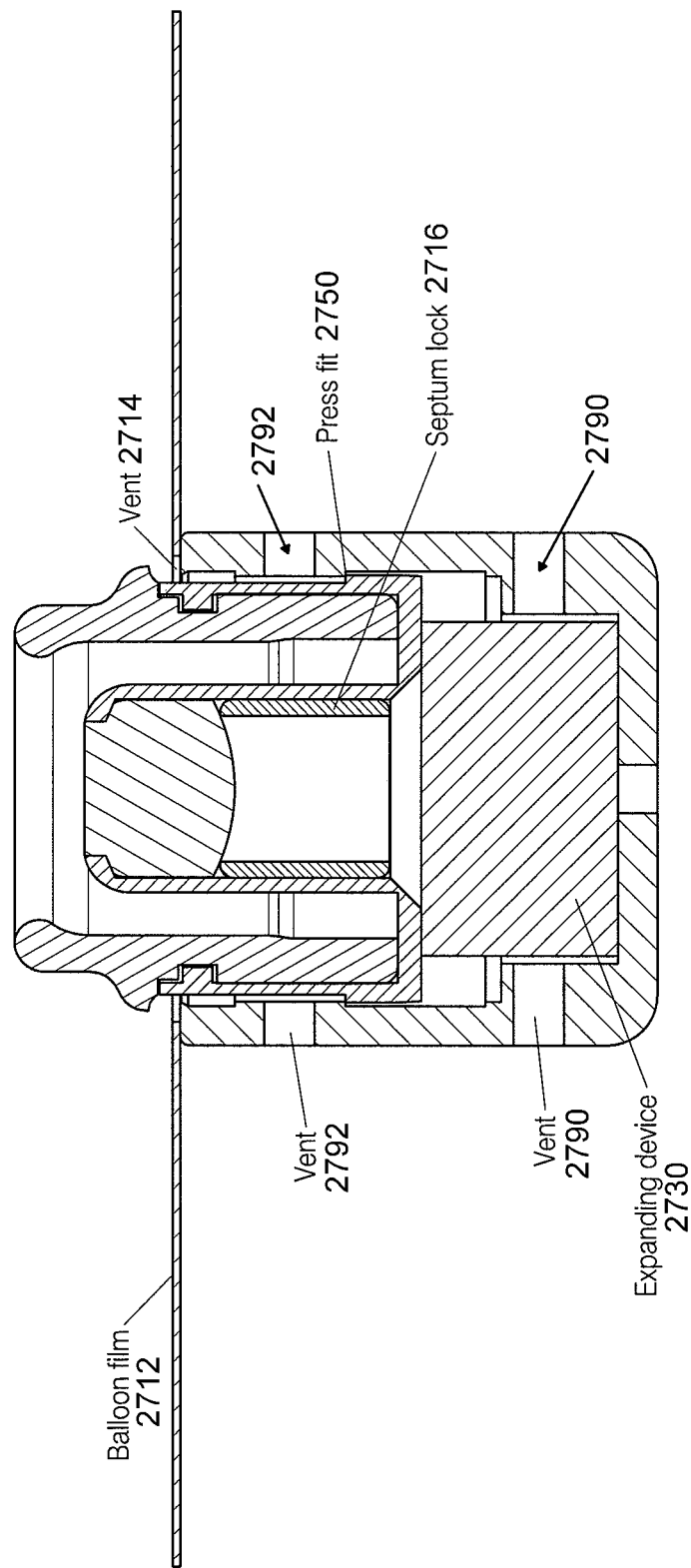
Figure 27C:
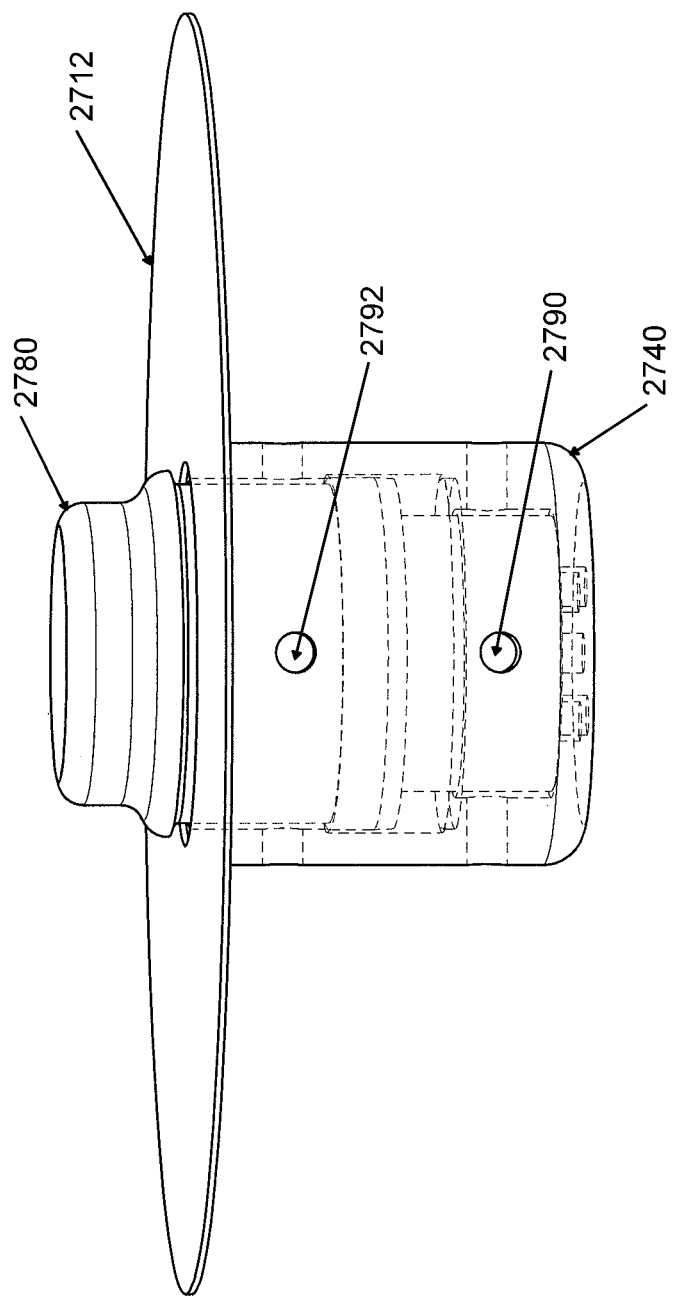
Figure 27D:
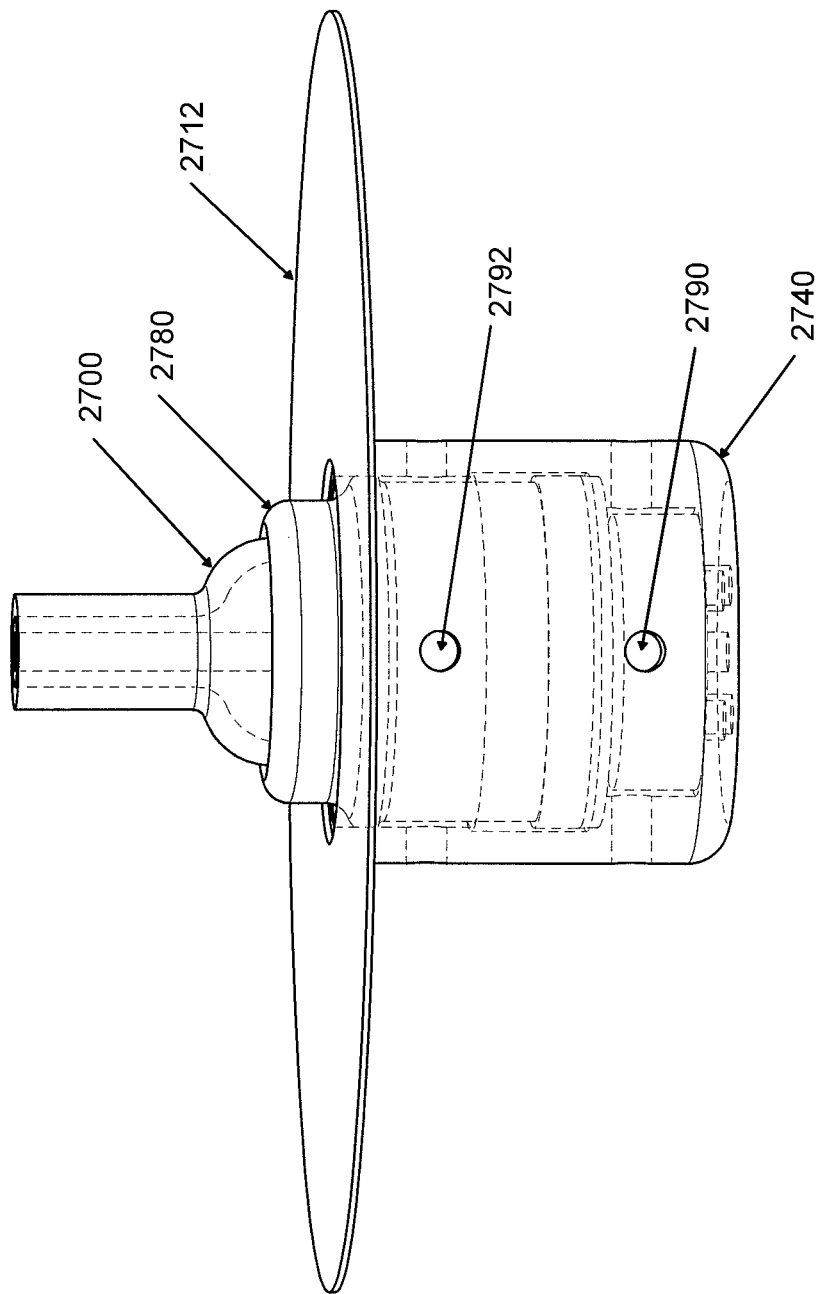
Figure 28A:
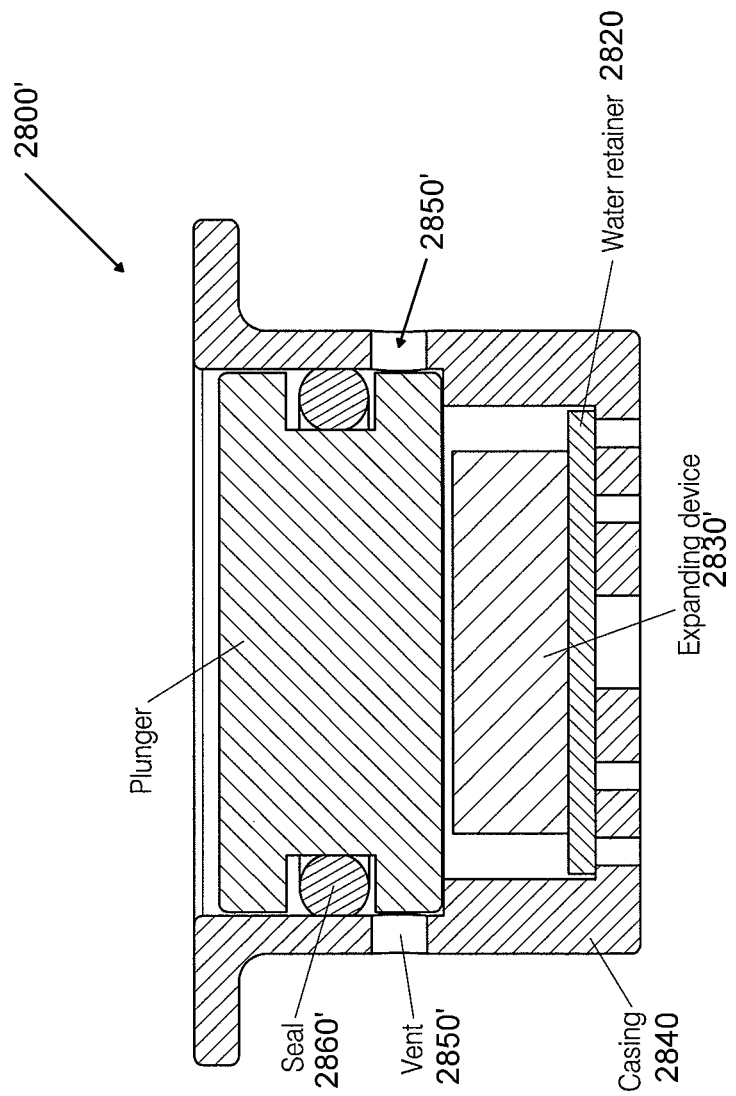
FIGS. 28A-D depicts a deflation port 2800, including a plunger 2810, seal 2860, vent 2850, casing 2840, expanding device 2830, and water retainer 2820.
Figure 28B:
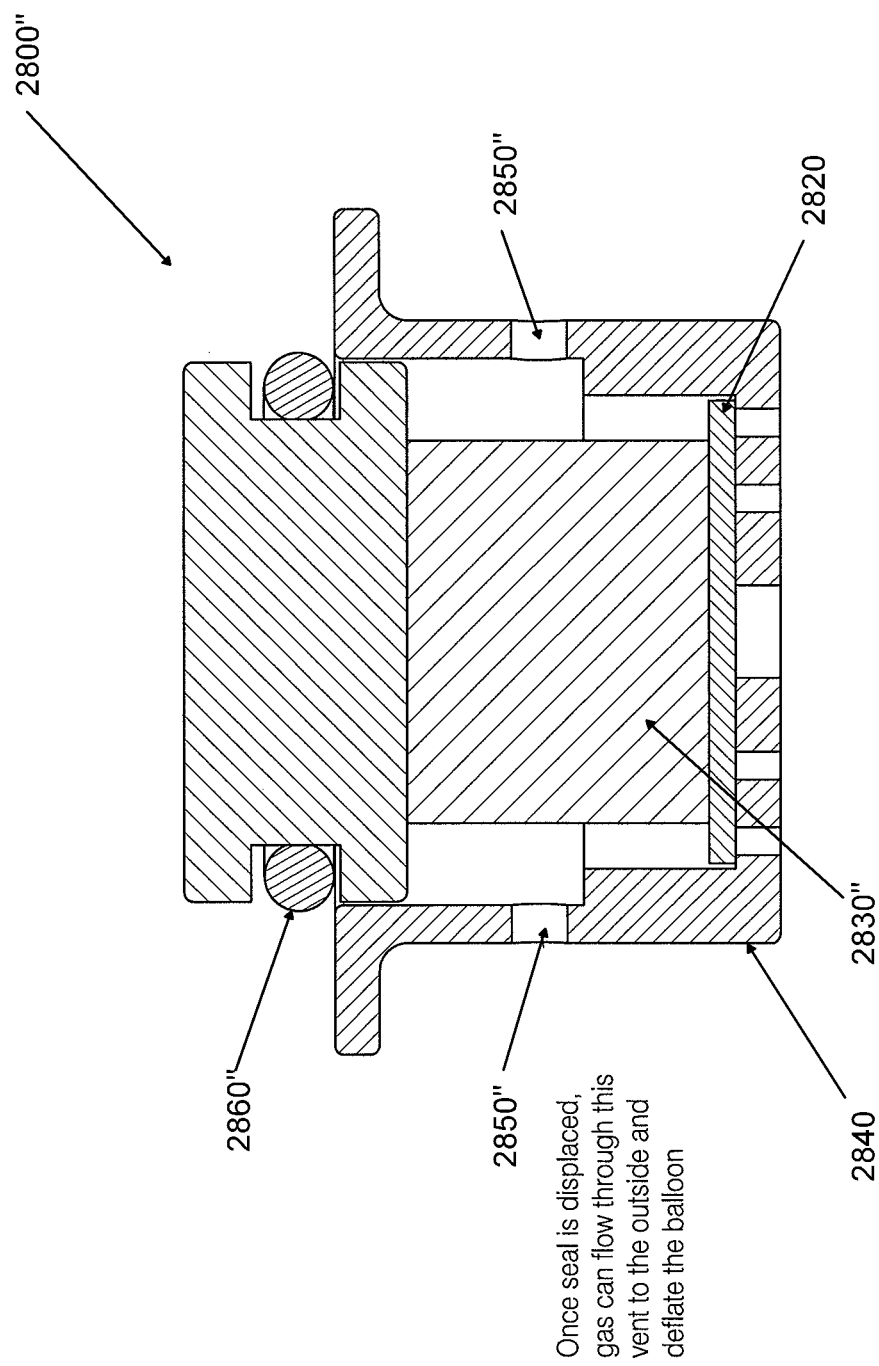
Figure 28C:
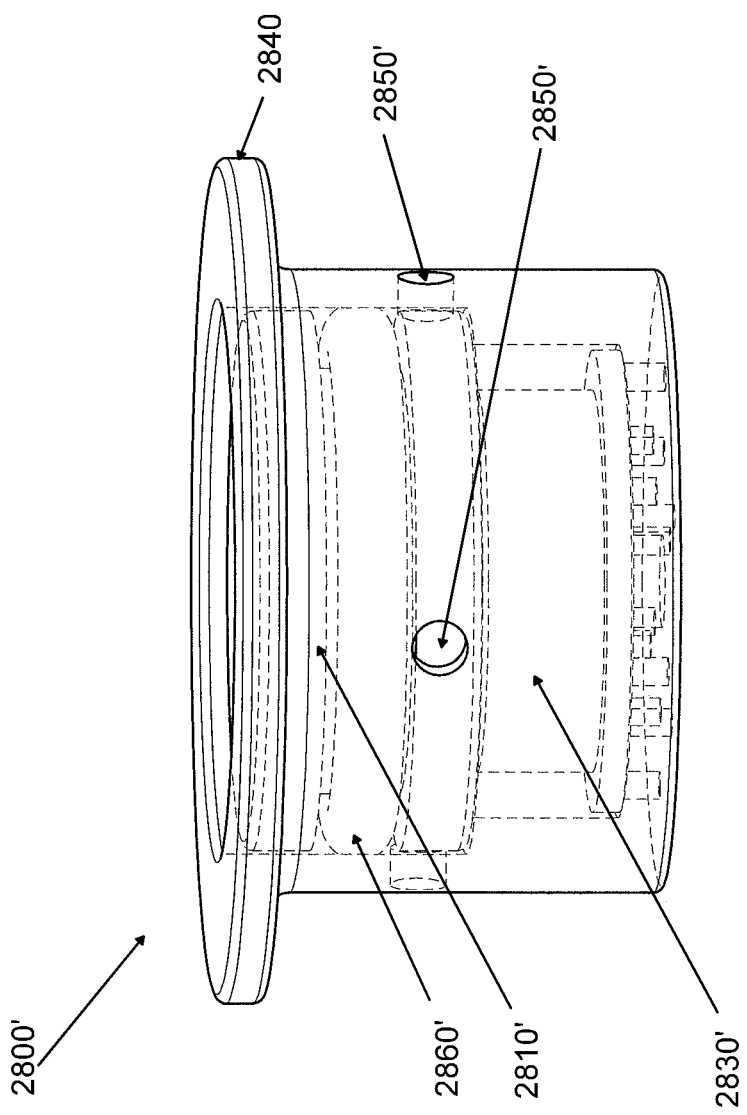
Figure 28D:
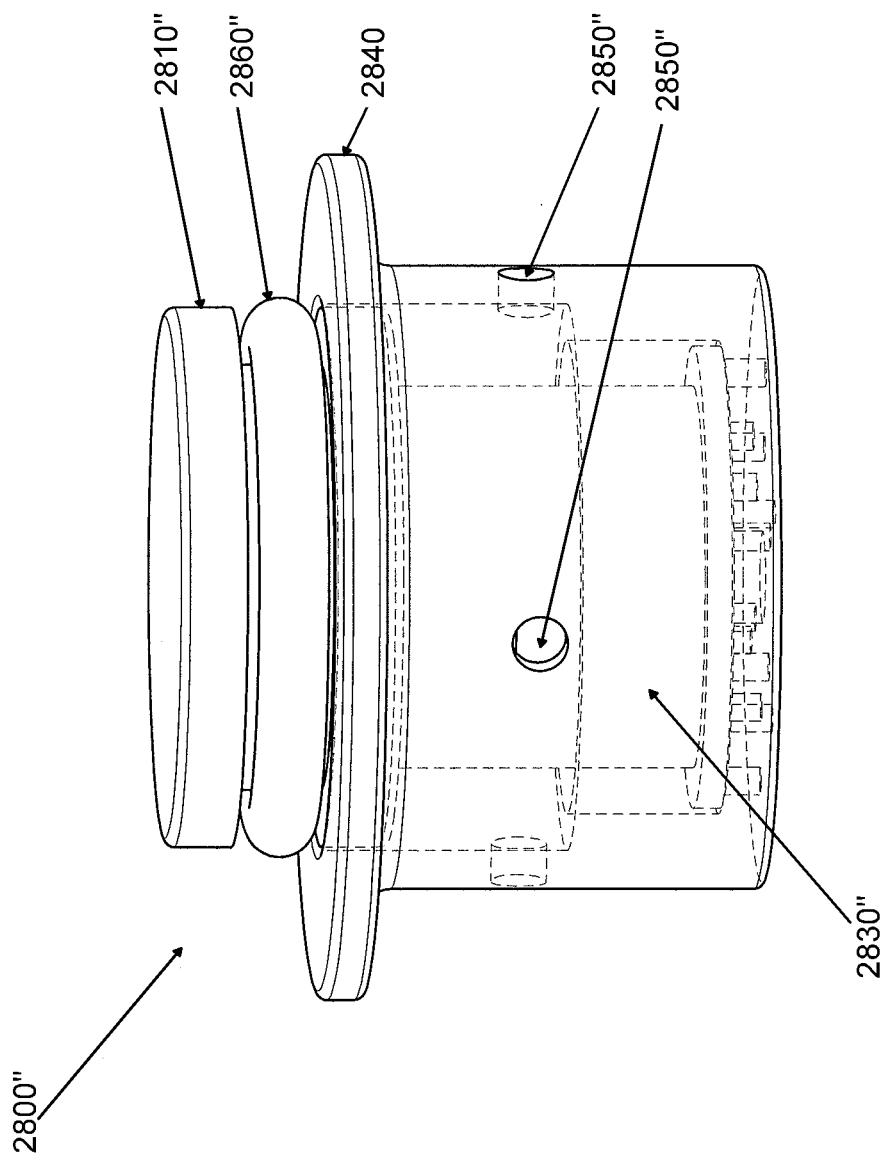

A preferred embodiment of manually inflated balloon that also possesses a mechanism for self-deflation would be a port that encompasses an inflation and deflation mechanism in the same location (See FIG. 27A). The device comprises a catheter needle sleeve, e.g., of nylon or plastic that seals to silicon parts, that is attached to inflation tube when filling. It further comprises a silicon head which seals to the needle sleeve, allowing for inflation and detachment from the catheter. The silicon head also seals to part #6 until pushed out of position by expanding part #7. The needle, e.g., fabricated from stainless steel, inflates the balloon. A compression Seal between part #6 and #2 vents internal gas when displaced. An insert, e.g., of titanium, provides imaging visibility (FIG. 27B), and provides rigid support for parts #2 and #4, and interference locks, sliding fits, and press fits to part #6. A septum, e.g., of silicon, seals to part #3 during inflation. The casing, e.g., PEEK or hard plastic, bonds to the balloon outer film and provides a sealing surface to part #2. It contains vents from inside the balloon to outside the balloon after part #7 expands. The expanding device, e.g., polyacrylamide in a binder material surrounded by a controlled moisture vapor transmission rate material (assorted blends of polyurethanes in varying thicknesses) uses the moisture available inside the balloon to uptake and swell in size. The press fit between parts #5 and #6 holds the parts firmly in position until part #7 begins to expand from moisture uptake.

In preferred embodiments, the invention includes a self-sealing valve that is compatible with an inflation catheter that contains a needle and needle sleeve. The self-sealing valve is sealed to the needle sleeve during the inflation process. Distal to the self-sealing valve is a titanium, stainless steel, MP35N, or any other radio-opaque rigid material insert that provides imaging visibility as well as mechanical support during the inflation process. Beneath the insert is the deflation mechanism that consists of an expanding device. The expanding device consists of a solute material, i.e. polyacrylamide material or the like encased in a binder material surrounded by moisture limiting material that has a defined moisture vapor transmission rate (MVTR). Moisture rate limiting material examples include but are not limited to assorted blends of polyurethanes in varying thicknesses. A hard plastic casing, such as PEEK, encompasses the self-sealing valves, the radio-opaque insert, the expanding material, and the moisture rate limiting material. The hard plastic case contains vents that would allow fluid to flow between the inside and outside of the balloon if the outer seal were not in position. The radio-opaque insert is coupled to the hard plastic casing via mechanical means, such as a press fit, that allow for linear movement but do not allow it to expel from the hard plastic casing. A second outer sealing valve creates an airtight seal to the hard plastic casing, blocking the casing vents, and moves linearly as the expanding device gains volume. Moisture placed inside of the balloon is absorbed by the expanding device as well as contributing moisture from the external gastric environment. Once the moisture transfers, the expanding material develops enough pressure such that the outer sealing valve is pushed linearly past the lip of the casing. This opens a vent pathway that allows the internal inflation fluid to quickly decompress and deflate the balloon. A deflated balloon allows for passing through the pylorus and through the remainder of the alimentary canal. One or multiple inflation/deflation ports on the surface of the balloon can be employed.

An alternative embodiment where the inflation port and deflation port are separate entities is depicted in FIG. 28. The device comprises a seal, e.g., of Buna rubber or similar sealing material, to provide an airtight seal between parts #1 and #3. It slides along the surface of part #3 until airtight seal fails and allows internal air out. The vent allows gas to flow from the balloon once the seals displaces. Also included are a titanium plunger, a water retainer (cotton or sponge-like material that is capable of retaining water and holding it against the surface of part #4 in order to maintain a constant moisture environment) and a casing of PEEK or other hard material that seals via adhesive to the balloon film and provides rigid containment for parts #1, 2, 4, and 5. The design also allows venting between internal and external balloon environment, and water ingress to part #4 which forces part #4 to expand in one direction. An expanding device, polyacrylamide in a binder material surrounded by a controlled moisture vapor transmission rate material (assorted blends of polyurethanes in varying thicknesses) uses the moisture available inside the balloon to uptake. The device can include a hard outer casing made of hard plastic or metal, an expanding device consisting of a super absorbent core surrounded by a moisture vapor transmission rate limiting membrane, and an airtight seal that is able to move linearly while the moisture expanding device grows in volume. The expanding device expands at a given rate based on how much moisture is available to it. In order to control the rate of expansion, a membrane, such as polyurethane, is used to control the desired moisture vapor transmission rate that is available to the super absorbent device. The moisture vapor transmission rate can be tuned by material formulation or material thickness. In order to maintain constant moisture contact to the moisture vapor limiting membrane, a sponge like material, such as cotton, can be used as a moisture reservoir for the expanding device. Once the expanding device pushes the seal past the lip of the hard outer casing, fluid can vent from inside the balloon to the external environment, causing the balloon to deflate and pass through the pylorus and the remainder of the alimentary canal. The balloon can have at least one deflation port but may have as many as deemed necessary to deflate the balloon such that it completely deflates and no residual inflation fluid remains that would cause a bowel obstruction (i.e., partial deflation).

A mechanism to facilitate passing involves an erosion mechanism that allows for the balloon to be broken down into a size that has a higher probability of predictably passing through the lower gastrointestinal system. Preferably, the size of the balloon as deflated is less than 5 cm long and 2 cm thick (similar to various foreign objects of similar size that have been shown to pass predictably and easily through the pyloric sphincter). This can be accomplished by providing the balloon with "erodible seams." One seam that breaks the balloon open into (at a minimum) two halves, or more seams are provided so that a plurality of smaller balloon pieces is produced in the dissociation reaction (FIG. 18). The number of seams used can be selected based on the original surface area of the balloon and what is required to dissociate the balloon into pieces that are of a size that can predictably pass through the gastrointestinal tract more easily. The rate of seam erosion can be controlled by using a material affected by, e.g., the external gastric environment pH, liquid, humidity, temperature, or a combination thereof. Seams can be single layer consisting of only erodible material, or multi-layer. The timing of self-deflation can be further controlled by the design of the seam layers, e g, making the reaction and/or degradation of the seam material dependent on the internal environment of the balloon instead of the external environment. By manipulating the reaction such that erosion or degradation is initiated by the internal environment (e.g., the balloon's internal pH, humidity, or other factors), any impact of person-to-person gastric variability (pH, etc.) that can affect erosion timing is minimized. The internal balloon environment can be manipulated by adding excess water at injection to create a more humid internal environment, or the amount of constituents added can be varied to manipulate the pH, etc.

The present invention has been described above with reference to specific embodiments. However, other embodiments than the above described are equally possible within the scope of the invention. Different method steps than those described above may be provided within the scope of the invention. The different features and steps of the invention may be combined in other combinations than those described. The scope of the invention is only limited by the appended patent claims.

All references cited herein are incorporated herein by reference in their entirety. To the extent publications and patents or patent applications incorporated by reference contradict the disclosure contained in the specification, the specification is intended to supersede and/or take precedence over any such contradictory material.

To the extent publications and patents or patent applications incorporated by reference herein contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein.

Terms and phrases used in this application, and variations thereof, unless otherwise expressly stated, should be construed as open ended as opposed to limiting. As examples of the foregoing, the term 'including' should be read to mean 'including, without limitation' or the like; the term 'comprising' as used herein is synonymous with 'including,' 'containing,' or 'characterized by,' and is inclusive or open-ended and does not exclude additional, unrecited elements or method steps; the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise. In addition, as used in this application, the articles 'a' and 'an' should be construed as referring to one or more than one (i.e., to at least one) of the grammatical objects of the article. By way of example, 'an element' means one element or more than one element.

The presence in some instances of broadening words and phrases such as 'one or more', 'at least', 'but not limited to', or other like phrases shall not be read to mean that the narrower case is intended or required in instances where such broadening phrases may be absent.

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. An intragastric balloon system comprising:
   a) an intragastric balloon comprising:
      i) a polymeric wall with an inner surface defining a balloon lumen;
      ii) a self-sealing valve system attached to the polymeric wall's inner surface, the valve system comprising:
         (1) a tube septum comprising:
            (a) an outer cylinder with a first end facing the w polymeric wall's inner surface and a second end facing the balloon lumen; and
            (b) an inner cylinder concentrically disposed within the outer cylinder and having a third end facing the polymeric wall's inner surface, and a fourth end facing the balloon lumen, the third end including an inward radial lip;
         (2) a self-sealing septum housed within the inner cylinder and compressed against the inner cylinder's inward radial lip; and
         (3) a polymeric material disposed concentrically between the inner cylinder and the outer cylinder;
   b) an outer container releasably containing the intragastric balloon in a folded and compacted state, the outer container comprising:
      i) an outer container wall formed of a material that is erodible in an in vivo gastric environment;
      ii) an outer container interior; and
      iii) an opening in the outer container wall, the opening in the outer container wall providing fluid communication between the outer container interior and the in vivo gastric environment; wherein
      iv) the outer container is sized and shaped so as to be swallowable by normal peristaltic motion;
   c) a swallowable inflation catheter comprising:
      i) catheter tubing with an open proximal end and open distal end joined by a catheter lumen;
      ii) a needle assembly attached to the catheter tubing distal end and including:
         (1) a needle sleeve extending through the opening in the outer container wall and reversibly engaged with the valve system, wherein the valve system's polymeric material provides compressive forces against the needle sleeve to provide an interference fit and sealing of the valve system to the inflation catheter sufficient to maintain a seal during inflation of the intragastric balloon while permitting detachment of the swallowable inflation catheter from the valve system after inflation of the intragastric balloon in vivo is complete; and
         (2) a hollow needle disposed within the needle sleeve and extending longitudinally through the self-sealing septum of the valve system, whereby the tubing lumen is in fluid communication with the intragastric balloon lumen;
      iii) a catheter connector attached to the catheter tubing proximal end; and
      iv) a tensile cord extending through the tubing lumen and attached to each of the needle assembly and the catheter connector.

2. The system of claim 1, wherein the polymeric material includes a longitudinally extending portion that does not protrude more than 2 mm past an outer surface of the polymeric wall.

3. The system of claim 1, wherein the polymeric material presses against the reversibly engaged needle sleeve to cooperatively provide sealing of the needle sleeve to the inflation valve.

4. The system of claim 1, wherein the needle sleeve is reversibly engaged between the polymeric material cylindrical surface and the inner cylinder.

5. The system of claim 1, the valve system further comprising a retaining ring providing a compressive force against the polymeric material.

6. The system of claim 1, wherein valve system is configured to provide a compressive force against the needle sleeve for inflation and detachment, such that the interference fit can withstand a pressure of 35 PSI during inflation.

7. The system of claim 6, wherein the seal of the valve system and the needle assembly is configured to be broken during detachment using a hydraulic pressure that is between 40 PSI and 200 PSI to separate the connection coupling.

8. The system of claim 1, wherein the polymeric material includes a cylindrical through-bore with a bore surface spaced from the inner cylinder.

9. The system of claim 1, wherein the inner cylinder is configured to control alignment of the needle assembly with the septum, provide a barrier to the needle piercing the polymeric wall, and provide compression such that the septum reseals after inflation and needle withdrawal.

10. The system of claim 1, further comprising:
    a) an inflation source container comprising:
       i) a volume of an inflation fluid, wherein the inflation fluid comprises at least one inert gas;
       ii) an inflation valve in fluid communication with the volume of the inflation fluid; wherein
          (1) the inflation valve is sized and shaped to reversibly connect to the catheter connector; and wherein
          (2) the inflation valve includes opened and closed configurations and an actuation handle; and
       iii) a pressure gauge attached to the volume of inflation fluid; wherein
    b) the inflation source container is configured to utilize information regarding inflation pressure as a function of time to provide feedback to a user, wherein the feedback indicates a condition selected from the group consisting of failure by mechanical blockage, failure by esophagus constraint, failure by inflation catheter leak or detachment, and successful balloon inflation.

11. The system of claim 10, wherein the pressure gauge provides a pressure within the volume of inflation fluid.

12. The system of claim 10, wherein the inert gas is selected from the group consisting of $N_2$, $O_2$, $CO_2$, a single gas, and a mixture of gases.

13. The system of claim 1, further comprising:
a) a detachment device for detachment of the inflation catheter after inflation of the intragastric balloon in vivo is complete, the detachment device comprising:
   i) a volume of physiological compatible detachment liquid;
   ii) a connection end configured for connection to the catheter connector; and
   iii) a plunger; wherein
b) actuation of the plunger expels detachment liquid from the detachment device, thereby generating hydraulic pressure against the balloon valve system; and wherein
c) the interference fit between the needle assembly and the balloon valve system is insufficient to maintain the seal upon application of the hydraulic pressure by the detachment liquid, such that upon application of the hydraulic pressure to the needle assembly is ejected from the balloon valve system.

14. The system of claim 13, wherein the hydraulic pressure is between 40 PSI and 200 PSI to separate the connection coupling.

15. The system of claim 1, wherein the polymeric wall comprises one or more layers.

16. The system of claim 15, wherein the polymeric wall comprises a barrier material comprising nylon and polyethylene.

17. The system of claim 15, wherein the polymeric wall comprises a barrier material comprising nylon, polyvinylidene chloride and polyethylene.

18. The system of claim 1, wherein the inflation catheter is of a variable stiffness.

19. The system of claim 1, wherein the inflation catheter tubing is from 1 French to 6 French in diameter.

20. The system of claim 1, wherein a plurality of intragastric balloons is connected to a single inflation catheter.

21. The system of claim 1, further comprising:
a) a deflation port attached to the wall inner surface, the deflation port comprising
   i) a casing with one or more vent pathways attached to the wall inner surface,
   ii) an outer sealing member positioned to block the one or more vent pathways; and
   iii) a deflation component situated in the casing and is configured to expand upon exposure to moisture inside the balloon lumen via the one or more vent pathways, wherein
   iv) the expanding deflation component pushes the outer sealing member to thereby open the one or more vent pathways so as to provide fluid communication between the in vivo gastric environment and the balloon lumen.

22. The system of claim 21, wherein the deflation port is configured to rapidly deflate the intragastric balloon after 60 or more days in vivo.

23. The system of claim 21, wherein the valve system comprises the deflation port.

24. The system of claim 21, wherein the deflation component comprises a solute material encapsulated in a binder material, wherein the deflation component is further surrounded by moisture limiting material that has a predefined moisture vapor transmission rate.

25. The system of claim 24, wherein the solute material is a polyacrylamide.

26. The system of claim 21, wherein the deflation port comprises a rigid retaining structure, and wherein the rigid retaining structure and the casing have a press fit lock that prevents the rigid retaining structure from being expelled from the casing after maximum displacement by the deflation component.

* * * * *